(12) United States Patent
Naruse et al.

(10) Patent No.: US 8,501,642 B2
(45) Date of Patent: Aug. 6, 2013

(54) NANO-FIBER COMPOUND SOLUTIONS, EMULSIONS AND GELS, PRODUCTION METHOD THEREOF, NANO-FIBER SYNTHETIC PAPERS, AND PRODUCTION METHOD THEREOF

(75) Inventors: Yoshihiro Naruse, Otsu (JP); Takeo Matsunase, Moriyama (JP); Takashi Ochi, Mishima (JP); Kakuji Murakami, Ritto (JP); Shuichi Nonaka, Otsu (JP)

(73) Assignee: Toray Industries, Inc. (JP)

( * ) Notice: Subject to any disclaimer, the term of this patent is extended or adjusted under 35 U.S.C. 154(b) by 1219 days.

(21) Appl. No.: 10/589,411

(22) PCT Filed: Feb. 16, 2005

(86) PCT No.: PCT/JP2005/002310
§ 371 (c)(1),
(2), (4) Date: Nov. 15, 2006

(87) PCT Pub. No.: WO2005/080679
PCT Pub. Date: Sep. 1, 2005

(65) Prior Publication Data
US 2007/0196401 A1    Aug. 23, 2007

(30) Foreign Application Priority Data

Feb. 19, 2004 (JP) .................................. 2004-42880
Mar. 16, 2004 (JP) .................................. 2004-74238

(51) Int. Cl.
*D04H 1/00* (2006.01)
*B01D 24/00* (2006.01)

(52) U.S. Cl.
USPC .......... 442/327; 442/334; 442/363; 442/400; 977/762; 210/348; 210/500.1

(58) Field of Classification Search
USPC .................. 428/401, 373, 374; 442/351, 363, 442/327, 334, 400; 264/211.12, 640; 977/762; 210/348, 500.1
See application file for complete search history.

(56) References Cited

U.S. PATENT DOCUMENTS

| | | |
|---|---|---|
| 3,382,305 A | 5/1968 | Alvin L. Breen |
| 3,546,063 A | 12/1970 | Alvin L. Breen |

(Continued)

FOREIGN PATENT DOCUMENTS

| | | |
|---|---|---|
| DE | 29907699 | 8/1999 |
| EP | 0498672 | 8/1992 |

(Continued)

OTHER PUBLICATIONS

H. Fong et al., "Beaded nanofibers formed during electrospinning," Polymer, vol. 40, © 1999 Elsevier Science Ltd., pp. 4585-4592.

(Continued)

*Primary Examiner* — Matthew Matzek
(74) *Attorney, Agent, or Firm* — DLA Piper LLP (US)

(57) ABSTRACT

This invention provides compound solutions, emulsions and gels excellent in homogeneous dispersibility and long-term dispersion stability and also excellent in the properties as cosmetics, using disarranged nanofibers not limited in either form or polymer, widely applicable and small in the irregularity of single fiber diameter. This invention also provides a method for producing them. Furthermore, this invention provides synthetic papers composed of fibers, small in pore area and uniform in pore size, using disarranged nanofibers, and also provides a method for producing them. This invention provides compound solutions, emulsions, gels and synthetic papers containing disarranged nanofibers of 1 to 500 nm in number average diameter and 60% or more in the sum Pa of single fiber ratios.

17 Claims, 5 Drawing Sheets

U.S. PATENT DOCUMENTS

| | | | |
|---|---|---|---|
| 4,043,331 A | 8/1977 | Ernest et al. | |
| 5,290,626 A * | 3/1994 | Nishioi et al. | 442/201 |
| 6,489,283 B1 | 12/2002 | Afriat | |
| 2002/0092423 A1* | 7/2002 | Gillingham et al. | 95/287 |
| 2002/0175323 A1 | 11/2002 | Guillom | |
| 2003/0106294 A1* | 6/2003 | Chung et al. | 55/486 |
| 2003/0168401 A1* | 9/2003 | Koslow | 210/500.25 |
| 2004/0031749 A1* | 2/2004 | Koslow | 210/505 |
| 2005/0008776 A1* | 1/2005 | Chhabra et al. | 427/180 |

FOREIGN PATENT DOCUMENTS

| | | |
|---|---|---|
| EP | 1 371 679 | 12/2003 |
| JP | 49-8809 | 2/1974 |
| JP | 55-28947 A | 2/1980 |
| JP | 55-110545 A | 8/1980 |
| JP | 56-169899 A | 12/1981 |
| JP | 60-34700 A | 2/1985 |
| JP | 62-39507 A | 2/1987 |
| JP | 63-215770 A | 9/1988 |
| JP | 64-026603 | 1/1989 |
| JP | 1-118700 A | 5/1989 |
| JP | 3-113082 A | 5/1991 |
| JP | 4-10992 A | 1/1992 |
| JP | 04-126891 | 4/1992 |
| JP | 5-186323 A | 7/1993 |
| JP | 6-211626 A | 8/1994 |
| JP | 6-272114 A | 9/1994 |
| JP | 7-2639 A | 1/1995 |
| JP | 7-185294 A | 7/1995 |
| JP | 7-196440 A | 8/1995 |
| JP | 8-27192 A | 1/1996 |
| JP | 8-209583 A | 8/1996 |
| JP | 10-67685 A | 3/1998 |
| JP | 10-87428 A | 4/1998 |
| JP | 10-147506 A | 6/1998 |
| JP | 11-100510 A | 4/1999 |
| JP | 2000-128760 A | 5/2000 |
| JP | 2000-264632 A | 9/2000 |
| JP | 2001-001252 | 1/2001 |
| JP | 2001-2523 A | 1/2001 |
| JP | 2001-64153 A | 3/2001 |
| JP | 2001-89314 A | 4/2001 |
| JP | 2001-114631 A | 4/2001 |
| JP | 2001-139753 A | 5/2001 |
| JP | 2001-214081 A | 8/2001 |
| JP | 2001-261526 A | 9/2001 |
| JP | 03-243685 | 10/2001 |
| JP | 2002-20217 A | 1/2002 |
| JP | 2002-266281 A | 9/2002 |
| JP | 2002-275032 A | 9/2002 |
| JP | 2002-327386 A | 11/2002 |
| JP | 2003-26564 A | 1/2003 |
| JP | 2003-45752 A | 2/2003 |
| JP | 2003-59482 A | 2/2003 |
| JP | 2003-109569 A | 4/2003 |
| JP | 2003-129393 A | 5/2003 |
| JP | 2003-239170 A | 8/2003 |
| JP | 2003-253555 A | 9/2003 |
| JP | 2003-300844 A | 10/2003 |
| JP | 2004-35571 A | 2/2004 |
| WO | 02/20130 | 3/2002 |
| WO | 02/20668 | 3/2002 |
| WO | 03/016048 | 2/2003 |
| WO | 03/044100 | 5/2003 |
| WO | 03/064006 | 8/2003 |

OTHER PUBLICATIONS

Xinhua Zong et al., "Structure and process relationship of electrospun bioabsorbable nanofiber membranes," Polymer, vol. 43, © 2002 Elsevier Science Ltd., pp. 4403-4412.

* cited by examiner

NANO-FIBER COMPOUND SOLUTIONS, EMULSIONS AND GELS, PRODUCTION METHOD THEREOF, NANO-FIBER SYNTHETIC PAPERS, AND PRODUCTION METHOD THEREOF

TECHNICAL FIELD

The present invention relates to solutions, emulsions and gels containing ultrafine fibers with a fiber diameter on the order of nanometers (nm) (hereinafter called nanofibers) useful in such fields as cosmetic field, paint field, medical field and electronic material field, and also relates to various products using them such as cosmetics and paints, and a production method thereof.

Furthermore, this invention relates to synthetic papers composed of nanofibers and having small pore areas and uniform pore sizes, and also to a production method thereof.

BACKGROUND

Cosmetics with diverse functions are proposed recently. For example, they include cosmetics capable of easily keeping the skin healthy, capable of favorably adhering to the skin and capable of being easily washed away, cosmetics containing ingredients capable of preventing aging and keratinization such as collagen, hyaluronic acid, squalane and urea or an ingredient capable of preventing skin roughening such as allantoin, skin whitening cosmetics containing an ultraviolet absorber such as benzophenone or zinc oxide for preventing blackening, ephelides or freckles, or containing a melanin production inhibitor such as arbutin or squalane, or capable of activating skin cells, cosmetics containing a moisture retaining agent or moistening agent such as glycerol, hyaluronic acid, silicone or lanolin and capable of keeping the skin moist, fresh and youthful, cosmetics containing an organic substance and capable of keeping the intended cosmetic effect lasting longer, cosmetics capable of preventing the darkening or partial glistening of the skin, cosmetics capable of expressing quality such as transparency or color tone, etc.

To impart these functions, various oily ingredients, moisture retaining agents, thickeners, whitening agents, ultraviolet absorbers, fine particles, dyes and the like for protecting the skin are mixed with water or any other solvent. These practices involve such production problems that it may be difficult to homogeneously disperse the respective ingredients and to stabilize the produced emulsions. Furthermore, the produced cosmetics are required to be good in the homogeneity and dispersibility of ingredients contained in them and furthermore to be excellent in long-term storage stability. Moreover, cosmetics are required to be excellent in the feeling of use during make-up, for example, in touch to the hand, smooth spreadability and touch to the skin, long-lasting in spite of the perspiration produced after make-up, and easy to remove.

Studies for solving the above-mentioned various problems of conventional cosmetics are conducted by using surfactants and natural dispersing agents, or loading such bases as inorganic fine particles, organic fine particles, polymer gels, natural gels and collagen with various compounding ingredients, or dispersing various compounding ingredients using acrylamide-based polymeric thickeners, etc., for improving the homogeneous dispersibility and stability of respective compounding ingredients.

In the recent studies of cosmetics, for dispersing an oil ingredient as a compounding ingredient, microdispersion techniques of using fine particles with a particle size of 1 μm or less as the oil ingredient are being studied (for example, JP10-147506A, JP2001-214081A, and JP2001-261526A). Furthermore, for using inorganic fine particles as a compounding ingredient, techniques of mixing fine particles with a diameter of 0.1 μm or less (hereinafter called nanoparticles) are being studied (for example, JP05-186323A, JP2000-264632A, JP07-002639A, JP2001-089314A, and JP2003-300844A). The homogeneous dispersion of an oil ingredient consisting of fine particles or a solid ingredient consisting of fine particles as described above can be improved to some extent by conventional methods such as selecting the lipid used or using an optimum surfactant for surface tension control. However, it is more difficult to achieve long-term storage stability when the diameter of the fine particles is smaller. Especially nanoparticles are highly likely to cohere to each other, and on the contrary to the intended dispersion, they form secondarily cohering particles of micron sizes, to settle. They have a problem that the intended object of homogeneously dispersing nanoparticles cannot be achieved.

For enhancing the homogeneous dispersibility of compounding ingredients and fine particles or for keeping the dispersed state stabilized for a long period of time, the use of a glycerol (for example, JP07-185294A and JP2000-128760A), the use of an acrylamide (for example, JP06-211626A and JP10-067685A), and the like are studied. However, these methods include cases where the dispersibility of the dispersing agent per se is not sufficient or where the long-term stability is not sufficient. For example, oil-in-water emulsions in which the diameter of acrylamide particles is 50 to 1000 nm (for example, JP10-087428A) are disclosed. However, this dispersing agent, if used as fine particles, makes the user feel sticky due to the nature of acrylamide per se, having a disadvantage that the freshness, refreshing feel and natural feel expected for the cosmetic used are lost, though it is good in smooth spreadability to the skin and excellent in touch to the skin when it is applied to the skin.

In this situation, demanded are materials good in the homogeneous dispersion of compounding ingredients and fine particles, long-term storage stability, adhesion to the skin and smooth spreadability, excellent also in touch to the skin, furthermore free from the sticky feel during use, and also excellent in the freshness, refreshing feel and natural feel expected for the cosmetic used.

As methods for obtaining such materials, it is proposed to use a clay material such as talc or bentonite or inorganic particles as a carrier and to let compounding ingredients adhere to it for dispersion. However, since the particle size of the carrier is as large as more than several micrometers, it is difficult to homogeneously disperse it into to the cosmetic, and since the particle size of the carrier is large, the user feels gritty, posing a problem of impairing freshness and natural feel.

As other methods, studied are cosmetics containing natural fibers such as collagen fibers as a compounding ingredient other than said organic fine particles and inorganic fine particles (for example, JP55-28947A, JP63-215770A and JP08-27192A). These cosmetics use materials modified to allow easy permeation or absorption into the skin by lowering the molecular weight of collagen or by chemically modifying collagen fibers, and though the materials are fibers, the configuration and function of the fibers used as a carrier are not so significant. Cases where silk fibroin fibers are made finer are also disclosed (for example, JP11-100510A). However, while they are short fibers with a length of 1 to 200 μm, they have a diameter of about 10 μm, and they should be called a silk powder of 10 μm or more in particle size rather than fine fibers. As particles, they are large, and the silk powder per se is poor in dispersibility and is likely to settle. These properties are not sufficient as the properties required as a material for carrying other nanoparticles to be dispersed in them. Moreover, there are further other methods in which cellulose fibers are used (for example, JP62-39507A), and in the case where such cellulose fibrils are used, the cellulose fibril fibers are very irregular in diameter, ranging from 1/10 to 1/100, consisting of large diameter fibers and small diameter fibers mixed together. It is very difficult to homogeneously disperse them, and furthermore the fibers also have a disadvantage that since the large diameter fibers are likely to settle, fine particles settle together rather than being dispersed. Moreover, the fibers have such disadvantages that mold and mildew are generated during storage and that the fibers per se are highly rigid and insufficiently flexible.

Furthermore, there are cases where cellulose nanofibers are used (for example, JP13-2523A), but the fibers have such problems that they are low in absolute strength, that the cellulose fibers are broken into fragments when dispersed, and that because of cellulose, mold and mildew are generated during storage of the dispersion. From this point of view, it is required to use ultrafine fibers made of a synthetic polymer, instead of cellulose.

As cosmetics containing ultrafine fibers made of a synthetic polymer, "cosmetics containing ultrafine fibers" intended for obtaining luster like velvet or natural luster like baby's lanugo (for example, JP2001-64153A) are disclosed. Though the ultrafine fibers used here are as short as 50 μm or less in fiber length, they have a fiber diameter of 2 μm (0.055 dtex). So, in the case where the fibers are mixed in a cosmetic, they are still large in fiber diameter, insufficient in flexibility and poor in affinity with the skin, making the user feel stress from the cosmetic coating, and can be used only for special make-up application. Furthermore, the fibers per se are insufficient in dispersibility into water or oil and in affinity with fine particles. So, though they can be used as ultrafine fibers for woven fabrics, knitted fabrics, nonwoven fabrics, etc., it is difficult to apply them in the cosmetic field, since they are insufficient in fiber diameter and flexibility.

In the meantime, methods for producing a synthetic paper from ultrafine fibers of a synthetic polymer are known, and various methods have been studied to use a dispersion of fibers for wet papermaking, etc. The number average diameter of ordinary single synthetic fibers is as large as 10 μm or more, and it is difficult to fibrillate them unlike natural pulp or cellulose. The fibers can be little entangled with each other, and it is difficult to obtain a synthetic paper with good evenness. So, for synthetic papers of polyester fibers, it was studied to use a binder together with polyester fibers for papermaking. The diameters of fibers used in these studies were about 13 μm (for example, JP49-8809B), about 15 μm (for example, JP55-110545A and JP60-34700A), and about 11 μm (for example, JP1-118700A). However, the synthetic papers obtained were rather insufficient in flexibility. Moreover, when the paper thickness was reduced for enhancing flexibility or air permeability, a synthetic paper with good evenness could not be obtained since the fibers were thick and poor in dispersibility. Furthermore, in the case where the paper thickness was forcibly reduced, the paper became irregular in the weight per unit area sometimes, not allowing practical use.

In this situation, recently synthetic papers composed of ultrafine fibers with a diameter of 10 μm or less are also being studied. As for the methods, the sea component is dissolved or physically removed for separation from an islands-in-sea multi-component fiber or from a splittable conjugate fiber, to prepare ultrafine fibers, and the obtained ultrafine fibers are used to produce a synthetic paper. The basic methods for producing such ultrafine fibers are already disclosed (for example, U.S. Pat. No. 3,382,305), and the ultrafine fibers per se are also disclosed (for example, U.S. Pat. No. 3,546,063). According to them, a method of removing the sea component from an islands-in-sea multi-component polyester fiber using an adequate solvent is used to obtain ultrafine fibers, and it is suggested that the ultrafine fibers can be used to produce a paper-like structure. However, since the ultrafine fibers obtained were very irregular in diameter, ranging from 0.01 to 3 μm, a practically usable synthetic paper was not obtained.

Thereafter, methods for treating an islands-in-sea multi-component fiber or a splittable conjugate fiber of 10 μm or less by a high pressure fluid for obtaining synthetic papers of ultrafine fibers (for example, JP56-169899A) are proposed. However, it was difficult to practically use the methods, for such reasons that it was difficult to uniformly fibrillate the fibers and that a special high pressure fluid device was necessary. Furthermore, islands-in-sea multi-component polyester fibers were dispersed and beaten in water, to obtain a synthetic paper composed of polyester fibers with a diameter of 1.5 to 4 μm (for example, JP4-10992A). Moreover, splittable conjugate fibers respectively consisting of polyolefin based resins different in components were beaten and the obtained fibers were used to produce a synthetic paper (separator material) (for example, JP2003-59482A). These fibers were about 5 μm in fiber diameter, and the split single fibers were uneven in form. So, they were very irregular in diameter. Furthermore, synthetic papers obtained by using the ultrafine fiber bundles of islands-in-sea multi-component fibers or splittable conjugate fibers and their short fibers were disclosed (for example, JP2003-253555A), but the fibers of the synthetic papers had a large diameter of 2 to 7 μm.

In addition, methods in which ultrafine fibers obtained by fibrillating liquid crystal fibers are used to obtain a synthetic paper are proposed (for example, JP8-209583A and JP2002-266281A). However, in these methods, though very fine fibers can be obtained by fibrillation, thick fibers not fibrillated so much also remain to mix with the very fine fibers. So, only a synthetic paper very irregular in single fiber diameter could be obtained.

On the other hand, in the applications of synthetic papers, especially in the fields of air cleaner filters, industrial dust removing filters, pure water producing filters, chemical reagent refining filters, medicinal/medical filters, battery separators, etc., a thinner synthetic paper with a uniform weight per unit area and a high strength is being demanded. The reason is that highly accurate control is required for removing very fine impurities outside the system or for recovering very necessary fine components in electronics field, mechatronics field, water quality field, drug/chemicals or food handling field, etc. So, there have been needs for studies on synthetic papers composed of nanofibers.

Methods of using conventional spinning techniques for islands-in-sea multi-component fibers allow the production of single fibers with a diameter of about 1 μm, but do not allow the production of fibers with a diameter smaller than it. Thus, the methods cannot sufficiently meet the needs for nanofibers. Furthermore, methods for obtaining ultrafine fibers from blended polymer fibers (for example, JP3-113082A and JP6-272114A), and the smallest diameter of the single fibers obtained as ultrafine fibers is about 0.4 μm. Thus, the methods cannot sufficiently meet the needs for nanofibers either. Moreover, the diameter of the single fibers obtained as ultrafine fibers is decided by the dispersion of the polymer used as the island component in the blended polymer fibers, and since the dispersion of the polymer used as the island component in such an ordinary polymer blend system is insufficient, the obtained ultrafine fibers are very irregular in single fiber diameter.

In the meantime, as a simple technique for reducing the diameter of ultrafine fibers to the nanometer level, a technique called electrospinning is spotlighted in recent years. The basic technique of the method has been known since a long time ago, and the method was proposed about 1935. The reasons why this technique is highlighted are that the nanofiber nonwoven fabric (like a synthetic paper) produced by this method is suitable especially as a material for cell culture in the biomedical field of USA, and that nonwoven fabrics of various polymers can be easily produced for research. In this method, a solution obtained by dissolving a polymer into an electrolyte solution is extruded from a die. In this technique, a high voltage of several thousand to thirty thousand volts is applied to the polymer solution, and the folding and expansion of the high speed jet and the subsequent jet of the polymer solution are used for forming ultrafine fibers. Usually these ultrafine fibers are bundled to be collected as a nonwoven fabric like a synthetic paper. If this technique is used, single fibers with a diameter of tens of nanometers can be obtained, and the diameter can be reduced to 1/10 or less of the diameters obtained by the conventional polymer blending techniques as the case may be. The polymers used are mostly biopolymers such as collagen and water soluble polymers, and in some cases a solution obtained by dissolving a thermoplastic polymer into an organic solvent may also be electrospun. However, each of the ultrafine fibers obtained even by this method often consists of ultrafine fiber portions connected by thick fiber portions (beads with a diameter of 0.5 µm), and each of the ultrafine fibers is very irregular in single fiber diameter {for example, Polymer, Vol. 43, 4403 (2002)}. Therefore, it is attempted to inhibit the production of the thick fiber portions for uniforming the fiber diameters, but the irregularity remains large, the problem remaining yet to be solved {for example, Polymer, Vol. 40, 4585 (1999)}. Furthermore, since the nonwoven fabric obtained by electrospinning is obtained as the solvent is evaporated in the step of fiber formation, the fiber aggregate is often not oriented or crystallized, and a nonwoven fabric with a strength very lower than those of ordinary nonwoven fabrics only can be obtained to greatly restrict its applicable range. Moreover, because of the solvent evaporated in the step of fiber formation, the electrospinning as a production technique has such problems that any measure must be taken to improve the working environment and that the solvent must be recovered. Furthermore, the nonwoven fabric that can be produced is also limited in size, and the size that can be produced is about 100 cm$^2$. Moreover, the discharge rate is several grams per hour at the largest, to lower the productivity. In addition, a high voltage is necessary, and since a harmful organic solvent and ultrafine fibers float in air, risks of electric shock, explosion and poisoning keep lingering. So, the method has been practically difficult.

As described above, needed is a synthetic paper composed of nanofibers not limited in the selection of polymers, allowing a wide range of applications and small in the irregularity of single fiber diameter.

Meanwhile, the following formula (1) holds between the fineness (dtex) usually often used for the fibers described in the above-cited patent documents, etc. and the number average diameter ϕ (µm) of the single fibers used to form the synthetic paper of this invention.

$$\phi = 10 \times (4 \times dtex/\pi\rho)^{1/2} \quad (1)$$

where dtex is the thickness of a fiber, at which the fiber with a length of 10000 m weighs 1 g (JIS L 0101) (1978).

For example, for converting a fineness into the number average single fiber diameter referred to in this invention, if the polymer is nylon, the number average diameter can be obtained from the following formula with the specific gravity as 1.14 (of nylon 6).

$$\phi_{n6} = 10.6(dtex)^{1/2}$$

If the polymer is not nylon 6, the specific gravity of the polymer can be used in the above formula for calculating the number average single fiber diameter.

SUMMARY

We provide compound solutions, emulsions and gels excellent in homogeneous dispersibility and in the long-term stability of dispersion and also excellent in the properties as cosmetics.

Furthermore, we provide synthetic papers composed of nanofibers not limited in the form or polymer used, allowing a wide range of application and small in the irregularity of single fiber diameter, and a production method thereof.

Thus, we provide the following:

(1) A compound solution comprising disarranged fibers made of a thermoplastic polymer, and of 1 to 500 nm in the number average single fiber diameter and 60% or more in the sum Pa of single fiber ratios, and a solvent.

(2) A compound solution comprising disarranged fibers made of a thermoplastic polymer, and of 1 to 200 nm in the number average single fiber diameter and 60% or more in the sum Pa of single fiber ratios, and a solvent.

(3) A compound solution, according to said (1) or (2), wherein the index Pb of extremal coefficient of single fiber diameters expressing the rate of the fibers falling within a range of plus and minus 15 nm from the number average single fiber diameter defined as the median is 50% or more.

(4) A compound solution, according to said (1), wherein the solvent is at least one selected from the group consisting of water, oils and organic solvents.

(5) A compound solution, according to said (1) or (2), wherein the freeness of the disarranged fibers is 350 or less.

(6) A compound solution, according to said (1), wherein the content of the disarranged fibers is 5 wt % or less.

(84) A compound solution, according to said (1), wherein the disarranged fibers are short fibers with a fiber length of 5 mm or less.

(85) A compound solution, according to said (1), wherein the thermoplastic polymer is at least one selected from the group consisting of polyesters, polyamides, polyolefins, polyphenylene sulfide, phenol resins, polyacrylonitrile, polyvinyl alcohol, polysulfones, polyurethanes, fluorine-based polymers and their derivatives.

(86) A compound solution, according to said (1), which further contains a dispersing agent.

(87) A compound solution, according to said (86), wherein the content of the dispersing agent is 0.00001 to 20 wt %.

(88) A compound solution, according to said (86), wherein the dispersing agent is at least one selected from the group consisting of nonionic dispersing agents, anionic dispersing agents and cationic dispersing agents.

(89) A compound solution, according to said (88), wherein the zeta potential of the disarranged fibers is in a range from −5 to +5 mV, and the dispersing agent is a nonionic dispersing agent.

(90) A compound solution, according to said (88), wherein the zeta potential of the disarranged fibers is −100 mV to less than −5 mV, and the dispersing agent is an anionic dispersing agent.

(91) A compound solution, according to said (88), wherein the zeta potential of the disarranged fibers is more than +5 mV to 100 mV, and the dispersing agent is a cationic dispersing agent.

(92) A compound solution, according to said (86), wherein the molecular weight of the dispersing agent is 1000 to 50000.

(93) An emulsion comprising disarranged fibers made of a thermoplastic polymer, and of 1 to 500 nm in the number average single fiber diameter and 60% or more in the sum Pa of single fiber ratios, and a solvent.

(94) An emulsion comprising disarranged fibers made of a thermoplastic polymer, and of 1 to 200 nm in the number average single fiber diameter and 60% or more in the sum Pa of single fiber ratios, and a solvent.

(95) An emulsion, according to said (93) or (94), wherein the index Pb of extremal coefficient of the single fiber diameters expressing the rate of the fibers falling within a range of plus and minus 15 nm from the number average single fiber diameter defined as the median is 50% or more.

(96) An emulsion, according to said (93), wherein the solvent is at least one selected from the group consisting of water, oils and organic solvents.

(97) An emulsion, according to said (93) or (94), wherein the freeness of the disarranged fibers is 350 or less.

(98) An emulsion, according to said (93), wherein the content of the disarranged fibers is 5 wt % or less.

(99) An emulsion, according to said (93), wherein the disarranged fibers are short fibers with a fiber length of 5 mm or less.

(100) An emulsion, according to said (93), wherein the thermoplastic polymer is at least one selected from the group consisting of polyesters, polyamides, polyolefins, polyphenylene sulfide, phenol resins, polyacrylonitrile, polyvinyl alcohol, polysulfones, polyurethanes, fluorine-based polymers and their derivatives.

(101) An emulsion, according to said (93), which further contains a dispersing agent.

(102) An emulsion, according to said (101), wherein the content of the dispersing agent is 0.00001 to 20 wt %.

(103) An emulsion, according to said (101), wherein the dispersing agent is at least one selected from the group consisting of nonionic dispersing agents, anionic dispersing agents and cationic dispersing agents.

(104) An emulsion, according to said (103), wherein the zeta potential of the disarranged fibers is in a range from −5 to +5 mV, and the dispersing agent is a nonionic dispersing agent.

(105) An emulsion, according to said (103), wherein the zeta potential of the disarranged fibers is −100 mV to less than −5 mV, and the dispersing agent is an anionic dispersing agent.

(106) An emulsion, according to said (103), wherein the zeta potential of the disarranged fibers is more than +5 mV to 100 mV, and the dispersing agent is a cationic dispersing agent.

(107) An emulsion, according to said (101), wherein the molecular weight of the dispersing agent is 1000 to 50000.

(108) A gel comprising disarranged fibers made of a thermoplastic polymer, and of 1 to 500 nm in the number average single fiber diameter and 60% or more in the sum Pa of single fiber ratios, and a solvent.

(109) A gel comprising disarranged fibers made of a thermoplastic polymer, and of 1 to 200 nm in the number average single fiber diameter and 60% or more in the sum Pa of single fiber ratios, and a solvent.

(110) A gel, according to said (108) or (109), wherein the index Pb of extremal coefficient of the single fiber diameters expressing the rate of the fibers falling within a range of plus and minus 15 nm from the number average single fiber diameter defined as the median is 50% or more.

(111) A gel, according to said (108), wherein the solvent is at least one selected from the group consisting of water, oils and organic solvents.

(112) A gel, according to said (108) or (109), wherein the freeness of the disarranged fibers is 350 or less.

(113) A gel, according to said (108), wherein the content of the disarranged fibers is 30 wt % or less.

(114) A gel, according to said (108), wherein the disarranged fibers are short fibers with a fiber length of 5 mm or less.

(115) A gel, according to said (108), wherein the thermoplastic polymer is at least one selected from the group consisting of polyesters, polyamides, polyolefins, polyphenylene sulfide, phenol resins, polyacrylonitrile, polyvinyl alcohol, polysulfones, polyurethanes, fluorine-based polymers and their derivatives.

(116) A gel, according to said (108), which further contains a dispersing agent.

(117) A gel, according to said (116), wherein the content of the dispersing agent is 0.00001 to 20 wt %.

(118) A gel, according to said (116), wherein the dispersing agent is at least one selected from the group consisting of nonionic dispersing agents, anionic dispersing agents and cationic dispersing agents.

(119) A gel, according to said (118), wherein the zeta potential of the disarranged fibers is in a range from −5 to +5 mV, and the dispersing agent is a nonionic dispersing agent.

(120) A gel, according to said (118), wherein the zeta potential of the disarranged fibers is −100 mV to less than −5 mV, and the dispersing agent is an anionic dispersing agent.

(121) A gel, according to said (118), wherein the zeta potential of the disarranged fibers is more than +5 mV to 100 mV, and the dispersing agent is a cationic dispersing agent.

(122) A gel, according to said (116), wherein the molecular weight of the dispersing agent is 1000 to 50000.

(123) A cosmetic comprising the compound solution, emulsion or gel as set forth in said (1).

(124) A cosmetic comprising the emulsion as set forth in said (93).

(125) A cosmetic comprising the gel as set forth in said (108).

(126) A paint comprising the compound solution as set forth in said (1).

(127) A paint comprising the emulsion as set forth in said (93).

(128) A paint comprising the gel as set forth in said (108).

(129) A method for producing the compound solution as set forth in said (1), comprising the step of directly beating a fiber aggregate in at least one selected from the group consisting of water, oils and organic solvents.

(130) A method for producing the emulsion as set forth in said (93), comprising the step of directly beating a fiber aggregate in at least one selected from the group consisting of water, oils and organic solvents.

(131) A method for producing the gel as set forth in said (108), comprising the step of directly beating a fiber aggregate in at least one selected from the group consisting of water, oils and organic solvents.

(132) A nanofiber synthetic paper comprising disarranged nanofibers of a thermoplastic polymer of 1 to 500 nm in the number average single fiber diameter and 60% or more in the sum Pa of single fiber ratios.

(133) A nanofiber synthetic paper, according to said (58), which comprises disarranged nanofibers of a thermoplastic polymer of 1 to 200 nm in the number average single fiber diameter and 60% or more in the sum Pa of single fiber ratios.

(134) A nanofiber synthetic paper, according to said (132) or (133), wherein the index Pb of extremal coefficient of the single fiber diameters expressing the rate of the fibers falling within a range of plus and minus 15 nm from the number average single fiber diameter defined as the median is 50% or more.

(135) A nanofiber synthetic paper, according to said (132) or (133), wherein the freeness of the disarranged nanofibers is 350 or less.

(136) A nanofiber synthetic paper, according to said (132), which has a weight per unit area of 50 g/m² or less.

(137) A nanofiber synthetic paper, according to said (132), which has a thickness of 10 μm or more.

(138) A nanofiber synthetic paper, according to said (132), which has a density of 0.3 g/cm³ or less.

(139) A nanofiber synthetic paper, according to said (132), which has a number average pore area of 1 μm² or less.

(140) A nanofiber synthetic paper, according to said (132) or (133), which has an air permeability of 30 cc/cm²/sec or less.

(141) A nanofiber synthetic paper, according to said (132), wherein the number of holes with a diameter of 50 μm or more passing through from the front side to the reverse side of the synthetic paper is 0 to 1000 holes/cm².

(142) A nanofiber synthetic paper, according to said (132) or (133), which has a surface smoothness of 300 seconds or more.

(143) A nanofiber synthetic paper, according to said (132), wherein the thermoplastic polymer constituting the disarranged nanofibers has a melting point of 165° C. or higher.

(144) A nanofiber synthetic paper, according to said (132), wherein the thermoplastic polymer constituting the disarranged nanofibers is at least one selected from the group consisting of polyesters, polyamides, polyolefins, polyphenylene sulfide, phenol resins, polyacrylonitrile, polyvinyl alcohol, polysulfones, polyurethanes, fluorine-based polymers and their derivatives.

(145) A nanofiber synthetic paper, according to said (132), which further contains at least 5 wt % or more of other fibers with a number average single fiber diameter of 1 μm or more.

(146) A nanofiber synthetic paper, according to said (132), which further contains other fibers with a number average single fiber diameter of 1 μm or more, and 3 wt % or less of the disarranged nanofibers.

(147) A nanofiber synthetic paper, according to said (132), wherein the disarranged nanofibers are laminated on a substrate.

(148) A nanofiber synthetic paper, according to said (147), wherein the substrate is selected from a woven fabric, knitted fabric, nonwoven fabric and foam.

(149) A compound synthetic paper comprising the nanofiber synthetic paper as set forth in said (132).

(150) A molded synthetic paper comprising the nanofiber synthetic paper as set forth in said (132).

(151) A filter comprising the nanofiber synthetic paper as set forth in said (132).

(152) A separator comprising the nanofiber synthetic paper as set forth in said (132).

(153) An abrasive comprising the nanofiber synthetic paper as set forth in said (132).

(154) A medical product comprising the nanofiber synthetic paper as set forth in said (132).

(155) A circuit board comprising the nanofiber synthetic paper as set forth in said (132).

(156) A method for producing a nanofiber synthetic paper by forming a paper sheet from a dispersion of beaten short nanofibers, characterized in that the paper sheet is formed without using a binder.

(157) A method for producing a nanofiber synthetic paper, characterized in that other fibers with a number average single fiber diameter of 1 μm or more are processed to form a paper sheet using disarranged nanofibers as a binder.

Figure 1:
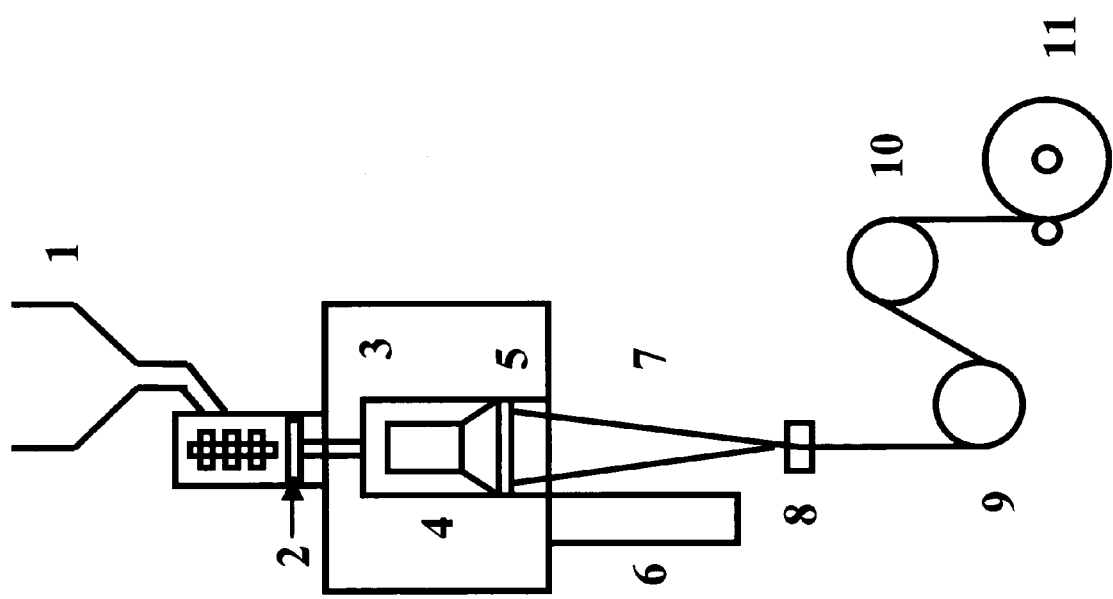
FIG. 1 is a schematic drawing showing a spinning machine for "polymer alloy fibers" used as the raw fibers of nanofibers.

| Meanings of Symbols | |
|---|---|
| 1: | hopper |
| 2: | melting portion |
| 3: | spin block |
| 4: | spinning pack |
| 5: | spinneret |
| 6: | chimney |
| 7: | filaments |
| 8: | filament-collecting finishing guide |
| 9: | first take-up roller |
| 10: | second take-up roller |
| 11: | winder |
| 12: | sea component-removing tank |
| 13: | treatment liquid plumbing |
| 14: | pump |
| 15: | upper bar |
| 16: | lower bar |
| 17: | treatment liquid hole |
| 18: | hank-like tow |
| 19: | sea component-removing liquid |

DETAILED DESCRIPTION

According to the present invention, in the recent fields of cosmetics, medical articles, etc., since nanofibers are mixed in a compound solution, emulsion or gel respectively, microparticles and nanoparticles such as precious metal particles, metal oxide particles or polymer particles of 1 μm or less can be homogeneously dispersed and the dispersion can be stabilized for a long period of time.

Furthermore, if a cosmetic product containing conventional fibers with a diameter of more than several micrometers is used, the user feels gritty. So, such fibers cannot be practically used in cosmetics. However, our nanofibers are thinner than the wrinkle creases of the skin surface and have good affinity with the skin, being able to give a soft and natural touch to the skin. The nanofiber's contained in a cosmetic product can keep the cosmetic product good in slipperiness, water retention, moisture retention, smooth spreadability and packing property and can keep it lasting longer, being able to provide functions unavailable from the conventional fibers. Therefore, for using the features of nanofibers such as very small thickness and very large specific surface area, the nanofibers of this invention can be applied to numerous cosmetic items such as toilet waters, lotions, liquid foundations, shampoos, rinses, emulsions, cold creams, cleansing creams, shaving creams, hair creams, pack gels, ointment gels, hairdressing gels, face washing gels, soap gels and pack materials.

Furthermore, such effects as dispersibility, homogeneity and storage capability of nanofibers are effective not merely to cosmetics but also to the materials of medical field such as ointments, wet compresses, materials of cell culture and materials of albumin adsorption, the materials of electronic material and apparatus field such as materials of electrolytes for batteries, materials of catalyst carriers for fuel cells, materials of catalyst carriers for chemical filters and materials for adsorbing hazardous gases, the materials of architectural material field such as paints, adhesives and wall coating materials respectively containing various fillers and pigments, the materials of industrial material field such as purifying filters and carriers of fine particles such as activated carbon and titanium oxide for purifying filters, coloring materials for pictures, etc.

Furthermore, in the fields where the conventional ordinary synthetic fibers and ultrafine fibers could not meet requirements, our compound solutions, emulsions and gels present surface activities and allow chemical surface interactions at nanometer level, such as capabilities to adsorb or absorb various substances (such as fine particles, chemical substances, proteins, and pathogenic microbes), ecological adaptability and compatibility, etc.

On the other hand, more highly accurate products are required in the fields of filters (such as air filters, chemical filters and water purifying filters), mask filters, battery separators, blood filter materials of medical field, materials of extrasomatic circulation columns, materials of cell culture, insulating materials and electronic substrates as electronic materials, toilet paper, wiping paper, decorative paper for furniture, wall paper, paper for high quality printing, design paper, and high image quality printing paper. In these fields, the conventional ultrafine fibers and the nanofibers obtained by electrospinning are not sufficient in the uniformity of fiber diameter or cannot be accurately controlled in pore size or in the weight per unit area, thickness or density of the nonwoven fabric produced from the fibers. Moreover, according to the electrospinning method, a nonwoven fabric with a wide width cannot be efficiently produced due to such problems as the safety of working environment due to the evaporation of the solvent and the recovery of the solvent. If our nanofibers are used, highly accurate materials can be designed, and practical synthetic papers can be provided. Furthermore, we can meet the needs in the fields where the conventional synthetic fibers and ultrafine fibers could not meet such needs and where interactions of nanometer level such as the capability to adsorb or absorb various substances (fine particles, chemical substances, proteins, etc.) and ecological adaptability and Compatibility are needed. The synthetic papers of this invention can solve the conventional problems.

Examples of the thermoplastic polymer constituting the disarranged fibers include polyesters, polyamides, polyolefins, polyphenylene sulfide (PPS), etc. The polyesters include polyethylene terephthalate (PET), polytrimethylene terephthalate (PTT), polybutylene terephthalate (PBT), polylactic acid (PLA), etc. Furthermore, the polyamides include nylon 6 (N6), nylon 66 (N66), nylon 11 (N11), etc. Moreover, the polyolefins include polyethylene (PE), polypropylene (PP), polystyrene (PS), etc. In addition to the aforesaid thermoplastic polymers, phenol resins, polyacrylonitrile (PAN), polyvinyl alcohol (PVA), polysulfones, fluorine-based polymers and their derivatives can of course be used.

Among these polymers, in view of heat resistance, those with a melting point of 165° C. or higher are preferred. More preferred are polymers with a high melting point among the polycondensation polymers typified by polyesters and polyamides. For example, PP has a melting point of 165° C.; PLA, 170° C.;. N6, 220° C.; and PET, 255° C. Furthermore, any of these polymers can also contain compounding ingredients such as fine particles, flame retarder and antistatic agent. Moreover, another ingredient can also be copolymerized to such an extent that the nature of the polymer is not impaired. Still furthermore, in view of easy melt spinning, a polymer with a melting point of 300° C. or lower is preferred.

Especially polyamides typified by N6 and N66 are excellent in water absorbability and water retention, and if nanofibers of a polyamide are contained in the compound solution, emulsion or gel to use those properties, the obtained composition can be suitably used for cosmetic application, etc.

Furthermore, PPS shows excellent heat resistance and chemical reagent resistance and has low moisture absorbability. So, the synthetic paper produced from it is also excellent in dimensional stability, and can be suitably used for such applications as insulating paper and circuit board in the electronic information field.

The disarranged fibers refer to nanofibers, the number average diameter of which as single fibers (number average single fiber diameter) is in a range from 1 to 500 nm. The disarranged fibers are in a mode in which single fibers are dispersed. Furthermore, the disarranged fibers are not limited in length or sectional form, if they are merely formed like fibers. In this invention, the average value and irregularity of the single fiber diameters of nanofibers are important. It is important that the nanofibers are homogeneously dispersed in the compound solution, emulsion, gel or synthetic paper, and especially it is important that the number average single fiber diameter in a compound solution, emulsion or gel is 1 to 500 nm, to improve the long-term stability lest the nanofibers should cohere to each other or settle with the lapse of time. A preferred range is 1 to 200 nm, and a more preferred range is 1 to 150 nm. A further more preferred range is 1 to 100 nm. Especially in the case where the synthetic paper is used as a filter, high performance and highly efficient collection are required as properties, and in the case where it is used as a separator or the like, high liquid impermeability is required as a property. So, it is desirable that the single fiber diameter of nanofibers is smaller, and in this case, it is preferred that the number average single fiber diameter is 1 to 150 nm. A more preferred range is 1 to 100 nm.

The number average single fiber diameter is evaluated by "H. SEM observation of nanofibers" and "I. Number average single fiber diameter φm of nanofibers" described as measuring methods for the examples described later, and the irregularity in the single fiber diameters is expressed by "H. SEM observation of nanofibers", "J. Evaluation of the sum Pa of single fiber ratios of nanofibers" and "K. Evaluation of the index Pb of extremal coefficient of single fiber diameters of nanofibers".

For measuring the number average single fiber diameter, nanofibers are sampled from a compound solution, emulsion, gel or synthetic paper, and the surfaces of the sampled nanofibers are observed using a transmission electron microscope (TEM) or scanning electron microscope (SEM). The diameters of 30 single fibers sampled at random from one surface are measured, and this sampling is performed 10 times. Thus, the simple average value is obtained from the diameters of 300 single fibers in total. This is called the "number average single fiber diameter φm" in this invention. In this invention, it is important that the number average single fiber diameter is 1 to 500 nm. This small diameter corresponds to $1/100$ to $1/100000$ of the diameters of conventional ultrafine fibers obtained, for example, by the islands-in-sea multi-component spinning. Because of it, the dispersibility of nanofibers in the compound solution, emulsion or gel of this invention can be remarkably enhanced, and furthermore, the synthetic paper obtained is better in evenness, larger in specific surface area and higher in performance than the synthetic papers obtained by using conventional ultrafine fibers.

The irregularity in the single fiber diameters of nanofibers is evaluated as described below. To construct a histogram from the single fiber diameters obtained as described above, diameters φ of single fibers are classified into a desired number (n) of divisions, and the average value of the values at both the ends of each division is expressed as φi. The frequency fi of nanofibers in each diameter division φi (i=1 to n) is counted to construct the histogram. For classifying into a desired number of divisions, for example, in the case where the number average single fiber diameter φm is 500 nm or less, the diameter increment of each division can be 1 nm to 10 nm, and diameters can be classified into 10 to 100 divisions (n). {For comparison, in the case where the number average single fiber diameter φm is more than 500 nm, the diameter increment of each division can be $1/10$ or less of the number average single fiber diameter φm, and diameters can be classified into about 10 to about 100 divisions (n)}.

The "sum Pa of single fiber ratios" and the "index Pb of extremal coefficient" used for evaluating the irregularity of single fiber diameters will be described below.

The frequency fi of the nanofibers belonging to the average single fiber diameter φi of each division is counted and divided by N to obtain the ratio Pi of the average single fiber diameter, and the individual Pi values of fi/N of division number 1 to division number r in the range from 1 to 500 nm are simply added to obtain Pa.

$$N=\Sigma fi (i=1 \text{ to } n) \quad (2)$$

$$Pa=\Sigma(fi/N)(i=1 \text{ to } r) \quad (3)$$

Particularly it is only required to add the individual fi/N values of division number 1 to division number r in the range from 1 to 500 nm. In this invention, it is important that Pa is 60% or more. Preferred is 65% or more, and more preferred is 70% or more. A larger Pa value means that the ratio of the nanofibers in the sense of this invention is larger while the ratio of the fibers with larger single fiber diameters is smaller.

If Pa is as specified above, the nanofibers can sufficiently exhibit their functions and can also be good in product quality stability.

Meanwhile, the index Pb of extremal coefficient of single fiber diameters indicates the degree to which single fibers with diameters close to the average diameter are concentrated. The frequencies fi of respective average diameters φi obtained as described above are used to construct a histogram of "frequencies fj for respective divisions of square values χi of average single fiber diameters φi". Then, a table of "values Pj obtained by totalizing said frequencies fj" for χi is prepared beforehand.

$$Pj=\Sigma(fj/N)(j=1 \text{ to } n) \quad (4)$$

Since the square value χi of a single fiber diameter φi is proportional to the weight of the fiber (cylindrical), the distribution corresponds to the distribution for dtex (fineness) as can be seen from formula (1). The approximate function Q (fourth to sixth degree polynomial function of χi) of this "total frequency Pj" for χi is prepared using the Excel (trade name) produced by Microsoft. Subsequently if the square value of the sum obtained by adding 15 nm to the number average single fiber diameter φm defined as the median is χa and the square value of the difference obtained by subtracting 15 nm from φm is χb, then the index Pb of extremal coefficient can be obtained from the following formula.

$$Pb=Q(\chi a)-Q(\chi b) \quad (5)$$

It is preferred that the index Pb of extremal coefficient of the single fiber diameters expressing the rate of the fibers falling within a range of plus and minus 15 nm from the number average single fiber diameter defined as the median is 50% or more. More preferred is 60% or more, and further more preferred is 70% or more. This means the irregularity of single fiber diameters, i.e., the degree to which single fibers with diameters close to the number average single fiber diameter are concentrated. A higher Pb values means that the irregularity of single fiber diameters is smaller. The actual methods for measuring the number average single fiber diameter φm, the sum Pa of single fiber ratios and the index Pb of extremal coefficient of single fiber diameters are explained in the examples described later.

The disarranged nanofibers can be used to make the intended compound solution, emulsion and gel. This can be achieved only when the aforesaid nanofibers are used. For example, since the nanofibers obtained by the electrospinning can be usually collected only in the form of a nonwoven fabric, there is no idea of homogeneously dispersing the obtained nanofibers into a solvent, and it is difficult to do so. Actually there has been no case of dispersing the nanofibers into a solvent. On the other hand, in this invention, a melt spinning method with high productivity is used to obtain polymer alloy fibers, and the sea component is removed from them to obtain an aggregate of nanofibers. They are further shortened, beaten and dispersed to obtain disarranged nanofibers. Therefore, the compound solution, emulsion and gel as described above could be efficiently produced for the first time.

The nanofiber compound solution, emulsion or gel includes disarranged nanofibers and a solvent or gel. The compound solution, emulsion or gel of this invention refers to a liquid or solid in which nanofibers, or nanofibers and another chemical substance are mixed in a solvent or gel.

In the compound solution, the disarranged nanofibers are dispersed in a solvent at a relatively low concentration. So, the compound solution has a relatively low viscosity and is highly flowable. Meanwhile, a substance having the disarranged nanofibers in a solvent or gel at a relatively high concentration, to have a relatively high viscosity and low flowability, is defined as a gel. Furthermore, a compound solution formed as an emulsion, having disarranged nanofibers dispersed in the emulsion at a relatively low concentration, is defined as an emulsion.

The solvent or gel referred to here not only dissolves the compounding ingredients other than the nanofibers in the compound solution, emulsion or gel but also functions as the dispersion medium of nanofibers. The solvent can be an adequate combination of water and/or an oil and/or an organic solvent (including an emulsion). Examples of the oil include natural oils such as linseed oil, corn oil, olive oil, sunflower oil, rapeseed oil, sesame oil, soybean oil, cacao oil, coconut oil, palm oil and haze wax, paraffin, vaseline, ceresine, liquid paraffin, squalane, wax, higher fatty acids, silicone oil, crosslinked silicone oil, etc. Any one of them can be used or two or more of them can also be used in combination. Examples of the organic solvent include alcohols, esters, glycols, glycerols, ketones, ethers, amines, lower fatty acids such as lactic acid and butyric acid, pyridine, tetrahydrofuran, furfuryl alcohol, acetonitriles, methyl lactate, ethyl lactate, etc. Any one of them can be used or two or more of them can also be used in combination.

It is preferred in view of higher dispersibility in the solvent that the disarranged nanofibers with a single fiber diameter of 1 to 500 nm used in this invention have a freeness of 350 or less. Furthermore, if the freeness is in this range, the nanofibers are good in papermaking properties, and can be homogeneously dispersed in the synthetic paper. So, even if the synthetic paper has a low weight per unit area, it can have high performance with good evenness. A more preferred freeness is 200 or less, and a further more preferred freeness is 100 or less. It is preferred that the lower limit of the freeness is 5 or more.

The nanofibers with a single fiber diameter of 1 to 500 nm are compared with the conventional synthetic fibers hereunder. For the two types of conventional fibers, i.e., fibers with a diameter of 10 μm or more (hereinafter called the ordinary fibers) and fibers with a diameter of more than 0.5 μm to 10 μm (hereinafter called the ultrafine fibers), and for the fibers used in this invention with a diameter of 0.5 μm (500 nm) or less (nanofibers A and B), Table 1 shows typical fiber diameters of the respective types of fibers.

Between the usually often used fineness (dtex) and the single fiber diameter $\phi$ (μm), the following formula (1) holds.

$$\phi = 10 \times (4 \times dtex/\pi/\rho)^{1/2} \quad (1)$$

where dtex is the thickness of a fiber, at which the fiber with a length of 10000 m weighs 1 g (JIS L 0101).

If the specific gravity is assumed to be 1.14 (corresponding to nylon 6), the single fiber diameter $\phi$ (μm) can be obtained from the following formula.

$$\phi n6 = 10.6 \times (dtex)^{1/2}$$

The ordinary fibers and the ultrafine fibers as conventional fibers (hereinafter these two types of fibers are generally called the conventional fibers), and the nanofibers A with a diameter of 200 nm and the nanofibers B with a diameter of 60 nm as fibers with their diameter kept in a range of 1 to 500 nm used in this invention are shown in Table 1. The fiber diameter referred to here is the number average single fiber diameter $\phi$m defined by said formula (1), and as the measuring method is described for the examples given later, the average single fiber diameter is measured using a transmission electron microscope (TEM) or scanning electron microscope (SEM).

Aqueous solutions and toilet waters respectively containing 0.01 wt % of any of various types of fibers cut to 2 mm were prepared, and the number and specific surface area of the fibers contained per 1 ml of each of the aqueous solutions and toilet waters are shown in Table 1. It can be seen that 160 ordinary fibers and 16,000 ultrafine fibers are contained respectively. Compared with the conventional fibers, 1.6 million nanofibers A and 18 million finer nanofibers B are contained respectively, to show that very large numbers of fibers are contained. The nanofibers A and B are very large also in specific surface area and aspect ratio.

If the nanofiber compound solution, emulsion and gel of this invention having such features as a very small fiber diameter and a large specific surface area are used respectively alone or together in combination, the following various cosmetics can be obtained. Particular examples of the cosmetics include toilet waters (such as general toilet waters, colognes, after shave lotions and sunscreen lotions), cream-emulsions (such as generally cosmetic milky lotions, after shave creams, cleansing creams, cold creams, shaving creams, hand creams and sunscreen creams), foundations (such as liquid foundations, creamy foundations and solid foundations), face powders (such as creamy powders, solid powders, face powders, baby powders and body powders), hair cosmetics (such as hair oils, wave set lotions, stick pomades, hair creams, hair tonics, hair liquids, hair sprays and pomades), cleansing cosmetics (such as shampoos, rinses, cosmetic soaps and make-up removers), lip cosmetics (such as lipsticks and lip creams), packs, point make-ups (such as eye shadows, eyeliners, eye creams, rouges, mascaras and eyebrow pencils), nail enamels, tooth pastes, ointment gels, etc. The nanofiber compound solution, emulsion and gel can be used selectively or in combination to suit respective applications and purposes.

In the meantime, in a toilet water or emulsion containing oil particles of micron level or containing a precious metal or any other compounding ingredient as particles of several nanometers to hundreds of nanometers, even if any of various dispersing agents is added, the particles are very likely to cohere to each other, and it has been difficult to keep very fine particles homogeneously dispersed. Furthermore, even if the particles are once dispersed, the homogeneity of dispersion may be lost after storing for a long period of time, and segregation or sedimentation due to cohesion may occur. If segregation occurs once, it is difficult to re-disperse the fine particles as in the initial state even if the bottle is shaken for stirring the contained dispersion. This phenomenon occurs not only with a compound solution but also with an emulsion or gel. So, in the cosmetic field, it has been desired to homogeneously disperse fine particles and to stabilize the dispersion so that the cosmetic product can be stored for a long period of time.

In this regard, if the nanofiber compound solution, emulsion or gel is used, the above problem can be solved. The nanofiber compound solution contains 18 million nanofibers per 1 ml of the solution as shown in Table 1, and the specific surface area is also very large. Furthermore, if the nanofibers are cut fibers with a fiber length of 2 mm, the ratio of fiber length (L)/fiber diameter (D), i.e., aspect ratio is 10000 to 33000 as shown in Table 1. These fibers are very long. So, if these nanofibers are added into a compound solution, emulsion or gel, the above-mentioned fine particles of micron level, nanoparticles or the like can be uniformly carried on the surfaces of the nanofibers. In this way, fine particles of a precious metal with a large specific gravity or fine particles of various compounding ingredients such as UV-shielding reagent can be dispersed scatteringly without causing cohesion or can be prevented from cohering to each other. Furthermore, if the narrow and long nanofibers act on the fine particles lightly cohering to each other to form flocks or clusters in the solution, the particles are stirred or rubbed to destroy the flocks or clusters, for allowing homogenous dispersion.

Moreover, as many as 18 million narrow and long nanofibers exist per 1 ml of the solution, and they are dispersed scatteringly in the solution. This means that the nanofibers are spread to very finely partition the space in the compound solution, emulsion or gel, and that the fine particles carried on the surfaces of the nanofibers are also homogeneously dispersed. Furthermore, the dispersed nanofibers are entangled and joined with each other, to form a network space of nanofibers. Since this network state remains very stable for a long period of time, oil droplets, very fine liquid particles of an emulsion, fine particles of a precious metal with a large specific gravity, or fine particles of various compounding ingredients such as UV-shielding reagent can be stored stably for a long period of time without allowing them to cohere or settle.

It is difficult to stabilize the dispersion of some emulsions and compounding ingredients consisting of fine particles merely by using an ordinary dispersing agent or by mere pH adjustment, and in such cases, it is very effective to use nanofibers. With regard to the nanofiber concentration in the nanofiber compound solution, emulsion or gel of this invention, it is preferred that the nanofiber concentration of a gel is 30 wt % or less. A more preferred range is more than 1 wt % to 5 wt %. Furthermore, it is preferred that the nanofiber concentration of a compound solution or emulsion is 5 wt % or less. A more preferred range is 0.0001 to 1 wt %, and a further more preferred range is 0.003 to 0.3 wt %. As shown in Table 1, in the case of nanofibers with a diameter of 60 nm (0.06 µm), even if the nanofiber concentration is 0.01 wt %, as many as 18 million nanofibers are contained. So, even at such a low concentration, the nanofibers are effective for enhancing dispersibility and for ensuring long-term storage stabilization. Of course, the nanofiber concentration can be adjusted considering the fine particles to be dispersed, fine particle concentration, storage period, the influence of other compounding ingredients, etc.

It is preferred that the nanofibers with a number average single fiber diameter of 1 to 500 nm used in this invention are short fibers with a fiber length of 20 mm or less. If the fiber length is more than 20 mm, the nanofibers may be entangled with each other excessively, and the dispersibility may decline as the case may be. Therefore, to keep the nanofibers well dispersed in the nanofiber compound solution, emulsion or gel, it is preferred that the nanofibers have a length of 0.05 to 2 mm. Furthermore, in the case where nanofibers are applied to a gel, it is preferred that the nanofibers have a length of 0.2 to 1 mm, and in the case where nanofibers are applied to an emulsion, it is preferred that the nanofibers have a length of 0.05 to 0.8 mm. Especially in the case of a highly viscous oil or gel, since nanofibers are likely to cohere with each other, it is preferred to add them little by little. Furthermore, in the case of a gel, it is preferred to use a mixer with high shearing force such as a kneader or twin-screw mixer for mixing.

On the other hand, it is preferred in view of papermaking properties that the adequate fiber length of the short nanofibers in the nanofiber synthetic paper of this invention is 0.1 to 20 mm. A more preferred range is 0.1 to 5 mm, and a further more preferred range is 0.2 to 1 mm.

Moreover, as the nanofibers, it is preferred that the ratio (L/D) of the fiber length L (mm) to the number average diameter D (mm) is 100 to 50000. If L/D is kept in this range, the dispersibility of nanofibers in the compound solution, emulsion or gel can be enhanced. Furthermore, in the synthetic paper of this invention, if L/D is kept in the aforesaid range, a sheet having single nanofibers homogeneously dispersed in the synthetic paper can be obtained, and in addition, since the nanofibers can be more entangled with and adhesive to each other, the paper force of the synthetic paper can be enhanced. In the case of compound solution, emulsion or gel, a more preferred range is 1000 to 20000, and a further more preferred range is 500 to 2000. In the case of synthetic paper, it is more preferred that L/D is 1000 to 35000, and a further more preferred range is 3000 to 20000.

The compound solution especially containing the nanofibers is good in transparency. The transparency is evaluated according to the measuring method of "P. Transparency" described for the examples given later. For example as in Example 6, the rate of light transparency of a nanofiber compound solution containing 0.01 wt % of nanofibers with a fiber length of 2 mm is 51%. So, the solution has excellent transparency. In this case, though the fiber diameter of the nanofibers is 60 nm, being smaller than the wavelength of light (400 to 700 nm), the fiber length is as very large as 2 mm (2000000 nm). Furthermore, as shown in Table 1, even though the number of nanofibers existing per 1 ml of the solution is as very large as 18 million, the transparency is very good. This is considered to be attributable to the effect of nanofibers homogeneously dispersed as single fibers. To further enhance the transparency, it is preferred that the fiber concentration of the solution is 0.0001 to 0.01 wt %, and that the fiber length is as short as 0.05 to 0.8 mm. A more preferred range is 0.05 to 0.2 mm. If the nanofiber concentration is too low or if the fiber length is too short, the effect of stabilization by the dispersion of nanofibers declines. Moreover, for improving the rate of light transparency, it is also effective to use an adequate dispersing agent. When 0.1 wt % of an anionic dispersing agent was added to a N6 nanofiber compound solution, the rate of light transparency rose to 63% (Example 9 given later). Furthermore, since the nanofibers have a fiber diameter smaller than the wavelength of light, it is theoretically transparent in the diameter direction, but since the fiber length is very long compared with the wavelength of light, transparency is considerably impaired by the influence of overlapping fibers, suspected adhesion, clusters, flocks, etc., and irregular reflection is also likely to occur. To prevent irregular reflection and to improve transparency, it is also preferred to coat or wet the surfaces of nanofibers with a silicone-based polymer, fluorine-based polymer, urethane-based polymer, acrylic polymer or the like for adjusting the refractive index.

Furthermore, the polymer used to constitute the nanofibers is selected for each application or purpose of use. Especially for cosmetic and medical applications, a polymer incapable of stimulating the skin or human body is preferred. Particularly polyamides, polyolefins, polyesters, fluorine-based polymers, polyvinyl alcohol (PVA) and their derivatives are preferred. For cosmetics, from the view point of imparting moisture retention and water retention, polyamides, polylactic acid, PVA and their derivatives are preferred. For battery separators and industrial filters, polyolefins, fluorine-based polymers and their derivatives are preferred since they are good in chemical reagent resistance. For architectural application such as paints, wall materials and coating materials, polyurethanes, polyesters, polyamides and their derivatives are preferred. Furthermore, depending on the application or purpose of use, two or more polymers can also be adequately selected.

The flexibility and touch of nanofibers will be described below.

The flexibility can be measured in reference to the quantity of flexure of the material. A softer material is larger in the quantity of flexure. It can be estimated from the following formula (6) relating to the bending of a material in the JSME Mechanical Engineers' Handbook (pA4-28, 25, The Japan Society of Mechanical Engineers, 1963). In this formula, v is the quantity of flexure, and it becomes large in inverse proportion to the $4^{th}$ power of diameter D (w ... load, E ... elastic modulus of the material).

$$v=4 \times w \times l^3/(3 \times E \times D^4) \qquad (6)$$

The flexibility of the nanofibers can be compared with that of the conventional fibers as described below. The softness increases in inverse proportion to the $4^{th}$ power of the fiber diameter. For example, if the diameter of ultrafine fibers is 1/10 of that of ordinary fibers, v is 10000 times larger. So, the flexibility of ultrafine fibers corresponds to 10000 times the flexibility of ordinary fibers. The diameter of nanofibers is 1/10 to 1/100 of that of ultrafine fibers. So, the nanofibers are 10000 to 100 million times softer than the ultrafine fibers. For example, the fibers taken out of an aqueous solution are likely to be entangled with each other for forming a network, since if fibers are thinner, they increase in number. So, actually the flexibility cannot be as estimated by calculation from the above formula (6) expressing the quantity of flexure of each fiber. However, whenever the diameter becomes 1/10, the flexibility of the fibers becomes very higher. Table 2 shows the rigidity values of respective types of fibers as an indicator of flexibility. In this table, with the inverse number of the quantity of flexure of ordinary fibers as 1, the rigidity values of the respective types of fibers are relatively compared. A smaller rigidity value shows a larger quantity of flexure, i.e., higher flexibility.

If ordinary fibers are dispersed in a cosmetic product and it is applied to the skin, the ordinary fibers rigid and hard to bend stimulate the skin and make the user feel very gritty. So, the cosmetic product is not suitable for the skin at all. In the case of ultrafine fibers, the flexibility is improved compared with the ordinary fibers, but even so, during or after coating, the stress of coating is still felt strongly. The reason is considered to be as explained below. The widths of wrinkles on the skin are 1 micrometer to tens of micrometers, while the diameter of usual ultrafine fibers is several micrometers. So, theoretically the fibers can fit into the wrinkles, but actually it is estimated that the fibers cohere to each other to grow larger and are highly rigid and so that the fibers cannot be fortunately deformed along the wrinkles, only to float on the surface of the skin.

On the other hand, the diameter of the nanofibers is 0.5 μm (500 nm) or less and considerably smaller than the width of wrinkles, and in addition, the fibers are extraordinarily excellently flexible. So, they can easily go into the wrinkles. Furthermore, since the nanofibers are flexible, it can be considered that they little stimulate the skin and give an acceptably smooth and moist touch. Moreover, the nanofibers have a large specific surface area and excellent water retention and moisture retention. So, if the nanofibers contain water, the effects are further improved, and the nanofibers can be very highly adapted to the skin. For example, when simple water containing nanofibers (toilet water or emulsion) was used to merely wash the face, the skin became soft and smooth, and when it was applied, it little made the users feel the stress of coating (see Examples 10 to 16 given later). However, when a toilet water containing the conventional ordinary fibers with a diameter of tens of micrometers was used, the users felt gritty on the skin, and felt the stress of coating very badly (see Comparative Examples 7 and 8 given later). Furthermore, even the conventional ultrafine fibers with a diameter of 2 μm, the fibers were merely placed on the skin, and the touch was bad. Moreover with regard to flexibility, the fibers were very hard compared with nanofibers, and the users felt the stress of coating significantly.

The moisture retention and water retention of nanofibers will be described below.

The nanofibers are excellent in moisture retention and water retention, since they have a very large specific surface area compared with the conventional fibers. Moisture retention can be evaluated by placing a certain amount of fibers in a box kept at a low humidity and measuring the weight loss of the fibers. A larger weight loss rate (drying rate) means lower moisture retention. The actual measuring method is as described in "M. Index of moisture retention (ΔWR10)" as an evaluation method for the examples given later. When the conventional fibers were compared with the nanofibers of this invention, the index of moisture retention of the conventional ordinary fibers was 39%/10 min (Comparative Example 1), and that of the conventional ultrafine fibers was 29%/10 min (Comparative Example 3). On the contrary, the index of moisture retention of the nanofibers was as low as 13%/10 min (Example 1). It was found that the moisture retention of the nanofibers was about 2 to 3 times better than that of the conventional fibers. The water retention refers to the water content of the fibers sufficiently impregnated with water and subsequently lightly wringed. To keep the wringing level constant, the dehydration conditions of the centrifuge are kept constant. The actual measuring method is as described in "N. Index of water retention (WI)" as an evaluation method for the examples given later. When the conventional fibers were compared with the nanofibers of this invention, the index of water retention of the conventional ordinary fibers was 235% (Comparative Example 1) and that of the conventional ultrafine fibers was 509% (Comparative Example 3). On the contrary, the index of water retention of the nanofibers was 1608% (Example 1). It was found that the water retention of the nanofibers was as very large as more than 3 times that of the conventional fibers. Meanwhile, the duration of moisture retention is attributable to both the initially retained amount of water (water retention) and to the resistance to drying (moisture retention), and since the nanofibers are more excellent than the conventional fibers in both the properties, they are also superior in the duration of moisture retention. They have not only a direct effect of retaining the moisture of the cosmetic product but also a drying prevention effect and a sustained release effect for the other moisture retaining ingredient used instead of water, solvent, aromatic component, etc. To further improve the effects of moisture retention and water retention, it is preferred to keep the fiber concentration rather larger in a range of 0.01 to 1 wt % in the solution. Furthermore, it is also preferred that the fiber diameter is 120 nm or less. More preferred is 80 nm or less. Moreover, it is also preferred to use also another natural moisture or water retaining agent or an organic or inorganic moisture or water retaining agent together.

In addition to the above, as an application of a moisture or water retaining agent using the nanofibers, there is a gel containing the nanofibers, as a beauty care pack. The following two methods are available for obtaining the pack: a method in which a gel consisting of the nanofibers as a main ingredient and other cosmetic compounding ingredients is loaded into a pack base, and a method in which the nanofibers are mixed with an ordinary cosmetic pack base, to obtain the intended pack. Though the nanofibers are used for the purposes of moisture retention and water retention, the nanofibers are not only good in moisture retention and water retention but also good in adhesion to the skin, being able to go into the fine wrinkles of the skin without making the user feel the stress of coating, hence having an effect of allowing the active ingredients of the pack to effectively permeate the skin, since the nanofibers are fibers in form. Furthermore, if other active ingredients of milky lotions and cosmetics such as a moisture retaining agent, whitening agent, anti-aging medicine and aromatic agent are mixed, these ingredients can also be well retained to increase the effect of using the pack.

The compound solution, emulsion and gel having the nanofibers dispersed in them have been explained mainly in reference to their use as cosmetics. However, the dispersibility, homogeneity and storage stability of the nanofibers can be used not merely for cosmetics but also for the materials of medical field such as ointments, wet compresses, materials of cell culture and materials of albumin adsorption, the materials of electronic material and apparatus field such as materials of electrolytes for batteries and their carriers, materials of catalyst carriers for fuel cells, materials of catalyst carriers for chemical filters and materials of hazardous gas adsorption, the materials of architectural material field such as paints, adhesives and wall coating materials respectively containing various fillers and pigments, the materials of industrial material field such as purifying filters and carriers of fine particles such as activated carbon and titanium oxide for purifying filters, coloring materials for pictures, etc.

The method for producing the nanofibers to be used in the compound solution, emulsion, gel and synthetic paper will be described below.

At first, the method for producing "polymer alloy fibers" as the raw material used for producing the nanofibers will be described. As the method for producing the polymer alloy fibers, for example, the following method can be employed.

Two or more polymers different in solubility in a solvent or liquid reagent are kneaded to produce polymer alloy chips, and they are supplied into the hopper 1 of a spinning apparatus (see FIG. 1). They are molten in a melting portion 2 to form a polymer alloy melt, and it is discharged and spun from the nozzle holes 5 formed in a spinning pack 4 in a heating and thermally insulating spinning block 3. The strands are cooled and solidified in a chimney 6, to form filaments 7, being guided along a filament-collecting finishing guide 8, a first take-up roller 9 and a second take-up roller 10, then being wound by a winder 11 as fibers. The fibers are, as required, drawn and heat-treated to obtain polymer alloy fibers. They are treated by a solvent or liquid reagent to remove the sea component, for obtaining the nanofibers used in this invention. In this case, in the polymer alloy fibers, the polymer slightly soluble in the solvent or liquid reagent and destined to be nanofibers later is used as the island component, and the polymer easily soluble in the solvent or liquid reagent is used as the sea component. If the size of the island component fibers is controlled, the number average single fiber diameter and irregularity of the nanofibers can be designed.

The size of the island component fibers is evaluated by observing a cross section of polymer alloy fibers using a transmission electron microscope (TEM) or scanning electron microscope (SEM) and calculating the equivalent diameter. The method for evaluating the number average single fiber diameter of the island component fibers in a polymer alloy fiber are described in the items F and G of measuring methods for the examples described later. Since the sizes of the island component fibers in a polymer alloy fiber as nanofiber precursors virtually decide the diameters of nanofibers, the distribution of sizes of the island component fibers is designed to conform to the intended distribution of the diameters of nanofibers. So, the kneading of the polymers to be alloyed is very important, and it is preferred to highly knead using a extrusion-kneader or static mixer or the like in this invention. Meanwhile, since simple blending of chips (for example, JP6-272114A) results in insufficient kneading, it is difficult to disperse island component fibers with sizes of tens of nanometers by such simple blending of chips.

As rule of thumb for particularly kneading, though depending on the polymers combined, in the case where a extrusion-kneader is used, it is preferred to use a twin-screw extrusion kneader, and in the case where a static mixer is used, it is preferred that the number of splits is more than one million. Furthermore, for very finely dispersing the island component fibers with sizes of tens of nanometers, the combination of polymers is also important.

To make the domains of the island component fibers (the sections of nanofibers) as circular as possible, it is preferred that the island component polymer and the sea component polymer are immiscible with each other. However, a mere combination consisting of polymers immiscible with each other does not allow the island component polymer to be very finely dispersed. For this reason, it is preferred to optimize the miscibility between the polymers to be combined, and one of the indicators for it is the solubility parameter (SP value). The SP value is a parameter reflecting the cohesive force of a substance defined by (evaporation energy/mole volume)$^{1/2}$, and substances close to each other in SP value are likely to form a highly miscible polymer alloy. SP values of various polymers are known and stated, for example, in "Plastic Data Book (in Japanese)" (edited by Plastic Edition Department, Asahi Kasei AMIDAS Co., Ltd.; issued on Dec. 1, 1999 (by Kogyo Chosakai Publishing Co., Ltd.; page 189), etc.

It is preferred that the difference between two polymers in SP value is 1 to 9 $(MJ/m^3)^{1/2}$, since both the circularization and the very fine dispersion of island component domains owing to immiscibility can be easily realized. For example, N6 and PET are a preferred combination, since the difference between them in SP value is about 6 $(MJ/m^3)^{1/2}$, and N6 and PE are not a preferred combination, since the difference between them in SP value is about 11 $(MJ/m^3)^{1/2}$.

Furthermore, it is preferred that the difference between the polymers in melting point is 20° C. or less, since especially when they are kneaded using an extrusion kneader, they are virtually equally molten in the extrusion kneader, to allow efficient kneading. In this case, in the case of an amorphous polymer, since it does not have a melting point, a Vicat softening temperature or thermal deformation temperature or glass transition temperature should be referred to instead of the melting point.

Moreover, the melt viscosity is also important. It is preferred in view of nanofiber production that the melt viscosity of the polymer forming the islands is set at a lower value, since the island polymer is likely to be deformed by shearing force and can be easily finely dispersed. However, if the island polymer is made excessively lower in viscosity, it is likely to form the sea, and the blending ratio in the entire fiber cannot be made high. So, it is preferred that the viscosity of the island polymer is 1/10 or more of the viscosity of the sea polymer. Furthermore, the melt viscosity of the sea polymer may exert large influence on the spinnability, and it is preferred that a polymer with a low viscosity of 100 Pa·s or less is used as the sea polymer, since the island polymer can be easily dispersed. Furthermore, in this case, the spinnability can be remarkably improved. The melt viscosity in this case refers to a value at a shear rate of 1216 sec$^{-1}$ at the spinneret temperature during spinning.

Moreover, to enhance stringiness and spinning stability, it is preferred to cool the yarn with the spinneret temperature kept at 25° C. or more higher than the melting point of the sea polymer and with the distance from the spinneret to the cooling start point kept at 1 to 15 cm.

It is preferred that the spinning speed is higher in view of achieving a higher draft in the spinning step, and a draft of 100 or more is preferred from the viewpoint of reducing the nanofiber diameter. Furthermore, it is preferred that the spun polymer alloy fibers are drawn and heat-treated, and for keeping the yarn unevenness small, it is preferred that the preheating temperature for drawing is higher than the glass transition temperature (Tg) of the island polymer.

In this production method, if the combination of polymers and the spinning and drawing conditions are optimized as described above, the island polymer can be very finely dispersed to form island fibers with a diameter of tens of nanometers, and polymer alloy fibers small in yarn unevenness can be obtained. The "polymer alloy fibers" are small in the irregularity of island polymer fiber diameter not only at certain cross sections but also at all cross sections in the longitudinal direction.

Figure 2:
FIG. 2 is a transmission electron microscope (TEM) photograph showing forms of islands on a cross section of a polymer alloy fiber of Example 1.

The "polymer alloy fibers" spun by the above method have a single fiber fineness of 1 to 15 dtex (diameter 10 to 40 μm) and can be obtained as a fiber bundle (5000 dtex or less) consisting of filaments. Furthermore, depending on the diameter of the island component fibers, each of the "polymer alloy fibers" has thousands to millions of island polymer fibers (several weight percent to 80 wt %) dispersed as nanofiber precursors in the sea polymer (see FIG. 2).

The method for producing nanofibers from the "polymer alloy fibers" will be described below.

It is preferred that the nanofibers are short fibers, to improve the homogeneous dispersibility and long-term storage stability of nanofibers, and it is preferred to remove the sea component from the "polymer alloy fibers" and then to cut them into short fibers. Furthermore, it is preferred to beat the cut fibers.

The short nanofibers can be obtained by either removing the sea component from the bundle of "polymer alloy fibers", to obtain a nanofiber bundle, and subsequently cutting the fibers (sea component pre-removal method) or cutting the bundle of "polymer alloy fibers" and subsequently removing the sea component (sea component after-removal method). Moreover, it is preferred to beat the obtained short fibers by a beater till the nanofibers are scattered.

In the case of the sea component pre-removal method, at first, usually the bundle of "polymer alloy fibers" as a hank (5000 dtex or less) or a tow consisting of such bundles (more than 5000 to millions of dtex) get the sea component removed using a solvent (extract) or liquid reagent capable of dissolving the sea component, and washed with water and dried, then being cut to an adequate fiber length using a guillotine cutter or slice machine. In the case of the sea component after-removal method, at first, the bundle of "polymer alloy fibers" as a hank or a tow consisting of such bundles are cut to an adequate fiber length by a guillotine cutter or slice machine, and subsequently get the sea component removed using a solvent or liquid reagent capable of dissolving the sea component, washed with water, and dried. It is preferred that the adequate fiber length of the short nanofibers is 0.05 to 5 mm in the case of compound solution, emulsion or gel. A more preferred range is 0.2 to 1 mm. It is preferred that the adequate fiber length of short nanofibers in the case of synthetic paper is 0.1 to 20 mm. A more preferred range is 0.2 to 1 mm. If the fiber length of nanofibers is too long, dispersion is unlikely to be achieved, and if too short, the nanofibers become like a powder, being likely to cohere to each other.

The solvent or liquid reagent used for removing the sea component from the "polymer alloy fibers" can be an alkali such as caustic soda or caustic potash, an acid such as formic acid or an organic solvent such as trichlene, limonene or xylene, etc. selected in response to the properties of the sea component polymer. In the case where a bundle of "polymer alloy fibers" or a tow gets the sea component removed, the fibers can be provided as a hank or wound around a hank reel. However, in the case where the "polymer alloy fibers" as a hank get the sea component removed by a solvent or liquid reagent, since the amount of the sea component removed from the "polymer alloy fibers" is usually as very large as 20 to 80 wt %, the removal of the sea component causes the hank to be reduced in volume in the diameter direction, and the "polymer alloy fibers" in the hank may adhere to each other, not allowing the solvent or liquid reagent permeate among the fibers. Furthermore, the hank may be once dissolved on the surface and covered with the re-precipitated polymer, making it gradually difficult to remove the sea component polymer. In the worst case, the hank may become like a round pie, making it very difficult to promote the removal of the sea component from the "polymer alloy fibers". To avoid this trouble, it is preferred that a fiber bundle is wound around a hank reel, instead of being provided as a mere hank, since the hank shrinkage can be prevented for inhibiting that the "polymer alloy fibers" adhere to each other, to allow the solvent to be kept easily flowing among the "polymer alloy fibers". If this method is employed, the sea component can be removed not only from a bundle of "polymer alloy fibers" but also from a tow. For more efficiently removing the sea component, it is preferred that the total fineness of a tow is 500,000 dtex or less. A more preferred fineness is 100,000 dtex or less. On the other hand, since the productivity in removing the sea component can be improved if the total fineness of "polymer alloy fibers" is larger, it is preferred that the total fineness of "polymer alloy fibers" is 10,000 dtex or more.

Moreover, the sea component polymer can also be decomposed using a liquid reagent such as an alkali, for being removed. In this case, the sea component can be relatively easily removed even if the fibers are provided as a hank. The reason is that the sea component polymer can be depolymerized into the oligomer or monomer by hydrolysis or the like, for being easily dissolved and removed. Furthermore, if the sea component is removed by decomposition, clearances are formed among the fibers, and the liquid reagent such as an alkali permeates among nanofiber precursors in the "polymer alloy fibers". So, with the progression of sea component removal, the sea component removing rate is accelerated, and the sea component can be sufficiently removed even as a hank, unlike the dissolution removal of the sea component using an organic solvent, etc.

It is preferred that the nanofiber bundle obtained by treating a fiber bundle such as a tow or hank consisting of the "polymer alloy fibers" provided as nanofiber-formable fibers using a solvent or liquid reagent has a nanofiber area ratio of 95 to 100% based on the area of all the fibers. This means that the sea component little remains in the nanofiber bundle getting the sea component removed, and this can minimize the ingress of coarse fibers. If the nanofibers are used to make paper, a nanofiber synthetic paper with a high grade can be obtained.

In this invention, it is preferred that a fiber bundle consisting of the "polymer alloy fibers", i.e., nanofiber-formable fibers have a fiber density of 0.01 to 0.5 g/cm$^3$, when they are treated by a solvent or liquid reagent for removing the sea component. If the fiber density of the fiber bundle is lower than 0.01 g/cm$^3$ when the fiber bundle is treated by a solvent or liquid reagent for removing the sea component, the fiber bundle treated becomes unstable in form, and it can happen that the nanofibers are not formed uniformly. On the other hand, if the fiber density of the fiber bundle is higher than 0.5 g/cm$^3$, the permeation of the solvent or liquid reagent into the fiber bundle may become poor, not allowing the nanofibers to be perfectly formed, and the nanofiber content of the nanofiber bundle may decline. It is more preferred that the fiber density of the fiber bundle when the fibers are treated by a solvent or liquid reagent for removing the sea component is 0.01 to 0.4 g/cm$^3$. A further more preferred range is 0.03 to 0.2 g/cm$^3$.

In the case where the sea component is decomposed and removed using a liquid reagent such as an alkali, it is preferred that the sea component of the "polymer alloy fibers" is a polymer likely to be decomposed by an alkali. It is preferred that the sea component is a PLA-based or PVA-based polymer. As described in Example 38 given later, when the copolymerized PET of Example 29 was changed to the PLA of Example 38, the concentration of sodium hydroxide could be remarkably decreased from 10 wt % to 1 wt %. In the case where an alkali is used for treatment at a high temperature and a high concentration, such sea component removal work using an alkali is very dangerous and the working efficiency is low. Furthermore, the usable apparatus is very limited owing to leak and corrosion. Moreover, when the alkali remaining in the treating solution after completion of sea component removal is treated as a waste liquor, it is necessary to use a large intermediate bath for gradually diluting the alkali solution to avoid the neutralization heat generated during neutralization, since the alkali concentration is high. If the alkali concentration in the treating solution used for sea component removal can be lowered, such dangerous work can be avoided, and the sea component can be efficiently removed. The load on the waste liquor treatment process can also be reduced.

For the sea component after-removal method, a particular method will be described below.

For removing the sea component from the short fibers obtained by cutting the "polymer alloy fibers", the short fibers are immersed in an organic solvent or a liquid reagent such as an alkali or acid, and are stirred using a stirrer, to dissolve or decompose the sea component, for removing it. It is usually preferred that the sea component removal is performed in batch processing in several stages. In the case where the sea component is efficiently dissolved and removed using an organic solvent such as trichlene, when the sea component is dissolved in the first stage, it is preferred to lower the concentration of the sea component polymer dissolved in the solvent to 6 wt % or less. More preferred is 3 wt % or less. When the sea component is removed in the second and later stages, it is preferred to gradually lower the concentration of the polymer dissolved in the solvent to 0.1 wt % or less. More preferred is 0.01 wt % or less. Furthermore, in the case where the sea component is efficiently decomposed and removed by means of hydrolysis or the like using a liquid reagent, it is preferred to lower the concentration of the sea component dissolved as the oligomer or monomer due to decomposition in the liquid reagent to 10 wt % or less. More preferred is 5 wt % or less. When the sea component is removed in the second and later stages, it is preferred to gradually lower the concentration of the sea component dissolved as the oligomer or monomer in the liquid reagent to 0.1 wt % or less. More preferred is 0.01 wt % or less. The short fibers obtained by cutting the "polymer alloy fibers" are treated using any of various solvents or liquid reagents as described above and subsequently filtered using an adequate stainless steel screen filter or the like, to collect the nanofibers. Then, the solvent or liquid reagent deposited on the nanofibers are thoroughly washed away, being followed by drying.

Irrespective of whether the sea component is removed from a fiber bundle, tow or cut fibers of the "polymer alloy fibers", for efficient removal of the sea component, it is preferred to use a new one as the solvent such as an organic solvent or a liquid reagent such as an alkali or acid used for removing the sea component in the second and later stages, and to use a temperature as high as possible for the treatment of removing the sea component, and further to keep the solvent or liquid reagent stirred for circulation. Moreover, it is preferred that the ratio of the amount of fibers to the amount of the solvent or liquid reagent used for removing the sea component is as small as possible, to ensure that the sea component concentration in the solvent or liquid reagent after completion of sea component removal treatment can be kept small.

Between the respective stages of sea component removal treatment after the first stage, it is preferred that the fiber bundle, tow or cut fibers impregnated with the solvent or liquid reagent are centrifuged to remove the solvent or liquid reagent to some extent. It is preferred that the amount of the solvent or liquid reagent based on the weight of the fibers is 200 wt % or less, since the handling convenience in the next stage can be improved. Furthermore, it is preferred that the amount of the solvent or liquid reagent based on the weight of the fibers is 50 wt % or more, since the solvent or liquid among the fibers functions as a spacer to inhibit that the fibers adhere to each other excessively, thereby enhancing the permeability of the solvent or liquid reagent in the next stage, hence enhancing the sea component removal efficiency. Moreover, for enhancing the sea component removal efficiency, in the case where sea component removal treatment is performed plural times, it is preferred to wash after completion of treatment of each stage, for removing the sea component deposited on the fibers to decrease the amount of the sea component flowing into the solvent or liquid reagent later. After completion of sea component removal by a solvent or liquid reagent, it is preferred to wash the fibers for decreasing the sea component deposited on the fibers to 0.1 wt %, for reducing the remaining sea component. More preferred is 0.01 wt % or less.

In the case where a nanofiber bundle is obtained by the sea component pre-removal method, the obtained nanofiber bundle or tow can be cut to an adequate length suitable for the application or purpose of the nanofibers using a guillotine cutter or slice machine. In this case, it is preferred that the fiber bundle or tow has a water content of 20 to 100 wt % before being cut. If the nanofiber bundle or tow free from the sea component contains water to some extent, the fibers are more convenient to handle since they are well bundled, and furthermore, since they can be cut more accurately, the uniformity of cut length can be enhanced. Moreover, since the fusion bonding between the short fibers by the heat generated during cutting can also be inhibited, the adhesion of short fibers to the cutting blade decreases, to enhance the production efficiency of cutting. It is also preferred to apply 0.01 to 1 wt % of an oil (with oil purity as 100%) to the fiber bundle or tow. The short nanofibers obtained like this are an aggregate consisting of thousands to millions of nanofibers, though depending on the diameter of the nanofibers.

Then, a beater is used to beat the short nanofibers. The beating allows the short nanofibers to be scattered individually.

The beater used for industrial production can be a Niagara beater, refiner or mill, etc. The beater used for an experimental purpose can be a household blender, cutter, laboratory grinder, biomixer, roll mill, mortar, or PFI mill, etc.

On a transmission electron microscope (TEM) or scanning electron microscope (SEM) photograph showing a cross section of a short nanofiber aggregate, the nanofibers are observed to be individually separated, and a small amount of the nanofibers existing on the surface are observed to be liberated from the surfaces of the short nanofibers. However, since most of the short nanofibers exist as an aggregate, it is difficult to scatter the nanofibers into individual single fibers even if the short nanofibers are lightly rubbed or merely stirred in water. The reason is considered to be that since the diameter of the nanofibers is very small and since the specific surface area is very large compared with that of the conventional fine fibers, the interaction such as the hydrogen bonding force and the intermolecular force working among the fibers is very powerful, making the cohesive force large.

For this reason, it is preferred to make the short nanofibers scattered individually by any of the beaters enumerated above. However, among the beaters, a cutter or a device having grinding blades is likely to damage the fibers and has a disadvantage to cut the fibers for making them shorter and shorter in addition to the effect of scattering the fibers individually. Since the nanofibers are large in the cohesive force between fibers but are thin, a cutter or a device having grinding blades can greatly damage the fibers, and in the worst case, may grind the fibers into a powder. So, even though the beater is expected to beat, a beater capable of rubbing the fibers for loosening them or applying shearing force to disengage the cohesion among fibers is preferable to a beater capable of applying a force of grinding or cutting. Especially a PFI mill uses the shearing force acting due to the circumferential speed difference between the inner blades and an outer vessel for beating, and preferably very little damages the fibers before it makes the fibers scattered individually. Moreover, in the case where another beater is used, it is preferred to lower the beating speed and to decrease the pressure acting during beating. For reducing the impact force acting on the nanofibers to decrease the damage to the fibers, it is preferred to lower the beating speed and to decrease the pressure acting during beating, for processing the fibers under soft conditions. Even a household or laboratory blender can beat the nanofibers to scatter them individually like the aforesaid beater in view of quality, if it is used for a long time under soft conditions such as a low rotational speed, though the efficiency is low.

It is preferred that beating is performed twice as first step beating and second step beating. In the first step beating, it is preferred that the nanofiber aggregate is lightly rubbed to be loosened by shearing force, for reducing the number of nanofibers constituting the respective sets of nanofibers to some extent. It is preferred that the first step beating is performed to such an extent that the freeness expressing the beating degree of fibers becomes 500 or less. It is more preferred to achieve a freeness of 350 or less, and it is preferred to achieve a freeness of 5 or more. In this case, the freeness refers to the value measured according to the Canadian Standard Freeness Test Method described in JIS P 8121 "Freeness Test Method of Pulp" shown in "L. Freeness test method of nanofibers" for the examples given later. When the freeness of nanofibers is measured, it can happen that the beaten nanofibers dispersed as small groups in water clog the filter in the vessel of the freeness tester. They should also be taken into account when the freeness value is measured. In the case where a Niagara beater or refiner is used for performing the first step beating, generally the short nanofibers are dispersed in water. It is preferred that the nanofiber concentration in the dispersion as a whole is 5 wt % or less, since beating can be performed uniformly. More preferred is 1 wt % or less. It is also preferred that the nanofiber concentration is 0.1 wt % or more, since the beating efficiency can be enhanced. In the first step beating, it is preferred that the set clearance of the beater such as a Niagara beater or refiner is rather as large as 0.5 to 2 mm, since the load acting on the beater due to pressure and the time of beating treatment can be decreased. Furthermore, a laboratory grinder, blender or cutter can also be used if soft conditions are employed. It is preferred that the beaten nanofibers are collected by filtration using an adequate screen filter or the like, and dehydrated by a dehydrator to have a water content of 50 to 200%, for being stored, since the volume of the beaten nanofibers can be kept small to require a smaller space for storage and to facilitate the handling in the subsequent process.

The second step beating in this invention is to accurately beat the nanofibers beaten in the first step. The beater used in this case can be a Niagara beater, refiner or PFI mill, etc. It is preferred that the set clearance of the beater is 0.1 to 1.0 mm. A more preferred range is 0.1 to 0.5 mm. It is preferred that the pressure is also small for beating under soft conditions. In the case where a refiner is used, the blades contained in the refiner can be adequately changed in form, and it is preferred to select the form with a rubbing effect or a shearing effect rather than an effect of cutting fibers. Especially for experimentally performing the second step beating of nanofibers, it is most suitable to use a PFI mill. Since a PFI mill beats by the shearing force acting due to the circumferential speed difference between the inner blades and an outer vessel, the damage of nanofibers before the nanofibers are beaten to be individual is very small preferably. Furthermore, the nanofiber concentration can be kept as high as 5 to 20 wt % during beating, and since the inner blade portions of the beater are kept uniformly applied to the fibers, the nanofibers can be uniformly beaten without being further cut in the fiber length direction or without being powdered even if the beating makes the nanofiber aggregate thinner and lowers the strength of nanofibers. It is preferred that the freeness of the disarranged nanofibers obtained by the second set beating like this is 350 or less. More preferred is 200 or less, and further more preferred is 100 or less. Preferred is 5 or more.

If the freeness is more than 350, the beating degree is small, and insufficiently beaten fibers remain. In this case, since the nanofibers are beaten insufficiently, the nanofibers may not be homogeneously dispersed in the synthetic paper obtained. In the case where a Niagara beater, refiner, household or laboratory blender or cutter is used for the second step beating, since the nanofiber concentration in water is low, the rotating blades locally repetitively applied also to the floating nanofibers made thinner by beating, and the effect of cutting and crushing the fibers is large, the fibers being likely to be cut in the fiber length direction or powdered. So, it is preferred to keep the beating conditions such as blade form, rotating speed and pressure condition mild during beating.

In order to prevent that the nanofibers beaten like this cohere to each other again, it is preferred that after they have been beaten in water or in a solvent, they are collected by filtration using a filter and dehydrated (or get the solvent removed) by a dehydrator to have a water content or solvent content of 50 to 200 wt %, for being stored. If it is absolutely necessary to dry for storing, freeze-drying or vacuum drying at a low temperature of lower than 60° C. is preferred.

In the above description, the nanofibers are beaten in water, but if it is necessary to beat the nanofibers in a special solvent, it is preferred to beat in the solvent.

In the beating of conventional cellulose or synthetic fibers, the fibers are beaten in water and dried, and the dried fibers are dispersed in an intended emulsion or solvent using a stirrer. Even by this method, the conventional ordinary fibers and ultrafine fibers could be re-dispersed in a solvent or water. However, in the case of nanofibers, since the specific surface area of the fibers is very large as shown in Table 1, the fibers scattered individually in water by the effort of beating cohere to each other again during drying, and even if it is attempted to disperse the fibers by an ordinary stirrer, it is difficult to homogeneously disperse them. For this reason, it is preferred to beat the fibers directly in at least the intended one selected from the group consisting of water, oils and organic solvents. As the solvent, a mixed solvent consisting of an organic solvent and water may be preferred as the case may be. A general beater is usually used for beating in water, but since it is not prepared for an organic solvent, an explosion-proof beater should be used or a working environment measure for collecting the evaporated solvent should be taken. Depending on the solvent used, a safety measure such as wearing a working mask must be taken. In the case where the nanofibers are mixed in a highly viscous gel such as a face-washing gel, hair-dressing gel, wet-compress gel, ointment, or a cream, emulsion or the like with a high viscosity, it is preferred to use a kneader or kneading machine instead of a stirrer.

In the case where the fibers are beaten directly in an organic solvent, since it is necessary to use a special explosion-proof beater or to take any safety measure, expensive equipment investment may be necessary. To avoid this problem, the water contained in the nanofibers beaten in water can be substituted by an organic solvent. The method will be described below.

It is preferred as described above that the short nanofibers beaten in water are at first dehydrated by a dehydrator to have a water content of 0.3 to 300 times the weight of the nanofibers. A more preferred range is 2 to 100 times. This allows the re-cohesion of nanofibers to be inhibited. Since nanofibers have a large specific surface area, they can highly retain water, and even in the case where the nanofibers have a very high water content of about 10 times the weight of the nanofibers, since much water can be held among the fibers, it little happens that water drips. The nanofibers can contain far more water based on the weight of the fibers than the conventional fibers. To keep the nanofibers well dispersed, it is preferred that the nanofibers have a water content of 5 to 30 times the weight of the nanofibers. However, if the water content is too large, the efficiency of substituting water by a solvent declines.

Then, the dehydrated nanofibers are placed in an arbitrary vessel, and a solvent used for substitution is added into it. It is preferred that the amount of the solvent supplied at the $1^{st}$ time is 2 to 50 times the amount of water contained in the nanofibers, and a more preferred range is 5 to 20 times. The solvent used depends on the polymer of the nanofibers and the application or purpose of the product, but since it is intended to substitute water, a hydrophilic solvent familiar with water is preferred. Such solvents as alcohols, ethers, esters, ketones and DMF are preferred.

After the solvent is added, the added solvent and the water contained in the nanofibers are stirred in a vessel by a stirrer for 5 to 60 minutes. After completion of stirring, the nanofibers and the solution are filtered, for example, by a metallic screen filter, to separate the remaining solution. To keep dispersibility, it is preferred that the amount of the remaining solution contained in the nanofibers is one time or more of the weight of the nanofibers when the remaining solution is separated.

It is preferred that the substitution by the solvent is performed twice or more, and it is more preferred that the substitution is performed five times or more. This can be achieved by repeating several times the cycle of adding the solvent and separating the nanofibers from the mixed solvent consisting of the solvent and water. This method has a problem that some water remains though the dispersibility of the nanofibers in the solvent can be well maintained.

In the above-mentioned method, even the method of concentrating the water content to a range of 10 to 50 wt % by means of centrifugation for dehydration can decrease the remaining water considerably if the substitution by the solvent is repeated. However, in this method, when the nanofibers are dispersed into the solvent later, the dispersibility may decline later. Furthermore, the Soxhlet extraction method can also be used for the substitution by the solvent, but the dispersibility of nanofibers may also decline.

The method for preparing a nanofiber compound solution will be described below.

Beaten nanofibers and a solvent are dispersed at a predetermined concentration in a stirrer. Though depending on the single fiber diameter of the nanofibers produced, it is preferred that the nanofiber concentration based on the weight of the compound solution as a whole is 5 wt % or less. A more preferred range is 0.0001 to 1 wt %, and a further more preferred range is 0.01 to 1 wt %. Furthermore, since the nanofibers are likely to cohere with each other, it is preferred to disperse at a concentration as low as possible for preventing re-cohesion. Moreover, to enhance the dispersibility of nanofibers, it is preferred to add a dispersing agent. It is preferred that the dispersing agent used in the aqueous system is selected from anionic dispersing agents such as polycarboxylates, cationic dispersing agents such as quaternary ammonium salts, and nonionic dispersing agents such as polyoxyethylene ethers and polyoxyethylene esters.

For selecting an adequate dispersing agent, for example, in the case where the charge repulsion between nanofibers is used for dispersion, the dispersing agent is selected in reference to the surface potential (zeta potential) of nanofibers. In the case of nanofibers with their zeta potential kept in a range from −5 to +5 mV at pH 7, it is preferred to add a nonionic dispersing agent. If the zeta potential is −100 mV to less than −5 mV, it is preferred to select an anionic dispersing agent. If the zeta potential is more than +5 mV to 100 mV, it is preferred to add a cationic dispersing agent. For example, N6 nanofibers are negatively charged on the surfaces to have a zeta potential (about pH 7) of −14 mV as measured by the laser Doppler electrophoresis, and if an anionic dispersing agent is used to make the potential larger in absolute value, the zeta potential becomes −50 mV to enhance dispersibility. Furthermore, in the case where steric repulsion is used for dispersion, if the molecular weight of the dispersing agent is too large, the dispersing agent has an effect of acting rather as a flocculating agent. So, it is preferred to control the molecular weight of the dispersing agent. It is preferred that the molecular weight of the dispersing agent is 1000 to 50000. A more preferred range is 5000 to 15000.

However, even a dispersing agent with the same chemical composition is affected also by its molecular weight, the polymer used as the nanofibers, nanofiber concentration and other compounding ingredients. So, it is preferred to select an adequate dispersing agent in response to the polymer used as the nanofibers and the application or purpose of the nanofibers, for preparing the solution. It is preferred that the dispersing agent concentration is 0.00001 to 20 wt % based on the total weight of the compound solution. A more preferred range is 0.0001 to 5 wt %, and a further more preferred range is 0.01 to 1 wt %. If the dispersing agent concentration is in this range, a sufficient dispersion effect can be obtained. Furthermore, in the case of a compound solution containing such nanofibers, it is preferred that the fiber length of nanofibers is 0.05 to 5 mm. A more preferred range is 0.2 to 1 mm. Moreover, in the case where the solvent is hydrophobic like an oily solvent or organic solvent, it is preferred to use an acrylamide-based dispersing agent, silicone-based dispersing agent or fluorine-based dispersing agent.

The method for producing a nanofiber emulsion will be explained below.

Emulsions include two major types: O/W (oil-in-water) type and W/O type (water-in-oil) type. Furthermore, depending on the polymer used as the nanofibers, there are a case where the nanofibers are likely to be dispersed in water (W) and a case where they are likely to be dispersed in oil (O). It is preferred to select the emulsion type in response to the polymer used as the nanofibers, the water and oil used in the emulsion, their mixing ratio, the dispersing agent used, its mixing ratio, the solvent added, temperature, etc. as well as in response to the application or purpose of the product. Furthermore, in the case where many ingredients are compounded, it is preferred to design the compounding ratio of the respective ingredients of the emulsion, considering the affinity between the nanofibers and the compounding ingredients and the dispersibility of the nanofibers.

Irrespective of the emulsion type, it is preferred that the nanofiber concentration is 5 wt % or less. A more preferred range in view of the homogeneous dispersibility of nanofibers is 0.0001 to 1 wt %. It is further more preferred for ensuring the stability of the emulsion per se that the nanofiber concentration is in a lower range of 0.001 to 0.5 wt %. Furthermore, it is preferred to select an adequate dispersing agent for preparing the emulsion in response to the polymer used as the nanofibers and the application or purpose of the nanofibers. The method for selecting an adequate dispersing agent is as described before. It is preferred that the dispersing agent concentration is 0.00001 to 20 wt % based on the total weight of the emulsion. A more preferred range is 0.0001 to 5 wt %, and a further more preferred range is 0.01 to 1 wt %. If the dispersing agent concentration is in this range, a sufficient dispersion effect can be obtained. Furthermore, the fiber diameter of the nanofibers is very small on the nanometer level, but since the fiber length is large compared with the diameter, it is difficult to disperse nanofibers compared with nanoparticles. So, it is preferred that the fiber length of the nanofibers for an emulsion is 0.05 to 2.0 mm. A more preferred range is 0.05 to 0.8 mm. Meanwhile, if nanofibers are treated with a surface treating agent such as an oil (for example, a silicone oil) and added to an emulsifying agent, the nanofibers alone may be able to be dispersed to form an emulsion as the case may be.

The nanofiber gel will be described below together with a nanofiber structural gel.

If nanofibers are mixed with water (or another solvent) with the nanofiber concentration kept at 5 to 60 wt %, a "structural gel" is formed, though depending on the polymer used as the nanofibers, and this is a peculiar phenomenon. The structural gel in this case refers to a substance consisting of nanofibers and water (or another solvent) having a relatively high nanofiber content of 5 to 60 wt %. This is neither an aqueous solution nor a solid. Furthermore, since the polymer used as the nanofibers does not have a crosslinked structure, this substance is hereinafter called a "structural gel". If ordinary fibers or ultrafine fibers are mixed with water (or another solvent) in this concentration range, an aqueous solution (or another solution) with a low viscosity is formed. However, in the case of nanofibers, the specific surface area of nanofibers is large and the hydration effect among nanofibers is very large (see Table 1). This is considered to be the reason why such a peculiar phenomenon occurs. For producing the structural gel, when the nanofibers are beaten, the nanofiber concentration can be kept in a high range of 10 to 30 wt %.

Furthermore, the "gel" produced herein refers to a gel obtained by adding a solvent or gel to nanofibers and further, as required, adding a certain material. The certain material refers to a polymer gel such as PVA gel or acrylamide gel or a natural material gel such as a polysaccharide. Furthermore, since the aforesaid "structural gel" of nanofibers is a pseudo gel, though it does not have a crosslinked structure, it is also included in the "gel." The gel with a high nanofiber concentration can be produced with the nanofiber concentration kept at 10 to 30 wt % when the nanofibers are beaten. Furthermore, to obtain a highly concentrated nanofiber gel, a dispersing agent such as an acrylamide-based dispersing agent, silicon-based dispersing agent or fluorine-based dispersing agent can be added to enhance the homogeneity of dispersion. The method for selecting an adequate dispersing agent is as described before, and an anionic, cationic or nonionic dispersing agent can also be suitably used. Moreover, it is preferred that the dispersing agent concentration is 0.00001 to 20 wt % based on the total weight of the gel. A more preferred range is 0.0001 to 5 wt %, and a further more preferred range is 0.01 to 1 wt %. If the dispersing agent concentration is in this range, a sufficient dispersion effect can be obtained.

In the case where a gel with a low nanofiber concentration is produced, as in the case of a nanofiber complex solution, for example, a natural gel or synthetic gel can be added to a 0.01 to 1 wt % nanofiber compound solution, to produce a gel. Examples of the natural gel or synthetic gel include protein gels such as collagen, gelatin and chitosan, natural gels such as agarose, alginic acid, pectin and polysaccharide gel, cellulose gel, etc., and furthermore synthetic polymer gels such as PVA-based gels, crosslinked vinyl-based polymers, acrylamide-based gels, alkali metal acrylate gels, alkaline earth metal acrylate gels, silicone-based gels, fluorine-based gels, urethane-based gels and radiation-crosslinked polymer gels, etc. In the case of such a nanofiber-containing gel, it is preferred that the fiber length of nanofibers is 0.05 to 2 mm. A more preferred range is 0.2 to 1 mm.

The nanofiber synthetic paper will be described below.

The fiber diameter of the ultrafine fibers contained in the conventional synthetic paper is usually 1 μm or more. Even if fibers of 1 μm or less are contained, the irregularity of fiber diameters is generally large, and since the fibers per se cannot be entangled with each other, stable papermaking has been difficult. Furthermore, if a PVA fiber binder with a large fiber diameter or a pulpy binder or the like is used together to allow papermaking, the intended synthetic paper consisting of 100% synthetic fibers cannot be obtained. Especially in the fields sensitive to impurities such as biotechnology and battery separators and in the medical field requiring a thin and accurate membrane such as an adhesion preventive membrane for surgery, the conventional ultrafine fibers could not meet the respective needs.

The synthetic paper of this invention, which uses disarranged nanofibers, can be made of nanofibers alone. So, the above-mentioned problems can be solved.

Furthermore, the synthetic paper has a feature that the specific surface area is dramatically large, since the number average single fiber diameter of the disarranged nanofibers used in the synthetic paper of this invention is 1/10 to 1/100 of those of the conventional ultrafine fibers. Therefore, the synthetic paper shows peculiar properties not observed in the synthetic paper composed of usual ultrafine fibers, and it is expected that the adsorption properties can be greatly improved. That is, the synthetic paper is likely to adsorb water vapor (hygroscopic), chemical reagent vapors (odors), fine powders, dusts, etc.

For example, a synthetic paper composed of conventional N6 ultrafine fibers had a moisture absorption coefficient of about 2.8% (Comparative Example 18 given later), but a N6 nanofiber synthetic paper of this invention had a moisture absorption coefficient of 6.4% (Example 29 given later).

Furthermore, if nanofibers with a very small fiber diameter compared with the conventional ultrafine fibers are used, even a synthetic paper with a very small weight per unit area of 2 g/m$^2$ as shown in Example 33 given later has few pinholes and uniform evenness. Thus, a synthetic paper having a very small thickness and yet a very low air permeability can be produced. This synthetic paper can be used, for example, as a battery separator material allowing the migration of ions, trace gas or trace chemical substance but not allowing the mass migration of a liquid. Meanwhile, in medical surgery, the leak of body fluid or ascites fluid from the diseased part during or after surgery can be a fatal impairment or the leaking body fluid or ascites fluid can cause contamination with another pathogenic microbe. So, a diaphragm for operation compatible with the organism and capable of preventing the leak of body fluid is needed. As the material, an antithrombotic polymer film has been used, but the polymer film is not flexible being a material difficult to handle during surgery. The synthetic paper is suitable also for use as such a diaphragm for operation.

Furthermore, the synthetic paper has a feature that the nanofibers are dispersed into individual single fibers, and a synthetic paper uniform in the weight per unit area, thickness, evenness, etc. can be obtained as described in Example 29 given later. Moreover, the nanofiber synthetic paper does not contain the powdery fiber refuse produced by damaged nanofibers when the nanofibers are beaten, and when a synthetic paper is produced from the nanofibers, a uniform sheet with few defects can be formed.

In the cell culture and albumin adsorption and removal in the medical field and the biotechnology field, materials of nanometer size become important, but the nanofibers produced by the "electrospinning" technique described in the "Prior Art" are insufficient in the uniform control of fiber diameters. The nanofibers existing within or on the surfaces of the synthetic paper of this invention are suitable for the sizes of adsorbed regions of cells and proteins (proteins, enzymes, bacteria, viruses, etc. existing in various bloods), and the nanofibers are expected to directly interact with these cells and proteins. So, the synthetic paper is useful also as an adsorbing material for medical service and biotechnology.

When the nanofiber synthetic paper is used in these applications, there are cases where it is used because of its surface properties or its permeability and impermeability, and cases where it is used for allowing fluids, fine particles, etc. to pass through it. The applications in the former cases include a battery separator, abrasive, etc., and in these cases it is preferred that the weight per unit area of the synthetic paper is relatively higher. Considering the flexibility of the synthetic paper to be formed into the intended structure and the packing property of the nanofibers in the synthetic paper, it is preferred that the weight per unit area of the synthetic paper is 50 g/m$^2$ or less. More preferred is 30 g/m$^2$ or less, and further more preferred is 10 g/m$^2$ or less. If the weight per unit area is too low, pinholes may be formed. So, the lower limit of weight per unit area is 1 g/m$^2$ or more.

The applications in the latter cases include an air filter, liquid filter and medical products such as blood filter. It is preferred that the synthetic paper is thinner for efficient permeation of a gas or liquid, though the thickness also has relation with the density of the synthetic paper. It is preferred that the weight per unit area of synthetic paper is 10 g/m$^2$ or less, and more preferred is 5 g/m$^2$ or less. The lower limit is not especially limited, but the lower limit of weight per unit area is 0.5 g/m$^2$ or more.

In the case of a compound synthetic paper partially containing nanofibers, it is preferred that the weight per unit area of the nanofibers only existing in the compound synthetic paper is 5 g/m$^2$ or less. More preferred is 1 g/m$^2$ or less. The lower limit of the weight per unit area is 0.0001 g/m$^2$ or more.

The thickness of the synthetic paper is not especially limited, since it can be freely controlled to suit each object by adjusting the weight per unit area. However, to obtain good papermaking properties and a synthetic paper with good evenness, and to sufficiently withstand stresses such as the tensile stress acting when the synthetic paper is processed into various products such as a filter and a separator, it is preferred that the thickness is 10 µm or more. More preferred is 100 µm or more, and further more preferred is 150 µm or more. It is preferred that the upper limit of thickness is 5000 µm (5 mm) or less.

Furthermore, it is preferred that the density of the nanofiber synthetic paper of this invention is 0.3 g/cm$^3$ or less, lest the synthetic paper should be likely to be wrinkled when it is used for various applications or when it is processed, and lest the surfaces of the synthetic paper should be uneven. More preferred is 0.2 g/cm$^3$ or less, and further more preferred is 0.1 g/cm$^3$ or less. It is preferred that the lower limit of density is 0.001 g/cm$^3$ or more.

The synthetic paper can be produced even without a binder, aggregate or base material, etc., even if it is a thin synthetic paper with a weight per unit area of 8 g/m$^2$ as described in Example 29 given later. The reason is considered to be that since the nanofibers have a high force to cohere with each other, though difficult to disperse, the high cohesive force can be very conveniently used on the contrary for papermaking, and that the nanofibers can be excellently entangled with and adhere to each other.

Furthermore, in order to obtain such nanofibers with good papermaking properties, it is preferred that the freeness of the nanofibers is 350 or less. More preferred is 200 or less, and further more preferred is 100 or less. It is preferred that the lower limit of freeness is 5 or more. Moreover, if such nanofibers are used, a synthetic paper can be produced even if the weight per unit area is as very low as 2 g/m$^2$ as described in Example 33 given later. The nanofiber synthetic paper of Example 33 given later is based on a screen woven fabric, but the nanofibers existing in the meshes of the screen woven fabric, i.e., in the meshes of lattice do not form large pinholes even though there is no binder, and the sheet is uniformly even.

Furthermore, since the single fiber diameters of the disarranged nanofibers in the synthetic paper are uniform, the pores formed among the nanofibers of the synthetic paper are also uniform in size. The formation of the pores is governed by the polymer used as the nanofibers and the rigidity of nanofibers depending on the single fiber diameter. That is, since the nanofibers are bent, the pores are formed by the positions of the nanofibers existing in the synthetic paper, the diameters of the nanofibers and the entanglement among the nanofibers. The average pore diameter is several to about 10 times the single fiber diameters of the nanofibers. For example, to efficiently collect the fine particles or a component desired to be removed from a fluid such as a gas or liquid, it is preferred that the pore area of the nanofiber synthetic paper is 1.0 µm² (pore diameter 1.1 µm) or less. More preferred is 0.5 µm² (average pore diameter 0.75 µm) or less. It is preferred that the lower limit of pore area is 10 nm² or more, and more preferred is 50 nm² or more.

Moreover, in the nanofiber synthetic paper, the pore diameters are on the nanometer level, but it is also another feature of the synthetic paper that the irregularity of pore diameters is small. Since the irregularity of pore diameters is small, various fine particles (generally refer to dusts, foreign matters, various proteins, bacteria, etc.) can be classified. Even if a synthetic paper of nanofibers is used to merely produce a filter with pore diameters of nanometer size, clogging may occur soon. So, it may be necessary to employ, for example, an adsorption method in which a gas or liquid is made to flow in parallel to the surface of the synthetic paper. Anyway, the uniformly very fine pores of the nanofiber synthetic paper are expected to exhibit any function using the collection performance on the nanometer level.

It is preferred that the nanofiber synthetic paper has an air permeability of 30 cc/cm²/sec or less. If the synthetic fiber has a low air permeability, i.e., a high gas impermeability, it can be used, for example, as a partition wall such as a separator. A more preferred air permeability is 15 cc/cm²/sec or less, and further more preferred is 5 cc/cm²/sec or less. The most preferred is 1 cc/cm²/sec or less. It is preferred that the lower limit of air permeability is 0.25 cc/cm²/sec or more.

The synthetic paper also has a feature that since the voids in the synthetic paper are densely packed with the disarranged nanofibers, the pinholes through the synthetic paper are inhibited. More particularly, it is preferred that the number of pinholes with an equivalent diameter of 50 µm or more penetrating from the front surface to the back surface of the paper is 0 to 1000 holes/cm². If the number of pinholes is kept at 1000 holes/cm² or less, the air permeability, liquid permeability, etc. can be kept low. A more preferred number of pinholes is 100 holes/cm² or less, and a further more preferred number is 15 holes/cm² or less. The most preferred number is 3 holes/cm² or less.

It is preferred that the synthetic paper has a surface smoothness of 300 seconds or more. The surface smoothness in this case refers to the surface smoothness (in seconds) measured by the Bekk method specified in JIS P 8119-1976. If the surface smoothness is high, the nanofiber synthetic paper can be used in an application requiring smoothness such as a circuit board using insulating paper. A more preferred surface smoothness is 1000 seconds or more, and a further more preferred smoothness is 1500 seconds or more. A still further more preferred smoothness is 3000 seconds or more. It is preferred that the upper limit of the surface smoothness is 20000 seconds or less.

A mixed fiber synthetic paper consisting of disarranged nanofibers with a number average single fiber diameter of 500 nm or less and at least 5 wt % or more of other fibers with a number average single fiber diameter of 1 µm or more can also be produced. It is preferred that the disarranged nanofibers have a number average single fiber diameter of 200 nm or less. The mixing weight rate of nanofibers can be measured according to "T. Method for measuring the mixing weight rate of nanofibers" described for the examples given later. If disarranged nanofibers and other fibers with a single fiber diameter of 1 µm or more are mixed to form a paper sheet, the nanofiber synthetic paper obtained can be made bulky.

If the bulkiness of the nanofiber synthetic paper is controlled for example, the migration of a slight amount of a liquid such as circulating liquid or the permeability of ions can be controlled for use as a battery separator or a medical product, to improve the functional performance of nanofiber synthetic paper. It is preferred that the content of the other fibers of 1 µm or more to be mixed with the nanofibers is 5 wt % or more. More preferred is 10 wt % or more.

Furthermore, a mixed fiber synthetic paper consisting of 3 wt % or less of disarranged nanofibers with a number average single fiber diameter of 500 nm or less and other fibers with a number average fiber diameter of 0.1 µm or more can also be produced. It is preferred that the number average single fiber diameter of the disarranged nanofibers is 200 nm or less. Moreover, it is more preferred that the content of the nanofibers is 1 wt % or less. This mixed fiber synthetic paper is different from the mixed fiber synthetic paper described before. It is a synthetic paper characterized in that a small amount of disarranged nanofibers are added to a synthetic paper mainly composed of other fibers of 1 µm or more. Since the synthetic paper composed of other fibers of 1 µm or more is more bulkier and larger in voids than a synthetic paper composed of 100% nanofibers, the former synthetic paper is more excellent in air permeability, liquid permeability and pressure resistance. So, if disarranged nanofibers are mixed with the other fibers of 1 µm or more to make a mixed fiber synthetic paper, the performance as a synthetic paper can be sufficiently exhibited while the function of nanofiber surfaces can be used. Furthermore, the disarranged nanofibers are likely to cohere with each other. So, if a small amount of nanofibers are dispersed like a spider's web in the space of the synthetic paper produced by the other fibers of 1 µm or more, individual nanofibers are spread in the space and held in the synthetic paper. In this state, the nanofibers can easily exhibit their functions. If this mixed fiber synthetic paper is used as a catalyst carrier for biotechnology or chemical application or battery application, etc., it is expected that the surface area of nanofibers can be efficiently used.

A nanofiber synthetic paper in which disarranged nanofibers with a number average single fiber diameter of 500 nm or less, preferably 200 nm or less are laminated on a substrate can also be produced. If disarranged nanofibers are laminated on a substrate, the reinforcing effect by the substrate can improve the strength of the synthetic paper of this invention. In addition, if a small amount of disarranged nanofibers are laminated on a substrate, the efficiency of collecting various substances by nanofibers can be enhanced while the gas or liquid permeability can be controlled. So, such a synthetic paper can be used as a filter, etc. As for the lamination method, a papermaking technique can be used, or the substrate can be impregnated with a dispersion of nanofibers, or the dispersion can be added dropwise to the substrate, or the substrate can be sprayed or coated with the dispersion. Other methods can also be used. As the substrate, a woven fabric, knitted fabric, nonwoven fabric, foam or the like can be adequately selected for each application or purpose.

A compound synthetic paper containing the aforesaid nanofiber synthetic paper or a molded synthetic paper can also be produced. Furthermore, the nanofiber synthetic paper can be used to produce a filter, separator, abrasive, medical product or circuit board.

As described in the text and examples, a nanofiber synthetic paper can be produced without using a binder. A natural pulp can be processed into paper without using a binder, since the fibers are branched. Various methods have been studied to make paper by fibrillating, for example, a thermoplastic polymer, but it has been very difficult to make paper without using a binder. Furthermore, it has been difficult to make paper even from the conventional ultrafine fibers with a very small number average single fiber diameter of 0.5 µm or more without using a binder.

As described before, since the disarranged nanofibers can cohere with and be entangled with each other, paper can be made from them like a natural pulp, and a synthetic paper can be produced from them without using a binder. Furthermore, as described in Example 32 given later, disarrange nanofibers can be used as a binder to make paper from ordinary synthetic fibers or ultrafine fibers, and disarranged nanofibers can also be used as a binder to make a synthetic paper from synthetic thermoplastic polymer fibers with a number average single fiber diameter of 1 µm or more.

The method for producing a nanofiber synthetic paper will be described below.

At first, the method for preparing a dispersion as a raw material used for making the nanofiber synthetic paper will be described.

Beaten nanofibers, water, and as required, a dispersing agent and other additives are dispersed in a stirrer to a predetermined concentration. Though depending on the single fiber diameter of nanofibers and the weight per unit area of the synthetic paper to be produced, the disarranged nanofibers have a large specific surface area and the hydrogen bond force and intermolecular force acting among the nanofibers are large. So, the nanofibers are likely to cohere with each other. To prevent the cohesion, it is preferred to disperse the nanofibers at a concentration as low as possible. From the viewpoint of uniformly dispersing the nanofibers in the dispersion, it is preferred that the nanofiber concentration in the dispersion is 0.01 to 1 wt %. Furthermore, if the disarranged nanofibers are used to directly form a paper sheet, a heterogeneous synthetic paper may be produced. So, it is preferred to add a dispersing agent into the slurry. The dispersing agent can be adequately selected from anionic, cationic and nonionic dispersing agents in reference to the polymer used as the nanofibers and its properties, but since even a dispersing agent with the same structure is affected by its molecular weight, nanofiber concentration and other compounding ingredients, dispersing agents can be selectively used in response to the polymer used as the nanofibers and the purpose or application of the product. The principles for selecting an adequate dispersing agent are as described before.

Furthermore, it is preferred that the concentration of the dispersing agent added is 0.01 to 1.0 wt %. A more preferred range is 0.05 to 0.5 wt %. In the case where the conventional ultrafine fibers of 1 µm or more are used alone for forming a paper sheet, papermaking is difficult since the fibers cannot be entangled with each other. However, in the case of nanofibers, the nanofibers can be used alone to form a paper sheet, and in this case, in view of papermaking properties and higher paper strength, it is preferred that the weight per unit area of the nanofiber synthetic paper is 50 g/m² or less. More preferred is 30 g/m² or less. A further more preferred range is 10 g/m² to 0.05 g/m². If the single fiber diameter of nanofibers is relatively small and the dispersibility is good, then a weight per unit area of 2 g/m² or less is also possible. Furthermore, in the case where nanofibers are used alone to form a paper sheet, it is preferred that the fiber-length is rather long, for example, 1 to 6 mm. A more preferred range is 2 to 3 mm.

Moreover, as required, when a nanofiber synthetic paper is produced, a binder can be used. In the case where fibers are used as a binder, preferred are a natural pulp {wood pulp, hemp pulp, paper mulberry (*Broussonetia kazinoki*), mitsumata (*Edgeworthia papyrifera*), etc.} or meltable fibers containing a low melting point component or low softening point component are preferred, and PE or PP based fibers, PLA based fibers, PS based fibers, copolyamide based fibers and copolyester based fibers, and sheath-core conjugate fibers using a meltable component as their sheath component. Furthermore, in the case where a nanofiber synthetic paper is obtained by removing the sea component from a synthetic paper composed of "polymer alloy fibers", it is preferred to use binder fibers resistant against the liquid reagent and solvent. The number average single fiber diameter of generally commercially available binder fibers is usually as thick as more than 10 µm. So, in order to obtain a dense paper sheet, it is preferred to use ultrafine fibers with a single fiber diameter of 1 to 10 µm as binder fibers. It is also preferred to use a suitable resin based binder. Preferred resins include polyurethane based resins, polyphenol based resins, polyacrylic acid based resins, polyacrylamide based resins, epoxy based resins, silicone based resins, and vinylidene fluoride based resins. The slurry with nanofibers dispersed in it can further contain a modifier and additives for improving such properties as strength, tear resistance, abrasion resistance, antistatic property, surface luster, flexibility and hand.

As the method for making a synthetic paper from such nanofibers, a dispersion (slurry) having nanofibers dispersed in it is supplied into a slurry box of an ordinary paper machine, to make paper. As the paper machine, any of Fourdrinier paper machine, twin wire paper machine and cylinder paper machine can be used for making a synthetic paper, and an adequate paper machine can be used suitably for each application and purpose. In view of the properties of paper machines, in the case where it is desired to make paper with a relatively large weight per unit area, it is preferred to use a Fourdrinier paper machine, and in the case where it is desired to make thin paper with a relatively small weight per unit area, it is preferred to use a cylinder paper machine. For experimental small-scale papermaking, a commercially available square sheet machine or the like can be used for papermaking. A nanofiber slurry is supplied into a 25 cm square vessel, and a metallic screen filter is used for suction filtration, to form a wet sheet that is then dehydrated and dried to obtain a nanofiber synthetic paper.

Particular examples and processed product examples of compound solutions, emulsions, gels and synthetic papers using the nanofibers of this invention are described below. However, this disclosure is not limited thereto or thereby.

EXAMPLES

Selected representative aspects of this invention will be described below in detail in reference to examples. In the examples, the following measuring methods were used. The measured results of examples and comparative examples are collectively shown in Tables 3 to 9.

A. Melt Viscosity of Polymer

Toyo Seiki Capillograph 1B was used to measure the melt viscosity of the polymer concerned. The residence time of the polymer from supply of the sample to start of measurement was 10 minutes.

B. Melting Point

Perkin Elmer DSC-7 was used. The peak top temperature showing the melting of the polymer concerned in the $2^{nd}$ run was identified as the melting point of the polymer. The heating rate was 16° C./min, and the amount of the sample as 10 mg.

C. Color Tone (b*Value)

Minolta Spectrophotometer CM-3700d was used as the color tone meter, and the b* value of the sample concerned was measured. The light source was $D_{65}$ (color temperature 6504K), and measurement was performed with a visual field of 10°.

D. Mechanical Properties of Polymer Alloy Fibers

Ten meters of sample fibers were taken from the nonwoven fabric concerned, and the weight was measured five times (n=5). From the average value, the fineness (dtex) was obtained. At room temperature (25° C.), with the initial sample length of 200 mm and at a stress rate of 200 mm/min, the load-elongation curve was obtained under the conditions shown in JIS L 1013. Then, the load value at breaking was divided by the initial fineness to obtain the strength, and the elongation at breaking was divided by the initial sample length, to obtain the elongation. In this way, the strength-elongation curve was obtained.

E. Uster Unevenness of Polymer Alloy Fibers (U %)

Uster Tester 4 produced by Zellweger Uster was used to measure the Uster unevenness in the normal mode at a fiber feed rate of 200 m/min.

F. Cross Section Observation of "Polymer Alloy Fibers" by TEM

A very thin slice of fibers was cut in the cross sectional direction and the cross section of fibers was observed by a transmission electron microscope (TEM). Meanwhile, nylon was dyed with phosphorus tungstic acid.

TEM: Model H-7100FA produced by Hitachi, Ltd.

G. Number Average Diameter of Island Component Fibers (Nanofiber Precursors) in "Polymer Alloy Fibers"

The number average diameter of the island component fibers concerned was obtained as follows. A cross sectional photograph of the island component fibers obtained by TEM was processed using image processing software (Winroof), to measure the diameters of three hundred island fibers selected at random from the same cross section, and to calculate the sum of the diameters, and the sum was divided by the number of the island fibers, to obtain the simple average value. This calculation was performed at five places apart from each other by 10 m in the length of the "polymer alloy fibers", and the diameters of 1500 island fibers in total were measured. The average diameter of them was employed as the "number average diameter of island component fibers".

H. SEM Observation of Nanofibers

In the case of a nanofiber compound solution or emulsion, the solution was sampled and placed on a film or glass sheet, being dried at 60° C. From a dried arbitrary place, a sample of 5 mm square was taken, and platinum was vapor-deposited on it. An ultra high resolution field emission scanning electron microscope (UHR-FE-SEM) produced by Hitachi, Ltd. was used to observe the nanofibers in the sample. For a gel, in the case where the gel could be measured since it was stable in form, it was dried, and platinum was vapor-deposited on it, for observation by SEM. When the form was not stable, an adequate solvent was used to dissolve it, and according to the same method as described above, the nanofibers were observed.

In the case of a nanofiber synthetic paper, ten 10 cm square sheets of synthetic paper were cut out from arbitrary places of the synthetic paper, and a 5 mm square sample was taken at an arbitrary place of each of the synthetic paper sheets. Platinum was vapor-deposited on it, and an ultra high resolution field emission scanning electron microscope (UHR-FE-SEM) produced by Hitachi, Ltd. was used to observe the surface of the synthetic paper.

I. Number Average Single Fiber Diameter $\phi m$ of Nanofibers

The number average single fiber diameter $\phi m$ was obtained as described below. The nanofiber surface photograph taken in the above item H was processed using image processing software (Winroof), to measure the diameters of 30 single fibers selected at random in a 5 mm square sample and to calculate the sum of the diameters, and the sum was divided by the number of single fibers, to obtain a simple average value. This calculation was performed 10 times in total, to obtain the diameters of 30 single fibers each time, and the simple average value of the diameters of 300 single fibers in total was employed as the "number average single fiber diameter $\phi m$".

J. Evaluation of the Sum Pa of Single Fiber Ratios of Nanofibers

For the sum Pa of single fiber ratios, the data measured in the above item I was used, and the sum was obtained from the formula (3). A larger Pa value means smaller irregularity.

K. Evaluation of the Index Pb of Extremal Coefficient of Single Fiber Diameters of Nanofibers For the index Pb of extremal coefficient of single fiber diameters, the data measured in the above item I was used, and the index was calculated from the formula (5). The index indicates the degree to which single fibers with diameters close to the number average single fiber diameter are concentrated, and a higher index Pb value means smaller irregularity.

L. Freeness Test Method of Nanofibers

The freeness was measured using a Canadian freeness tester produced by Kumagaya Riki Kogyo Co., Ltd. according to the Canadian Standard Freeness Test Method of JIS P 8121 "Freeness Test Method of Pulp". One liter of an aqueous solution containing 0.30±0.05% of nanofibers was accurately weighed in a 20° C. room, and it was supplied into the Canadian freeness tester. This measurement was performed three times, and the measured values were simply averaged. The correction table of said JIS was used to correct data for the deviations from the concentration of 0.30%, and the corrected value was employed as the freeness.

M. Index of Moisture Retention ($\Delta$WR10)

About one point zero gram of test fibers were taken, and were washed with a detergent or solvent to remove the oil content, washed with water, dried, humidified at 20° C. and 65% humidity for 24 hours, and accurately weighed (W0). The fibers were immersed in water for 12 hours and taken out, and dehydrated to a water content of 60%±10% by a centrifuge or dehydrator. A balance was placed in a transparent box humidified to 20° C. and 25% humidity, and a plastic container with a diameter of 5 cm and a height of 1 cm was placed on the balance. The test fibers were placed in the plastic container and dried to decrease their weight, while the weight (Wi) of the fibers was measured every minute till the water content became 10% or less. The water content WRi (%) at each time point is expressed by the following formula.

$$WRi = 100 \times (Wi - W0)/W0 \quad (7)$$

WRi values for respective time points were plotted as a graph, and a tangent at a WRi value of 30% was drawn. From the gradient $\Delta$WR30, "the water content decrease rate $\Delta$WR10 per 10 minutes" was calculated. This measurement was performed 5 times, and the measured values were simply averaged, to be employed as the index of moisture retention ($\Delta$WR10). The $\Delta$WR30 is the drying rate of fibers with a water content of about 30%, and a smaller value means better moisture retention. The water content of the skin is about 15 to 20%, and the index of moisture retention of fibers is calculated as the drying rate of fibers with a water content of 30%, considering the water content of the skin.

N. Index of Water Retention (WI)

About one point zero gram of test fibers were taken, and were washed with a detergent or solvent to remove the oil content, washed with water, dried, humidified at 20° C. and 65% humidity for 24 hours, and accurately weighed (W0). A 50-mesh stainless steel screen (weight Ws) with a size of 5 cm×10 cm having a 6 mm wide 2 mm thick metallic frame attached was fixed at an inclination of 45°. The fibers were immersed in water for 12 hours, taken out, placed on the stainless steel screen, and allowed to stand in an environment of 20° C. and 65% humidity for 2 minutes. The weight of the screen with the fibers on it (Wt) was measured. The index WI of water retention is expressed by the following formula.

$$WI=100\times(Wt-Ws)/W0 \quad (8)$$

A larger index of water retention means better water retention.

O. Settling Time (Evaluation of Dispersion-Stability)

A fiber solution was placed in a sample bottle with a diameter of 30 mm, a height of 10 cm, a stopper and a flat bottom up to a height of 8 cm, and the bottle was sufficiently shaken by hand for stirring the solution, and was allowed to stand. A red line was marked on the sample bottle at a height of 4 cm from the bottom. At the time point when the fibers in the solution stopped rotation, a stop watch was pressed, and the settling fibers were observed in an environment of 20° C. The time Ts when the upper surface of existing nanofibers reached the red line was employed as the settling time. A longer time means better dispersion stability.

P. Transparency

Pure water was placed in the standard sample cell of spectrophotometer U-3400 produced by Hitachi, Ltd. and a test solution was placed in the other cell. The average transmissivity Tr was measured using a light source with a wavelength of 500 nm. A higher transmissivity means better transparency.

Q. Thickness of Synthetic Paper

Ten 10 cm square synthetic paper sheets were cut from arbitrary places of the nanofiber synthetic paper concerned, and the thickness of each sheet was measured at 10 places. The sheet was placed on a sample mount with a micrometer, and the thickness was measured by the micrometer at 20° C. and 65%. The sum of all the thickness values was simply averaged to obtain the thickness t (μm).

R. Weight Per Unit Area and Density of Synthetic Paper

Ten 10 cm square synthetic paper sheets were cut from arbitrary places of the nanofiber synthetic paper concerned, and the weight (g) of each sheet was measured at 20° C. and 65%. The average weight of five sheets was divided by 0.01 m², to calculate the weight per unit area M (g/m²). Furthermore, the value of the weight per unit area M was divided by the thickness value in cm obtained from the average thickness measured above, to calculate the average density (g/cm³).

S. Pore Area of Synthetic Paper

The average pore area of synthetic paper was obtained as described below. In the SEM observation of item H, the magnification of the SEM photograph used for evaluation of pore area is the magnification K (magnification within ±30%) expressed by the following formula, where ϕm (nm) is the number average single fiber diameter.

$$K=2500000/\phi m \quad (9)$$

On the SEM photograph taken at the above magnification K, a square frame with a length per side of 50 mm (constant irrespective of the magnification) is drawn at an arbitrary place. Furthermore, the fiber image in the frame was introduced into image processing software (Winroof), and arbitrary eight or more luminance distribution measuring lines were placed on the introduced fiber image at equal intervals. Then, luminance distribution of the respective fibers was measured for binarizing the image. Ten fibers higher in surface luminance were selected, and the luminance values were averaged as the average high luminance Lh. With the luminance corresponding to 50% of the average high luminance Lh as the threshold value Lu, the fibers of luminance Lu or lower were deleted by image processing (threshold function) (as a result of this processing, the pores near the surface portion were selected). All the areas Ai (nm²) surrounded by the selected fibers were measured by image processing (by either manual work or computerized automatic operation). In this case, the pores with an area corresponding to not larger than 64% (nm²) of the square of the number average single fiber diameter were excluded from all the area data. The areas Ai of the pores remaining after excluding the above pores were totalized, and the sum was divided by the number n of remaining pores, to calculate the average pore area.

T. Method for Measuring the Mixing Weight Rate of Nanofibers

To obtain the mixing weight rate of nanofibers in a compound synthetic paper or mixed fixed synthetic paper respectively containing nanofibers, a section of the synthetic paper concerned was observed by an ultra high resolution field emission scanning electron microscope (SEM) for evaluation. At first, the synthetic paper was embedded in an embedding resin (epoxy resin, curable polyester resin, etc.), and the sample having the synthetic paper embedded was cut by a diamond cutter or microtome to expose a section of the synthetic paper. The cut surface of the sample was ground by sand paper or abrasive, washed with water sufficiently and dried at low temperature. Platinum was vapor-deposited on the sample, and a sectional photograph of the synthetic paper was obtained using an ultra high resolution field emission scanning electron microscope produced by Hitachi, Ltd. At first, the fibers in the photograph were classified into nanofibers with a diameter of 500 nm or less and the other fibers with a number average single fiber diameter of 1 μm or more in the synthetic paper. In this case, the fibers with a single fiber diameter of more than 0.5 μm were classified as part of the other fibers with a number average single fiber diameter of 1 μm or more.

On the sectional photograph, the sectional areas of the individual fibers classified as nanofibers and as the other fibers were measured using image processing software (Winroof), and the sectional areas were further totalized. The total area of the nanofibers was expressed as Sn, and the total area of the fibers of 0.5 μm or more, as Sf. Furthermore, the specific gravity of the nanofibers was expressed as ρn, and the specific gravity of the fibers of more than 0.5 μm, as ρf, the mixing weight rate of the nanofibers, as α (%), and the mixing weight rate of the other fibers of 1 μm or more, as β (%). The mixing weight rates were calculated from the following formulae:

If A=Sn×ρn, B=Sf×ρf, then $$\alpha=A/A+B\times100 \quad (9)$$

$$\beta=B/A+B\times100 \quad (10)$$

Meanwhile, the samples for evaluation were taken at five arbitrary places from the synthetic paper concerned, and the value of α or β was obtained 5 times by the above method. The average value of the obtained values was employed as the mixing weight rate of the nanofibers or the other fibers.

U. Air Permeability of Synthetic Paper

The air permeability of the synthetic paper concerned was measured according to JIS 1096 "Method for Testing the Air permeability of Woven Fabric under Constant Pressure" using a Frazier type air permeability tester. Five 10 cm square sheets were cut from arbitrary places of the nanofiber synthetic paper, and the air permeability (cc/cm$^2$/sec) values of the respective sheets were measured at 20° C. and 65% and simply averaged.

V. Mechanical Properties

Five 2 cm wide 18 cm long sheets were cut from arbitrary places of the nanofiber synthetic paper concerned, and a tensile test was performed according to JIS L 1013 with an initial sample length of 10 cm at a stress rate of 20 cm/min. The load value obtained at the of breaking during test was divided by the initial paper width, and the quotient was employed as the strength (N/cm). On the other hand, the elongation obtained at the time of breaking during test was divided by the initial sample length, and the quotient was employed as the elongation (%). These property values were measured from 10 synthetic paper sheets and simply averaged.

W. Hygroscopicity (AMR)

About one to two grams of a synthetic paper sample was weighed, placed in a weighing bottle, kept at 110° C. for 2 hours, for being dried, and weighed (W0). Then, a control was kept at 20° C. and 65% RH for 24 hours, and weighed (W65). It was kept at 30° C. and 90% RH for 24 hours, and weighed (W90). The hygroscopicity was obtained from the following formulae:

$$MR65=[(W65-W0)/W0]\times 100\% \quad (11)$$

$$MR90=[(W90-W0)/W0]\times 100\% \quad (12)$$

$$\Delta MR=MR90-MR65 \quad (13)$$

X. Weight Loss Rate of Polymer

TG/DTA6200 produced by Seiko Instruments Inc. was used to heat the sample concerned from room temperature to 300° C. at a heating rate of 10° C./min in nitrogen atmosphere and subsequently the sample was kept at 300° C. for 5 minutes, to measure the weight loss rate.

Y. Measurement of Area Ratio of Nanofibers

A cross section of a nanofiber bundle obtained by removing the sea component from polymer alloy fibers was observed by TEM. The cross sectional area of the fiber bundle as a whole was expressed by (Sa) and the sum of the cross sectional areas of individual nanofibers of 1 to 500 nm existing in the fiber bundle, as (Sb), the area ratio of nanofibers was obtained from the following formula.

$$\text{Area ratio of nanofibers (\%)}=(Sb/Sa)\times 100 \quad (14)$$

Z. Surface Smoothness

The surface smoothness (in seconds) was measured by the Bekk method specified in JIS P 8119-1976.

A1. Evaluation of Pinholes of Synthetic Paper

In the SEM observation at item H, the synthetic paper was observed at a magnification of 500-fold or less, and the number of pores with an equivalent diameter of 50 μm or more existing within a range of 100 μm$^2$ on the photograph was counted. This was performed in 10 visual fields, and the numbers were simply averaged. The number per 1 cm$^2$ was obtained by calculation.

B1. Measurement of Zeta Potential 0.001 M of KCl was added to a nanofiber complex solution or dispersion beforehand, and an electrophoretic light-scattering photometer ELS-800 (produced by Otsuka Electronics Co., Ltd.) was used to measure the zeta potential at pH 7.

Example 1

Production of "Polymer Alloy Fibers", Beating of Nanofibers by a Commercially Available Beater, and Production of a Nanofiber Compound Gel Twenty weight percent of N6 with a melt viscosity of 53 Pa·s (262° C., shear rate 121.6 sec$^{-1}$) and with a melting point of 220° C., and 80 wt % of a copolymerized PET with a melting point of 225° C. and with a melt viscosity of 310 Pas (262° C., shear rate 121.6 sec$^{-1}$) obtained by copolymerizing 8 mol % of isophthalic acid and 4 mol % of bisphenol A were kneaded using a two-screw extrusion kneader at 260° C., to obtain polymer alloy chips with a b* value of 4. The copolymerized PET had a melt viscosity of 180 Pa·s at 262° C. and 1216 sec$^{-1}$. The kneading conditions in this case were as follows. As the polymers, N6 and the copolymerized PET were separately weighed and separately supplied to the kneader. The screws used had a diameter of 37 mm, effective length of 1670 mm and L/D of 45.1. The kneading temperature was 260° C.

The model drawing of the melt spinning apparatus used for melt spinning is shown in FIG. 1. In the drawing, symbol 1 denotes a hopper; 2, a melting portion; 3, a spin block; 4, a spin pack; 5, a spinneret; 6, a chimney; 7, melt-discharged filaments; 8, a filament-collecting finishing guide; 9, a first take-up roller; 10, a second take-up roller; and 11, a wound yarn.

The polymer alloy chips were molten at the melting portion 2 of 275° C. and introduced into the spin block 3 with a spinning temperature of 280° C. The polymer alloy melt was filtered by a nonwoven metallic fabric with a max filtration diameter of 15 μm, and melt-spun from the spinneret 5 with a spinneret face temperature of 262° C. The spinneret used in this case had a metering portion with a diameter of 0.3 mm above the discharge holes and had a discharge hole diameter of 0.7 mm and a discharge hole length of 1.75 mm. The discharge rate per hole in this case was 2.9 g/min. Furthermore, the distance from the bottom face of the spinneret to the cooling start point (the top end of the chimney 6) was 9 cm. The discharged filaments were cooled and solidified for 1 m by cooling air of 20° C., and oiled by the oiling guide 8 installed at 1.8 m below the spinneret 5, passing around the non-heated first take-up roller 9 and the second take-up roller 10, to be wound at 900 m/min. The spinnability in this case was good, and during continuous spinning for 24 hours, no yarn breaking occurred. The fibers were drawn and heat-treated with the temperature of a first hot roller kept at 98° C. and with the temperature of a second hot roller kept at 130° C. In this case, the drawing ratio between the first hot roller and the second hot roller was set at 3.2 times. The "polymer alloy fibers" were obtained as 12 filaments of 120 dtex and had excellent properties of 4.0 cN/dtex strength, 35% elongation and 1.7% Uster unevenness. Furthermore, a cross section of the obtained "polymer alloy fibers" was observed by TEM, and found to have an islands-in-sea multi-component structure with N6 as the island component (round portions) and with the copolymerized PET as the sea component (the other portion) (see FIG. 2). The diameter of N6 island fibers was 53 nm, and "polymer alloy fibers" with N6 island fibers very finely dispersed could be obtained.

The "polymer alloy fibers" obtained as 12 filaments of 120 dtex were cut by a guillotine cutter to 2 mm. The cut "polymer alloy fibers" were treated by 10% sodium hydroxide of 98° C. for 1 hour, to remove the polyester component as the sea component, and the remaining island fibers were collected by a filter and dehydrated to a water content of about 100% by a centrifuge, to obtain short fibers. The short fibers were washed with water and dehydrated respectively five times repetitively to remove sodium hydroxide, for obtaining short nanofibers as an aggregate. About 20 liters of water and 30 g of the short fibers were supplied into a Niagara beater, and the fibers were beaten in the first step for 10 minutes. The freeness of the first-step-beaten nanofibers was 362. The fibers were dehydrated by a centrifuge, to obtain 250 g of first-stepbeaten fibers with a fiber concentration of 12 wt %. The first-step-beaten fibers were beaten in the second step by a PFI mill for 10 minutes, and dehydrated, to obtain 250 g of second-step-beaten fibers with a nanofiber concentration of 10 wt %. The freeness of the second-step-beaten nanofibers was 64. The amount of water contained in the nanofibers of 10 wt % in concentration was more than 10 times the quantity of nanofibers, but even if they were put in a reagent bottle and shaken, they did not act like a liquid, but acted like a soft solid gel. To evaluate the configuration of the nanofibers in the gel, as described in Example 6, the gel was diluted with water, to prepare 0.01 wt % nanofiber compound solution, and the number average single fiber diameter $\phi$m, the sum Pa of single fiber ratios, and the index Pb of extremal coefficient of single fiber diameters were measured. The distribution of single fiber diameters is shown in Table 3. The nanofibers in the nanofiber compound gel were 60 nm in $\phi$m, 100% in Pa and 66% in Pb.

Examples 2 and 3

Nanofiber compound solutions obtained by beating a nanofiber aggregate for a long period of time using a laboratory blender Seven point zero grams (weight as dry fibers; water content 110%) of the short nanofiber aggregate with a fiber length of 2 mm obtained by removing the sea component from the "polymer alloy fibers" of Example 1 and water were added into a laboratory blender up to 500 cc. The mixture was (1) dispersed at 6000 rpm for 30 minutes by the laboratory blender and (2) filtered by a 50-mesh stainless steel screen, to obtain a solution. The nanofibers on the stainless steel screen were returned into water, and furthermore, the operations of (1) and (2) were repeated three times. As a result, about 1.0 wt % nanofiber compound solution was obtained. Ten grams of the compound solution was placed in a vat, and the water was evaporated in a dryer. The fiber concentration was measured and found to be 1.1 wt %. Moreover, water was added to prepare 1.0 wt % nanofiber compound solution. The solution corresponds to the state of 1.0 wt % fibers obtained after the second step beating of Example 1. The freeness of the nanofibers was 157. The freeness was higher than that of the nanofibers obtained after the second step beating of Example 1. Though the beating capability of the laboratory blender was rather lower, since stirring was repeated for a long period of time, well dispersed nanofibers could be obtained. Seventy grams of the 1.0 wt % nanofiber compound solution and water were added into a laboratory blender up to 500 cc, and the mixture was dispersed at 6000 rpm for 30 minutes, to lower the nanofiber concentration. Thus, 0.10 wt % nanofiber compound solution was obtained (Example 2).

Furthermore, the 0.10 wt % compound solution was processed as described for Example 2, for being diluted to 10 times. Thus, 0.01 wt % nanofiber compound solution was obtained (Example 3). The $\phi$m, Pa and Pb values of the compound solutions of Examples 2 and 3 were measured and found to be 63 nm ($\phi$m), 100% (Pa) and 61% (Pb) respectively. It can be seen that compound solutions with nanofibers dispersed to the same degrees as in Example 1 could be obtained though a laboratory blender was used for beating. Furthermore, the dispersion stability of the nanofibers was evaluated. The settling time was fount to be 12 minutes (Example 3), and it was long compared with 2.7 minutes (Comparative Example 2) of ordinary fibers (diameter 27 µm) and 1.1 minutes (Comparative Example 4) of ultrafine fibers (diameter 2 µm), showing good dispersion stability. The nanofibers that settled could also be easily re-dispersed by stirring. Furthermore, the transparency values of the compound solutions of Examples 2 and 3 were 1.8% and 53% respectively, being about the same as the transparency of Example 6 in which the nanofiber compound gel beaten in Example 1 was diluted. The freeness values of Examples 2 and 3 were rather higher than that of Example 1, being rather poor in the beating degree of nanofibers, but $\phi$m, Pa and Pb values were about the same as those of Example 1, showing that the nanofibers could be dispersed even when a laboratory blender was used for beating.

Comparative Examples 1 and 2

Aqueous Solutions of Ordinary Fibers with a Diameter of 27 µm

Commercially available nylon fibers with a number average single fiber diameter of 27 µm were cut to 2 mm, and 0.7 g of the fibers and water were added into a laboratory blender up to 500 cc, and the mixture was dispersed at 6000 rpm for 30 minutes by the laboratory blender and (2) filtered by a 50-mesh stainless steel screen, to obtain a solution. (3) The nanofibers on the stainless steel screen were returned into water and furthermore, the operations of (1) and (2) were repeated three times. As a result, an aqueous solution with a nylon fiber concentration of about 0.1 wt % was obtained. The fibers had not been beaten at all. Ten grams of the aqueous solution was placed in a vat, and the water was evaporated in a dryer. The fiber concentration was measured and found to be 0.13 wt %. Water was further added to prepare 0.10 wt % nylon fiber aqueous solution (Comparative Example 1). Seventy grams of the 0.10 wt % nylon fiber aqueous solution and water were added in a laboratory mixer up to 500 cc, and the mixture was dispersed at 6000 rpm for 30 minutes by the laboratory mixer, to lower the nylon fiber concentration, for obtaining 0.01 wt % nylon fiber aqueous solution (Comparative Example 2). The $\phi$m, Pa and Pb values of the aqueous solutions of Comparative Examples 1 and 2 were measured and found to be 27 µm (+m), 0% (Pa) and 92% (Pb) respectively, to show that the nylon fibers could not be beaten unlike the nanofibers of Example 2. Furthermore, the dispersion stability of the aqueous solution of Comparative Example 2 was evaluated in reference to the settling time, and the time was found to be 2.7 minutes, showing fast settlement, hence no good dispersion stability. Moreover, the transparency values of the aqueous solutions of Comparative Examples 1 and 2 were 66% and 87% respectively, showing good transparency. The reason is that since the diameter of the nylon fibers of Comparative Examples 1 and 2 was larger than the diameter of nanofibers, the number of nylon fibers per unit volume in the aqueous solution was very small.

Comparative Examples 3 and 4

Aqueous Solutions of Ultrafine Fibers with a Diameter of 2 µm

Islands-in-sea multi-component fibers were spun by the method described in JP53-106872A using nylon 6 (N6) with a melting point of 220° C. as the island component and polystyrene (PS) as the sea component, with the amount of N6 used as the island component as 60 wt %, and in succession they were drawn to obtain a drawn yarn of islands-in-sea multi-component fibers. Subsequently also as described in an example of aforesaid JP53-106872A, the drawn yarn was treated with trichloroethylene, to remove PS used as the sea component by more than 99%, for obtaining N6 ultrafine fibers with a diameter of about 2 μm. A cross section of the fibers was observed by TEM, and the ultrafine fibers were found to have a single fiber diameter of 2.2 μm. The N6 ultrafine fibers were cut to 2 mm, and 0.7 g of the fibers and water were added into a laboratory blender up to 500 cc. The mixture was (1) dispersed at 6000 rpm for 30 minutes by the laboratory blender and (2) filtered by a 50-mesh stainless steel screen, to obtain a solution. (3) The nanofibers on the stainless steel screen were returned into water, and the operations of (1) and (2) were further repeated three times. As a result, an aqueous solution with an N6 ultrafine fiber concentration of about 0.1 wt % was obtained, but the fibers formed large flocks of several millimeters, to 15 mm in the aqueous solution and could not be sufficiently dispersed in the aqueous solution. Ten grams of the aqueous solution was placed in a vat, and the water was evaporated in a dryer. The fiber concentration was measured and found to be 0.12 wt %. Furthermore, water was added to prepare 0.10 wt % N6 ultrafine fiber aqueous solution (Comparative Example 3). Seventy grams of the 0.10 wt % N6 ultrafine fiber aqueous solution and water were added into a laboratory blender up to 500 cc, and the mixture was dispersed at 6000 rpm for 30 minutes by the laboratory blender, to lower the nylon fiber concentration of the aqueous solution, for obtaining 0.01 wt % N6 ultrafine fiber aqueous solution (Comparative Example 4). The aqueous solution was small in the sizes of flocks compared with those of Comparative Example 3, but the fibers became clusters of 1 mm to 5 mm in the aqueous solution. Furthermore, the clusters were likely to cohere with each other, and when the aqueous solution was allowed to stand, N6 ultrafine fibers were likely to settle. The $\phi m$, Pa and Pb values of the 0.01 wt % N6 ultrafine fiber aqueous solution were measured and found to be 2.1 μm ($\phi m$), 0% (Pa) and 88% (Pb), showing that the nylon fibers could not be beaten unlike the nanofibers of Example 2. The dispersion stability of the 0.01 wt % nylon fiber aqueous solution of Comparative Example 4 was evaluated in reference to the settling time, and the time was found to be 1.1 minutes, showing very fast settlement, hence no good dispersion stability. The transparency values of the aqueous solutions of Comparative Examples 3 and 4 were 14% and 52% respectively.

Examples 4, 5 and 6

Production of Low Concentration Nanofiber Compound Solutions from the High Concentration Nanofiber Gel of Example 1

One hundred and fifty grams of the second-step-beaten 10 wt % nanofibers obtained in Example 1 were taken, and 850 g of water was added to them. The mixture was (1) dispersed at 6000 rpm for 5 minutes by a laboratory blender and (2) filtered by a 50-mesh stainless steel screen, to obtain a solution. (3) The nanofibers on the stainless steel screen were returned into water, and the operations of (1) and (2) were further repeated five times. As a result, about 1 wt % nanofiber compound solution was obtained. Ten grams of the solution was placed in a vat, and the water was evaporated in a dryer. The fiber concentration was measured and found to be 1.1 wt %. Water was further added to prepare 1.00 wt % nanofiber compound solution (Example 4). One hundred and fifty grams of the 1.00 wt % nanofiber compound solution was taken, and 850 g of water was added to it. After operations of (1), (2) and (3) {the operation frequency of (3) was 3 times}, the concentration was adjusted, to obtain 0.10 wt % nanofiber compound solution (Example 5). One hundred and fifty grams of the 0.10 wt % nanofiber compound solution was taken, and 850 g of water was added to it. After operations of (1), (2) and (3) {the operation frequency of (3) was 3 times}, the concentration was adjusted to obtain 0.01 wt % nanofiber compound solution (Example 6). The zeta potential of the nanofiber compound solution of Example 6 was measured and found to be −14 mV. The dispersion stability of the nanofiber compound solution of Example 6 was evaluated in reference to the settling time, and the settling time of the nanofibers in the nanofiber compound solution of Example 6 was found to be 10 minutes, showing good dispersibility of nanofibers, compared with the ordinary fibers of Comparative Example 2 and the ultrafine fibers of Comparative Example 4. Furthermore, the transparency values of the compound solutions of Examples 4, 5 and 6 were 0%, 1.2% and 51% respectively. The $\phi m$, Pa and Pb values of the nanofibers in the compound solution of Example 6 were measured and found to be 60 nm (+m), 100% (Pa) and 66% (Pb).

Examples 7, 8 and 9

Addition of a Dispersing Agent to the Nanofiber Compound Solutions of Examples 4, 5 and 6

An anionic dispersing agent containing sodium polyacrylate as the main ingredient (Shallol AN-103P produced by Dai-ichi Kogyo Seiyaku Co., Ltd.; molecular weight 10000) was added to the nanofiber compound solutions produced in Examples 4, 5 and 6 to achieve a concentration of 0.10 wt % respectively, and the mixtures were respectively stirred to obtain the compound solutions of Example 7, 8 and 9. The zeta potential of the nanofiber compound solution of Example 9 was measured and found to be −50 mV. The dispersion stability of the nanofiber compound solution of Example 8 was evaluated in reference to the settling time, and the settling time of the nanofiber compound solution of Example 8 was found to be 360 minutes, compared with 3.7 minutes achieved by the ordinary fibers of Comparative Example 5 and 1.3 minutes achieved by the ultrafine fibers of Comparative Example 6. In the comparison between Example 6 and Example 9, between Comparative Example 2 and Comparative Example 5, and between Comparative Example 4 and Comparative Example 6, the effect of adding a dispersing agent on the settling time was largest with the nanofiber compound solution. Compared with the conventional ordinary fibers and ultrafine fibers, nanofibers were remarkably improved in dispersibility (36 times compared with no addition) by the addition of the dispersing agent. Furthermore, the transparency values of the compound solutions of Examples 7, 8 and 9 were 0%, 2.4% and 63% respectively, to show that no effect of improving transparency was obtained in the 1.0 wt % nanofiber compound solution of Example 7 or in the 0.10 wt % nanofiber compound solution of Example 8. However, the 0.01 wt % nanofiber compound solution of Example 9 showed an effect of improving transparency by more than 10% due to the addition of the dispersing agent, compared with Example 6 in which no dispersing agent was added. In the case where the nanofiber concentration in the compound solution is high, since the number of nanofibers per unit volume of the compound solution is very large, the addition of a dispersing agent does not improve dispersibility so much. In the case where the transparency of a compound solution is necessary, it is preferred to control the number of nanofibers per unit volume of the compound solution, and it is preferred to keep the nanofiber concentration at 0.05 wt % or less.

Comparative Examples 5 and 6

Addition of a dispersing agent to the aqueous solutions of the conventional ordinary fibers and ultrafine fibers of Comparative Examples 2 and 4

An anionic dispersing agent containing sodium polyacrylate as the main ingredient (Shallol AN-103P produced by Dai-ichi Kogyo Seiyaku Co., Ltd.; molecular weight 10000) was added to the aqueous solutions prepared in Comparative Examples 2 and 4, to achieve a concentration of 0.10 wt %, and the mixtures were stirred to obtain the aqueous solutions of Comparative Examples 5 and 6. The dispersion stability of the aqueous solutions of Comparative Examples 5 and 6 was evaluated in reference to the settling times. The settling time of Comparative Example 5 was 3.7 minutes, and that of Comparative Example 6, 1.3 minutes, respectively showing faster settlement, hence no good dispersion stability.

Example 10

Nanofiber Compound Toilet Water (1)

The following compounding ingredients were added to the nanofiber compound solution prepared in Example 6, to prepare a nanofiber compound toilet water. Ten subjects were asked to use the toilet water as a sensory test. When they used the toilet water samples obtained by using the ordinary fibers with a diameter of tens of micrometers of Comparative Example 7 and the ultrafine fibers with a diameter of several micrometers of Comparative Example 8, ten subjects felt gritty with the former and nine subjects felt gritty with the latter. However, when they used the nanofiber toilet water, none of them felt any stress from the coating, and they could have a natural feel for it. Furthermore, the nanofiber toilet water was useful for improving rough skin and preventing sunburn, and furthermore did not flow with perspiration, being able to last long.

| | |
|---|---|
| Nanofiber compound solution of Example 6 | 86.5 wt % |
| Glycerol | 5.0 wt % |
| Allantoin | 0.3 wt % |
| Ethanol | 8.0 wt % |
| Ethyl parabenzoate | 0.2 wt % |
| Total | 100.0 wt % |

Comparative Examples 7 and 8

Toilet Waters Containing the Conventional Ordinary Fibers or Ultrafine Fibers

The following compounding ingredients were added to the aqueous solution of ordinary fibers with a diameter of 27 μm prepared in Comparative Example 2 and to the aqueous solution of ultrafine fibers with a diameter of 2.1 μm prepared in Comparative Example 4, to prepare toilet waters of Comparative Examples 7 and 8.

| | |
|---|---|
| Aqueous solution of Comparative Example 2 (Comparative Example 7) | 86.5 wt % |
| Aqueous solution of Comparative Example 4 (Comparative Example 8) | 86.5 wt % |
| Glycerol | 5.0 wt % |
| Allantoin | 0.3 wt % |
| Ethanol | 8.0 wt % |
| Ethyl parabenzoate | 0.2 wt % |
| Total | 100.0 wt % |

Example 11

Nanofiber Compound Toilet Water (2)

The nanofiber compound solution prepared in Example 5 and a commercially available toilet water {The Skin Care Hydrobalancing Softener (trade name) produced by Shiseido Co., Ltd.} were mixed at the following ratio by a laboratory stirrer for 3 minutes, to prepare a nanofiber compound toilet water. Ten subjects were asked to use the toilet water as a sensory test. None of them felt any stress from the coating when they used it, and they could have a natural feel for it. Furthermore, because of the nanofibers contained, the toilet water could be prevented from flowing with perspiration and could last long. Moreover, since nanofibers were mixed, the nanofibers were more entangled with each other to reduce the pore diameter. So, the moisture retention was good, and the moist feel of the skin after use of the toilet water was improved.

| | |
|---|---|
| Nanofiber compound solution of Example 5 | 10 wt % |
| The Skin Care Hydrobalancing Softener | 90 wt % |
| Total | 100 wt % |

Example 12

Nanofiber Compound Emulsion (1)

The following compounding ingredients were added to the nanofiber compound solution prepared in Example 5, to prepare an emulsion. The compounding method was as follows. At first, nanofibers, lecithin, propylene glycol and pure water were mixed, and the mixture was stirred to prepare solution A. Then, carboxyvinylpolymer was neutralized by part (0.4 wt %) of ethanolamine, to prepare solution B. Furthermore, oil ingredients such as stearic acid, glycerol monostearate, cetanol, liquid paraffin and squalane were mixed at 80° C., to prepare solution C. The remaining ethanolamine (1.0 wt %) was added to the solution A, and they were mixed at 80° C. Then, the solution C consisting of oil ingredients was mixed for emulsification, and furthermore the solution B was added to adjust the viscosity, for obtaining a nanofiber compound emulsion. The nanofiber compound emulsion was an emulsion good in homogeneous dispersion and long-term stability. Furthermore, 10 subjects were asked to use the emulsion as a sensory test. None of them felt any stress from the coating on the skin when they used it, and they could have a natural feel for it. The emulsion improved rough skin and did not flow with perspiration, being able to last long.

| | |
|---|---|
| Nanofiber compound solution of Example 5 | 10.0 wt % |
| Triethanolamine | 1.4 wt % |
| Lecithin | 0.2 wt % |

| | |
|---|---|
| Propylene glycol | 8.3 wt % |
| Methyl parabenzoate | 0.2 wt % |
| 1% carboxyvinylpolymer | 20.0 wt % |
| Stearic acid | 2.6 wt % |
| Glycerol monostearate | 1.0 wt % |
| Cetanol | 1.0 wt % |
| Liquid paraffin | 8.0 wt % |
| Squalane | 1.0 wt % |
| Pure water | 46.3 wt % |
| Total | 100.0 wt % |

Example 13

Nanofiber Compound Emulsion (2)

The nanofiber compound solution prepared in Example 5 and a commercially available emulsion {The Skin Care Night Essential Moisturizer (trade name) produced by Shiseido Co., Ltd.} were mixed at the following mixing ratio by a laboratory stirrer for 15 minutes, to prepare a nanofiber emulsion. Ten subjects were asked to use the emulsion as a sensory test. None of them felt any stress from the coating when they used it, and they could have a natural feel for it. Furthermore, since the nanofibers uniformly covered the skin surface and could seal the skin surface, they felt the skin was better kept moistened after use of the emulsion. Moreover, the nanofibers compounded could prevent the emulsion from flowing with perspiration and allowed the emulsion to last long.

| | |
|---|---|
| Nanofiber compound solution of Example 5 | 10 wt % |
| The Skin Care Night Essential Moisturizer | 90 wt % |
| Total | 100 wt % |

Example 14

Nanofiber Compound Foundation

The following compounding ingredients of group A were mixed by a high speed laboratory stirrer at 80° C., till they became homogeneous. Those of group B were also mixed by a low speed laboratory stirrer at 80° C., till they became homogeneous. The compounding ingredients of group B were mixed with those of group A, for emulsification. The nanofiber compound solution prepared in Example 4 was mixed with the emulsion, till they became homogeneous, and the mixture was cooled to obtain a nanofiber compound foundation. Ten subjects were asked to use the foundation as a sensory test. None of the subjects felt any stress from the coating when they used the foundation, and the foundation was favorably smooth when applied, was adaptable to the wrinkles and wrinkle creases of the skin, and was favorably adhesive to the skin. Furthermore, with regard to the touch during use, a good balance was realized between the comfortable air permeability to the skin by the nanofibers and the moisture retention by the sealing capability of numerous nanofibers. Furthermore, the foundation could last long due to such effects as fiber adhesion, water retention, moisture retention and air permeability, and was very unlikely to flow with perspiration.

| | |
|---|---|
| Nanofiber compound solution of Example 4 | 10.0 wt % |
| Group A | |
| Propylene glycol | 5.0 wt % |
| Butyl glycol | 8.0 wt % |
| Carboxyvinylpolymer | 0.3 wt % |
| Triethylamine | 0.5 wt % |
| Methylparaben | 0.1 wt % |
| Fine titanium oxide particles | 6.0 wt % |
| Talc | 1.5 wt % |
| Red iron oxide | 1.5 wt % |
| Iron oxide | 1.0 wt % |
| Pure water | 42.4 wt % |
| Group B | |
| Stearic acid | 2.6 wt % |
| Octyldodecyl myristate | 10.0 wt % |
| Cetanol | 1.0 wt % |
| Glycerol monostearate | 2.0 wt % |
| Liquid paraffin | 6.0 wt % |
| Squalane | 2.0 wt % |
| Propylene paraben | 0.1 wt % |
| Total | 100.0 wt % |

Example 15

Nanofiber Compound Oil Cream

The following compounding ingredients were added to the nanofiber compound solution prepared in Example 4, and the mixture was mixed at 40° C. by a low speed laboratory stirrer, till it became homogeneous, to prepare a nanofiber compound oil cream. Ten subjects were asked to use the oil cream as a sensory test. None of them felt any stress from the coating when they used it, and the cream was favorably smooth when applied and was also good in touch. They felt the skin was favorably kept moistened by the cream, and the cream did not flow with perspiration, being able to last long.

| | |
|---|---|
| Nanofiber compound solution of Example 4 | 10.0 wt % |
| Cetanol | 5.0 wt % |
| Lanolin | 5.0 wt % |
| Propyl myristate | 10.0 wt % |
| Liquid paraffin | 27.0 wt % |
| Vaseline | 10.0 wt % |
| Lipophilic surfactant | 4.0 wt % |
| Hydrophilic surfactant | 4.0 wt % |
| Paraffin | 1.0 wt % |
| Pure water | 24.0 wt % |
| Total | 100.0 wt % |

Example 16

Nanofiber Compound Pack

The following compounding ingredients were added to the second-step-beaten nanofiber gel prepared in Example 1, and the mixture was mixed at 40° C. by a low speed laboratory stirrer, till it became homogeneous, to prepare a nanofiber compound pack. Ten subjects were asked to use the pack as a sensory test. None of them felt any stress from the coating when they used the pack, and the pack was favorably smooth and was also good in touch. Furthermore, the nanofibers in the pack went also into the wrinkle creases of the skin and allowed the stubborn dirt, fats, etc. in the creases to be removed, giving the feel of refreshing and the effect of lustering the skin. Furthermore, after removal of dirt and fats, the pack could moisturize the skin and supply nutrients to the skin (for example, various nutrients can be added), giving the effects of preventing rough skin and recovering healthy skin. Moreover, the pack had an effect of retaining moisture and water in the entire skin, to keep the skin moist and wet. A small amount of the compound pack was taken on a slide glass, to observe the fine titanium oxide particles with an average diameter of 0.02 μm, and the titanium oxide was found to be finely dispersed without cohering to each other.

| | |
|---|---|
| Nanofiber gel of Example 1 | 20.0 wt % |
| Propylene glycol | 5.0 wt % |
| Glycerol | 5.0 wt % |
| Bentonite | 2.0 wt % |
| Fine titanium oxide particles | 1.0 wt % |
| Pure water | 67.0 wt % |
| Total | 100.0 wt % |

Example 17

Method for Directly Beating Nanofibers in an Emulsion

One point six grams (0.8 g in dry state) of the short nanofiber aggregate with a water content of 100% obtained in Example 1 was taken, and 499.5 g of the commercially available emulsion {The Skin Care Hydrobalancing Softener (trade name) produced by Shiseido Co., Ltd.} used in Example 13 was added to it. The mixture was (1) dispersed at 6000 rpm for 5 minutes by a laboratory blender and (2) filtered by a 50-mesh stainless steel screen, to obtain an emulsion. (3) The nanofibers on the stainless steel screen were returned into the emulsion and the operations of (1) and (2) were further repeated 7 times. As a result, about 0.1 wt % nanofiber emulsion was obtained. Ten grams of the emulsion was placed in a vat, and the water was evaporated in a dryer. The fiber concentration was measured and found to be 0.12 wt %. Furthermore, the commercially available emulsion was added, to prepare 0.10 wt % nanofiber emulsion.

As described for Example 13, ten subjects were asked to use the emulsion as a sensory test. None of them felt any stress from the coating when they used the emulsion, and could have a natural feel for it. Moreover, the sealing capability of nanofibers improved the moist skin feeling after coating. Furthermore, the compounded nanofibers could prevent the emulsion from flowing with perspiration, allowing the emulsion to last longer.

| | |
|---|---|
| Nanofibers (pure) of Example 1 | 0.1 wt % |
| The Skin Care Hydrobalancing Softener | 99.9 wt % |
| Total | 100.0 wt % |

Examples 18 and 19

Compound Solutions with Nanofibers Mixed in an Organic Solvent

The short nanofiber aggregate with a water content of 100% obtained in Example 1 was dried at 50° C. for 12 hours, and 0.8 g of the dried nanofibers were added into 499.5 g of ethanol (solvent of Example 18) or toluene (solvent of Example 19). The nanofibers were (1) directly mixed and dispersed in the solvent at 6000 rpm for 10 minutes by a laboratory blender and (2) filtered by a 50-mesh stainless steel screen, to obtain an organic solvent solution. (3) The nanofibers on the stainless steel screen were returned into the organic solvent and the operations of (1) and (2) were further repeated 7 times. As a result, a compound solution with about 0.1 wt % of nanofibers mixed in the organic solvent could be obtained. Ten grams of the solution was placed in a vat, and the solvent was evaporated in a dryer. The fiber concentration was measured and found to be 0.11 wt % respectively in both Examples 18 and 19. Furthermore, the organic solvent of each example was added to prepare 0.10 wt % nanofiber compound solution. The nanofibers in the solution had been sufficiently dispersed in the organic solvent. The solutions of both the examples obtained as described above showed 61 nm (Example 18) and 62 nm (Example 19) as $\phi$m, 100% (Examples 18 and 19) as Pa and 64% (Example 18) and 63% (Example 19) as Pb. It can be seen that even if nanofibers are beaten in an organic solvent, they can be beaten as they were beaten in water in Example 1.

Meanwhile, the nanofiber-containing ethanol solution (Example 18) can be used for cosmetics and paints, and the nanofiber-containing toluene solution (Example 19) can be used for paints and adhesives.

| | |
|---|---|
| Nanofibers (pure) of Example 1 | 0.1 wt % |
| Ethanol (Example 18) | 99.9 wt % |
| Toluene (Example 19) | 99.9 wt % |
| Total | 100.0 wt % |

Example 20

Substitution with a Solvent in a Nanofiber Compound Solution

The 10 wt % nanofiber gel (water content 9 times=900%) prepared in Example 1 was dehydrated to a gel with a water content of 1 time (100%), and 200 g of it was added into 800 g of ethanol. The mixture was stirred at 6000 rpm for 15 minutes by a laboratory stirrer. The solvent was removed from the mixture to a solvent content of 1 time (100%). The fibers were added again into ethanol, the amount of which was about 8 times the amount of the fibers. The mixture was stirred at 6000 rpm for 15 minutes by a laboratory stirrer. These operations were repeated five times, to achieve a remaining water content of less than 0.1 wt %, for obtaining 1000 g of a compound solution with nanofibers mixed in ethanol (the water remaining rate in ethanol can be controlled by adjusting the frequency of substitution with the solvent suitably for each application). This method allowed the solvent to be changed from water to ethanol. In the case where the nanofibers are likely to cohere with each other depending on the organic solvent used, this method allows the substitution with the solvent while the dispersion or cohesion of nanofibers is confirmed. This method is suitable for homogeneously dispersing the nanofibers low in the affinity with the organic solvent.

Example 21

Nanofiber Compound Paint

Three hundred grams of the nanofiber compound solution with toluene as the solvent obtained in Example 19 and 300 g of a commercially available urethane based paint using toluene as the solvent were stirred at 120 rpm and at 30° C. for 30 minutes by a laboratory kneader, to obtain a nanofiber compound paint. The obtained paint could be smoothly spread during coating by a brush, being able to be easily applied. Furthermore, the paint coating was glossy, and the coating surface was smooth though it contained fibers.

Example 22

Nanofiber Compound Solution Containing a Dispersing Agent (1)

The N6 used in Example 1 and poly-L-lactic acid with a weight average molecular weight of 120,000, a melt viscosity of 30 Pa·s (240° C., shear rate 2432 sec$^{-1}$) and a melting point of 170° C. (optical purity more than 99.5%) were used to obtain polymer alloy chips with an N6 content of 20 wt % by melt-kneading as described for Example 1 at a kneading temperature of 220° C.

The weight average molecular weight of poly-L-lactic acid was obtained as described below. THF (tetrahydrofuran) was mixed with a poly-L-lactic acid chloroform solution, to make a test solution. It was measured at 25° C. using a gel permeation chromatograph (GPC) Waters 2690 produced by Waters, and the weight average molecular weight as polystyrene was obtained. Meanwhile, the melt viscosity of the N6 used in Example 1 at a shear rate of 2432 sec$^{-1}$ was 57 Pa·s. Furthermore, the melt viscosity of the poly-L-lactic acid at 215° C. and at a shear rate of 1216 sec$^{-1}$ was 86 Pa·s. The obtained polymer alloy chips were used to obtain an undrawn yarn by melt spinning as described for Example 1 at a melt temperature of 230° C., a spinning temperature of 230° C. (spinneret face temperature 215° C.) and at a spinning speed of 3200 m/min.

The obtained undrawn yarn was drawn and heat-treated as described for Example 1 at a drawing temperature of 90° C., at a drawing ratio of 1.5 times and at a thermosetting temperature of 130° C., to obtain polymer alloy fibers. The polymer alloy fibers were obtained as 36 filaments of 70 dtex and had a strength of 3.4 cN/dtex, an elongation of 38% and an Uster unevenness of 0.7%. A cross section of the obtained polymer alloy fibers was observed by TEM and found to show an islands-in-sea structure consisting of poly-L-lactic acid as the sea component and N6 as the island component. The island fibers of N6 had a number average diameter of 55 nm, and the polymer alloy fibers had N6 homogeneously dispersed in nanometer size.

Figure 5:
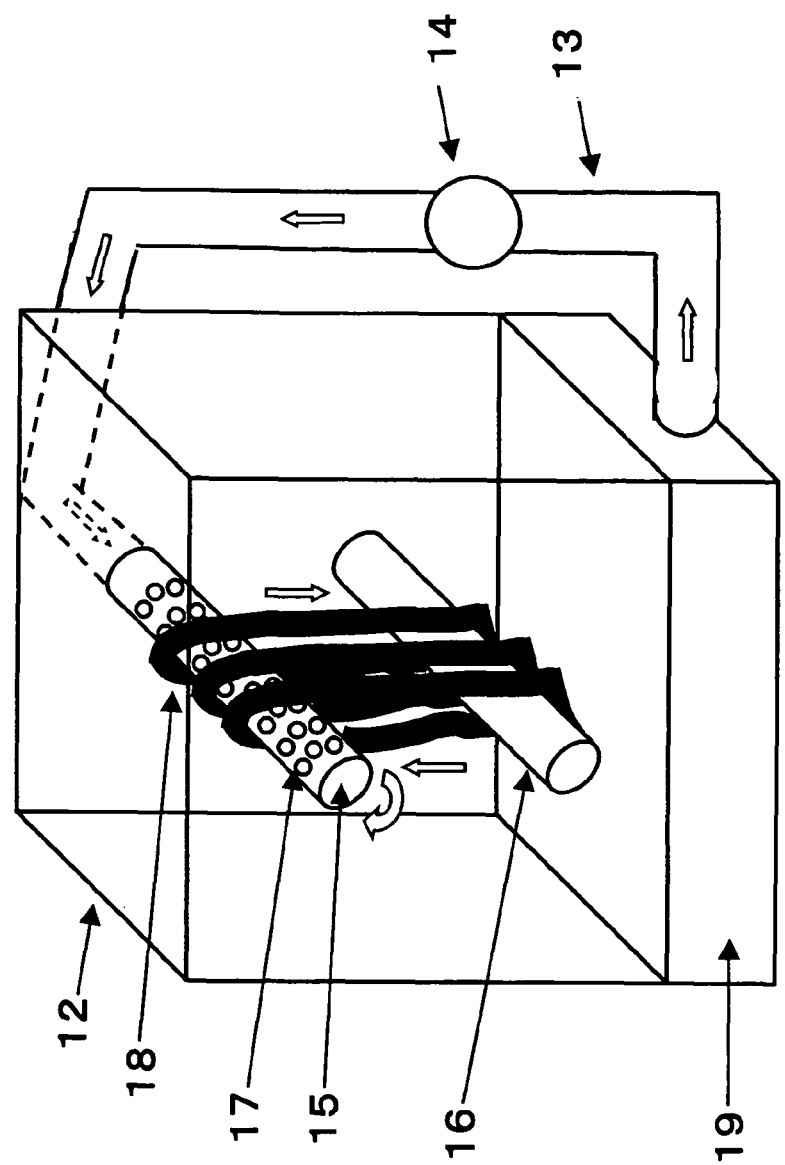
FIG. 5 is a schematic drawing showing a device for removing the sea component from hanks.
Figure 6:
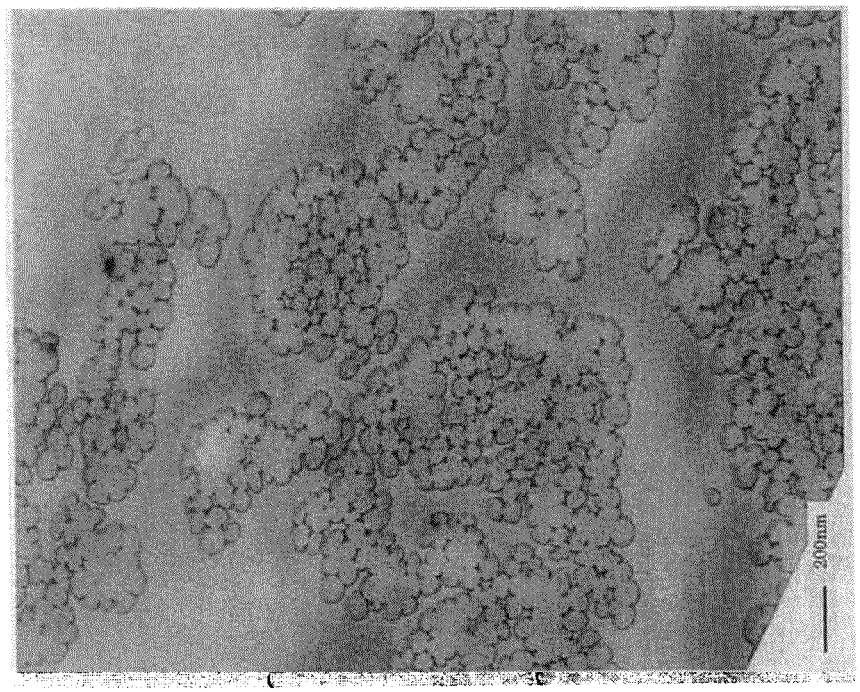
FIG. 6 is a transmission electron microscope (TEM) photograph showing the forms of fibers on a cross section of the PPS nanofibers of Example 42.

The polymer alloy fibers were wound into a hank, to form a tow like a hank of about 130,000 dtex. In this case, a cotton yarn was used to bind the outer circumference of the tow at 30 cm intervals, to prevent that the tow could be scattered during the treatment for removing the sea component. The hank tension was adjusted to keep the fiber density of the tow at 0.04 g/cm$^3$, and the tow was set in the sea component removing device of FIG. 5. The tow was treated with 3% sodium hydroxide of 98° C. for 2 hours, to remove the poly-L-lactic acid as the sea component, for preparing a tow consisting of nanofibers. A cross section of the obtained nanofiber tow was observed by TEM, and it was found that the area ratio of nanofibers in the entire fibers was 100% and that the number average single fiber diameter ɸm was 60 nm, Pa being 100%. The tow was cut to a fiber length of 0.2 mm by a guillotine cutter, to obtain short nanofibers.

About 20 liters of water and 30 g of the short fibers were added into a Niagara beater, and the fibers were beaten in the first step for 10 minutes. The freeness of the first-step-beaten nanofibers was 152. The fibers were dehydrated by a centrifuge, to obtain 250 g of the first-step-beaten fibers with a fiber concentration of 12 wt %. The first-step-beaten fibers were beaten in the second step for 10 minutes by a PFI mill and dehydrated, to obtain 250 g of second-step-beaten fibers with a nanofiber concentration of 10 wt %. The freeness of the second-step-beaten nanofibers was 32. To evaluate the configuration of the second-step-beaten nanofibers, the 10 wt % second-step-beaten nanofibers were diluted with water to prepare 0.01 wt % nanofiber compound solution, and ɸm, Pa and Pb values of the nanofiber compound solution were measured and found to be 58 nm (+m), 100% (Pa) and 67% (Pb).

One gram of the obtained second-step-beaten 10 wt % nanofibers were taken, and 999 g of water was added to them. The mixture was (1) dispersed at 13900 rpm for 5 minutes by a laboratory blender and (2) filtered by a 50-mesh stainless steel screen, to obtain a solution. (3) The nanofibers on the stainless steel screen were returned into water and the operations of (1) and (2) were repeated five times. As a result, about 0.01 wt % nanofiber compound solution was obtained. Ten grams of the solution was placed in a vat, and the water was evaporated in a dryer. The fiber concentration was measured and found to be 0.01 wt %.

An anionic dispersing agent containing sodium polyacrylate as the main ingredient (Shallol AN-103P produced by Dai-ichi Kogyo Seiyaku Co., Ltd.; molecular weight 10000) was added to the nanofiber compound solution, to achieve a concentration of 0.10 wt % based on the weight of the compound solution, and the mixture was stirred by a laboratory blender, to obtain the nanofiber compound solution of Example 22. The dispersion stability of nanofibers in the compound solution was evaluated in reference to the settling time, and the time was found to be 740 minutes. Furthermore, the transparency of the compound solution was 78%.

Examples 23 and 24

Nanofiber Compound Solutions Containing a Dispersing Agent (2)

The tow consisting of nanofibers obtained in Example 22 was cut to a fiber length of 0.5 mm or 1 mm, to obtain short nanofibers. In Example 23, the short nanofibers with a fiber length of 0.5 mm were used, and in Example 24, the short nanofibers with a fiber length of 1 mm were used. In each example, the short nanofibers were beaten according to the same method as that of Example 22, to obtain second-step-beaten fibers. The freeness of the second-step-beaten nanofibers was 43 in Example 23 and 58 in Example 24. In succession, as described for Example 22, the solutions were adjusted in concentration, and the dispersing agent was added, to obtain the nanofiber compound solutions of Examples 23 and 24.

The dispersion stability of the nanofibers in each compound solution was evaluated in reference to the settling time. The settling time in Example 23 was 520 minutes, and that in Example 24, 410 minutes. Furthermore, the transparency of each compound solution was measured. The transparency in Example 23 was 70%, and that in Example 24, 68%.

Examples 25 and 26

Nanofiber Compound Solutions Containing a Dispersing Agent (3)

Nanofiber compound solutions were obtained as described for Example 22, except that the dispersing agent was added to achieve a concentration of 10 wt % in Example 25 and to achieve a concentration of 0.01 wt % in Example 26. The dispersion stability of nanofibers in each compound solution was evaluated in reference to the settling time. The settling time in Example 25 was 452 minutes, and that in Example 26, 627 minutes. Furthermore, the transparency of the compound solution in Example 25 was 65%, and that in Example 26, 83%.

Example 27

Nanofiber Compound Solution Containing a Dispersing Agent (4)

PBT with a melt viscosity of 120 Pas (262° C., 121.6 sec$^1$) and a melting point of 225° C. and polystyrene copolymerized with 22% of 2-ethylhexyl acrylate (co-PS) were melt-kneaded, with the PBT content as 20 wt %, as described for Example 1 at a kneading temperature of 240° C., to obtain polymer alloy chips.

The chips were melt-spun as described for Example 1 at a melting temperature of 260° C., at a spinning temperature of 260° C. (spinneret face temperature 245° C.), at a discharge rate per hole of 1.0 g/min and at a spinning speed of 1200 m/min. The obtained undrawn yarn was drawn and heat-treated as described for Example 1 at a drawing temperature of 100° C., at a drawing ratio of 2.49 times and at a thermosetting temperature of 115° C. The obtained drawn yarn consisted of 36 filaments of 161 dtex and had a strength of 1.4 cN/dtex, an elongation of 33% and an Uster unevenness of 2.0%.

A cross section of the obtained polymer alloy fibers was observed by TEM, and found to show an islands-in-sea structure with co-PS as the sea component and the copolymerized PET as the island component. The number average diameter of copolymerized PET island fibers was 45 nm, and the obtained polymer alloy fibers had copolymerized PET island fibers homogeneously dispersed in nanometer size. The polymer alloy fibers were immersed in trichlene, to dissolve out more than 99% of co-PS as the sea component, and the remaining island fibers were dried and cut by a guillotine cutter to 0.5 mm, for obtaining short PBT nanofibers. From the cut fibers, second-step-beaten fibers were obtained as described for Example 1. The fiber concentration of the second-step-beaten PBT nanofibers was 8 wt % and their freeness was 96. To evaluate the configuration of the second-step-beaten nanofibers, the 10 wt % second-step-beaten fibers were diluted with water, to prepare 0.01 wt % PBT nanofiber compound solution. The φm, Pa and Pb values of the nanofibers were measured and found to be 52 nm (φm), 100% (Pa) and 69% (Pb).

One point three grams of the obtained second-step-beaten fibers were taken, and 998 g of water was added to them. The mixture was (1) dispersed at 13900 rpm for 5 minutes by a laboratory blender and (2) filtered by a 50-mesh stainless steel screen, to obtain a solution. (3) The nanofibers on the stainless steel screen were returned into water and the operations of (1) and (2) were repeated 5 times. As a result, about 0.01 wt % PBT nanofiber compound solution was obtained. Ten grams of the solution was placed in a vat, and the water was evaporated in a dryer. The fiber concentration was measured and found to be 0.01 wt %.

A nonionic dispersing agent (Noigen EA-87 produced by Dai-ichi Kogyo Seiyaku Co., Ltd.; molecular weight 10000) was added to the nanofiber compound solution, to achieve a concentration of 0.10 wt %, and the mixture was stirred by a laboratory blender, to obtain the PBT nanofiber compound solution of Example 27. The dispersion stability of nanofibers in the compound solution was evaluated in reference to the settling time. The time was found to be 669 minutes, and the transparency of the compound solution was 81%.

Example 28

Nanofiber Compound Solution Containing a Dispersing Agent (5)

Twenty weight percent of PP with a melt viscosity of 3.00 Pas (220° C., 121.6 sec$^{-1}$) and a melting point of 162° C. and 80 wt % the poly-L-lactic acid of Example 22 were melt-kneaded as described for Example 1 at a kneading temperature of 220° C., to obtain polymer alloy chips.

The chips were melt-spun as described for Example 1 at a melting temperature of 220° C., at a spinning temperature of 220° C. (spinneret face temperature 205° C.), at a discharge rate per hole of 2.0 g/min and at a spinning speed of 1200 m/min. The obtained undrawn yarn was drawn and heat-treated at a drawing temperature of 90° C., at a drawing ratio of 2.0 times and at a thermosetting temperature of 130° C. The obtained drawn-yarn consisted of 12 filaments of 101 dtex and had a strength of 2.0 cN/dtex and an elongation of 47%.

A cross section of the obtained polymer alloy fibers was observed by TEM and found to show an islands-in-sea structure with poly-L-lactic acid as the sea component and PP as the island component. The number average diameter of PP island fibers was 150 nm, and the obtained polymer alloy fibers had PP island fibers homogeneously dispersed in nanometer size.

The obtained polymer alloy fibers were immersed in 3% sodium hydroxide aqueous solution of 98° C. for 2 hours, to hydrolyze and remove more than 99% of the poly-L-lactic acid in the polymer alloy fibers, and the remaining PP island fibers were neutralized by acetic acid, washed with water, dried and cut to a length of 0.8 mm by a guillotine cutter, to obtain short PP nanofibers.

From the short fibers, as described for Example 1, second-step-beaten fibers were obtained. The fiber concentration of the second-step-beaten PP nanofibers was 6 wt % and their freeness was 104. To evaluate the configuration of the second-step-beaten nanofibers, the 10 wt % second-step-beaten fibers were diluted with water, to obtain 0.01 wt % PP nanofiber compound solution. The +m, Pa and Pb values of the nanofibers were measured and found to be 154 nm (φm), 100% (Pa) and 69% (Pb).

One point seven grams of the obtained second-step-beaten fibers were taken, and 998 g of water was added. The mixture was (1) dispersed at 13900 rpm for 5 minutes by a laboratory blender and (2) filtered by a 50-mesh stainless steel screen. (3) The nanofibers on the stainless steel screen were returned into water and the operations of (1) and (2) were further repeated 5 times. As a result, about 0.01 wt % PP nanofiber compound solution was obtained. Ten grams of the solution was placed in a vat, and the water was evaporated in a dryer. The fiber concentration was measured and found to be 0.01 wt %.

A nonionic dispersing agent (Noigen EA-87 produced by Dai-ichi Kogyo Seiyaku Co., Ltd.; molecular weight 10000) was added to the nanofiber compound solution, to achieve a concentration of 0.10 wt %, and the mixture was stirred to obtain the PP nanofiber compound solution of Example 28. The dispersion stability of nanofibers in the compound solution was evaluated in reference to the settling time. The time was 597 minutes, and the transparency of the compound solution was 72%.

Example 29

Nanofiber Synthetic Paper (1)

Twenty weight percent of N6 with a melt viscosity of 53 Pa·s (262° C., shear rate 121.6 sec$^{-1}$) and a melting point of 220° C., and 80 wt % of a copolymerized PET with a melting point of 225° C. and with a melt viscosity of 310 Pa·s (262° C., shear rate 121.6 sec$^{1}$) obtained by copolymerizing 8 mol % of isophthalic acid and 4 mol % of bisphenol A were kneaded at 260° C. by a twin-screw extrusion kneader, to obtain polymer alloy chips with a b* value of 4. The melt viscosity of the copolymerized PET at 262° C. and 1216 sec$^{-1}$ was 180 Pa·s. The kneading conditions in this case were as follows.

Screw type: Completely intermeshed two screws rotating in the same direction

Screws: Diameter 37 mm, effective length 1670 mm, L/D 45.1; the length of kneading portion was 28% of the effective length of screws; the kneading portion was positioned on the discharge side from ⅓ of the effective length of screws; three back flow portions were provided on the way.

Supply of polymers: N6 and copolymerized PET were separately weighed and separately supplied to the kneader.

Temperature: 260° C.

Vents: Two

The model drawing of the melt spinning apparatus used for melting spinning is shown in FIG. 1. In the drawing, symbol 1 denotes a hopper; 2, a melting portion; 3, a spin block; 4, a spin pack; 5, a spinneret; 6, a chimney; 7, melt-discharged filaments; 8, a filament-collecting finishing guide; 9, a first take-up roller; 10, a second take-up roller; and 11, a wound yarn.

The polymer alloy chips were molten at the melting portion 2 of 275° C. and introduced into the spin block 3 with a spinning temperature of 280° C. The polymer alloy melt was filtered by a nonwoven metallic fabric with a max filtration diameter of 15 µm, and melt-spun from the spinneret 5 with a spinneret face temperature of 262° C. The spinneret used in this case had a metering portion with a diameter of 0.3 mm above the discharge holes and had a discharge hole diameter of 0.7 mm and a discharge hole length of 1.75 mm. The discharge rate per hole in this case was 2.9 g/min. Furthermore, the distance from the bottom face of the spinneret to the cooling start point (the top end of the chimney 6) was 9 cm. The discharged fibers were cooled and solidified for 1 m by cooling air of 20° C., and oiled by the oiling guide 8 installed at 1.8 m below the spinneret 5, and passed around the non-heated first take-up roller 9 and the second take-up roller 10, to be wound at 900 m/min. The spinnability in this case was good, and during continuous spinning for 24 hours, no yarn breaking occurred. The fibers were drawn and heat-treated with the temperature of a first hot roller kept at 98° C. and with the temperature of a second hot roller kept at 130° C. In this case, the drawing ratio between the first hot roller and the second hot roller was set at 3.2 times. The "polymer alloy fibers" obtained as 12 filaments of 120 dtex had excellent properties; a strength of 4.0 cN/dtex, an elongation of 35% and an Uster unevenness of 1.7%. Furthermore, a cross section of the obtained "polymer alloy fibers" was observed by TEM, and found to have an islands-in-sea structure with N6 as the island component (round portions) and with the copolymerized PET as the sea component (the other portion) (see FIG. 2). The diameter of N6 island fibers was 53 nm, and "polymer alloy fibers" with N6 island fibers very finely dispersed could be obtained.

The "polymer alloy fibers" obtained as 12 filaments of 120 dtex were cut by a guillotine cutter to 2 mm. The cut "polymer alloy fibers" were treated by 10% sodium hydroxide of 98° C. for 1 hour, to remove the polyester component as the sea component, and the remaining island fibers were filtered by a filter and dehydrated to a water content of about 100% by a centrifuge, to obtain short fibers. The short fibers were washed with water and dehydrated respectively five times repetitively to remove sodium hydroxide, for obtaining short nanofibers. A cross section of the obtained short N6 nanofibers was observed by TEM, and it was found that the number average single fiber diameter φm was 57 nm and the L/D of the short N6 nanofibers was about 35000.

About 20 liters of water and 30 g of the short nanofibers were added into a Niagara beater, and the fibers were beaten in the first step for 10 minutes. The freeness of the first-step-beaten nanofibers was 362. The fibers were dehydrated by a centrifuge, for obtaining 250 g of first-step-beaten fibers with a fiber concentration of 12 wt %. The first-step-beaten fibers were beaten in the second step for 10 minutes by a PFI mill, and dehydrated to obtain second-step-beaten nanofibers with a fiber concentration of 10 wt %. The freeness of the second-step-beaten nanofibers was 64.

Furthermore, 5.5 g of the second-step-beaten fibers and 0.5 g of an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine) produced by Kumagaya Riki Kogyo Co., Ltd. and water was added to prepare 20 liters of a solution. The prepared solution was poured onto a 25 cm square sheet of filter paper #2 (5 µm) produced by Advantec Co., Ltd placed beforehand on a paper-making wire net, to form a sheet, and the sheet was dehydrated by rollers, dried by a drum dryer, removed from the filter paper, and re-dried, to obtain a synthetic paper composed of nanofibers only.

Figure 4:
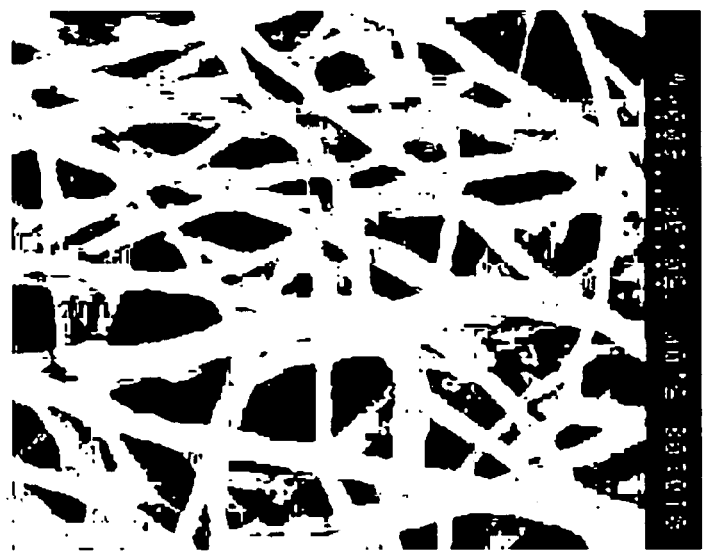
FIG. 4 is a photograph (FIG. 3) showing the surface of the synthetic paper of Example 29, image-processed for pore measurement.
Figure 3:
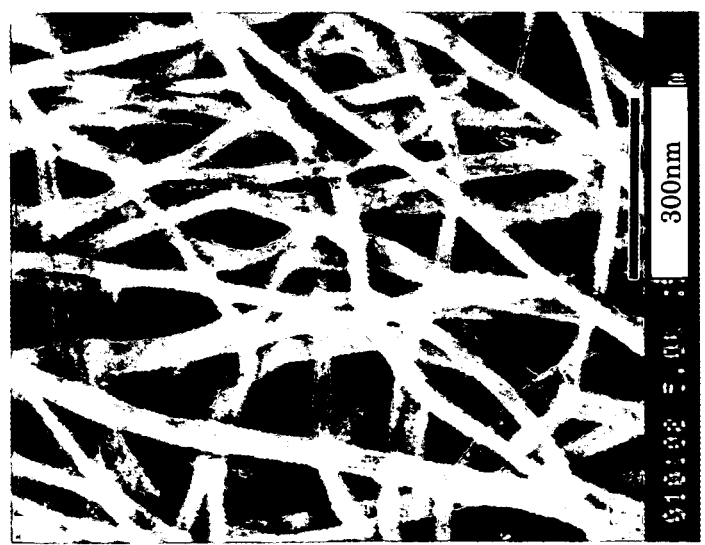
FIG. 3 is an ultrahigh resolution scanning electron microscope (SEM) photograph showing the forms of nylon nanofibers on the surface of the synthetic paper of Example 29.

The surface of the obtained synthetic paper was observed by SEM, and the result is shown in FIG. 3. Unlike the synthetic paper composed of conventional synthetic fibers, the synthetic paper obtained had individual nanofibers dispersed. The obtained synthetic paper was very thin in thickness but was free from pinholes and uniform. The distribution of single fiber diameters of the nanofibers in the synthetic paper is shown in Table 8. The number average single fiber diameter φm of the nanofibers was 57 nm, and the sum Pa of single fiber ratios was 100%, the index Pb of extremal coefficient being 64%. The fiber diameters were very small in irregularity and uniform. The weight per unit area of the obtained synthetic paper was also as very small as 8.4 g/m$^2$, and the thickness was also as small as 30 µm. Furthermore, though the synthetic paper was composed of 100% nanofibers, good paper could be produced even without a binder owing to the cohesive force and intensive entanglement between nanofibers. The obtained nanofiber synthetic paper was very thin in thickness, but had a strength of 2.2 N/cm and an elongation of 12%, showing no problem in view of practical use. Moreover, since the obtained synthetic paper had nanofibers with a small average single fiber diameter homogeneously dispersed, the average pore area was as small as 0.0033 µm and the pore areas were uniform. The average pore area was measured according to the measuring method described at item S. The image processing conditions for deleting the extra fibers unnecessary for measurement of pore area were 91.6 as the highest average luminance Lh and 45.8% as the deletion luminance level corresponding to 50% of it. The measurement image in this case is shown in FIG. 4. The synthetic paper of this example had such fine pore areas, and was further good in the dispersibility and uniformity of nanofibers. So, it was free from large pinholes, and the number of pinholes of 50 μm or more was 0. Furthermore, the air permeability was also as small as 0.35 cc/cm$^2$/sec. So, it can be seen that the obtained synthetic paper had high gas impermeability. Moreover, the synthetic paper was highly smooth on the surface, having a surface smoothness of 1660 seconds.

Furthermore, the density of commercially available paper produced by using an ordinary pulp is about 0.5 g/cm$^3$, but the density of the nanofiber synthetic paper of this example was 0.28 g/cm$^3$. Even though the nanofibers were highly cohesive and difficult to disperse, the obtained synthetic paper had a relatively low density. The reason is considered to be that the nanofibers could be well dispersed by the method for producing a nanofiber synthetic paper of this invention. For the nanofiber synthetic paper obtained in this example, pressurization and drying treatment were performed for removing water after completion of papermaking, but such operations as simple pressurization and hot pressing generally employed in the synthetic paper field for improving the density and strength were not performed. So, if such operations are employed, properties may be able to be adjusted suitably for each purpose and application. Furthermore, the moisture absorption coefficient (AMR) of the nanofiber synthetic paper of this example was measured and found to be 6.4%. This moisture absorption capability is excellent compared with 2.8% of the synthetic paper composed of conventional ultrafine fibers obtained in Comparative Example 18.

Example 30

Nanofiber Synthetic Paper (2)

A nanofiber synthetic paper obtained by using a screen woven fabric as the base material is described below.

Five point five grams of the second-step-beaten fibers obtained in Example 29 and 0.5 g of an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine, and water was added to prepare 20 liters of a solution. The prepared solution was poured onto a 25 cm square "screen woven fabric (made of PET, fiber diameter 70 μm, pore size 80 μm square)" placed beforehand on a papermaking wire net, to form a paper sheet, and it was dehydrated using rollers and dried by a drum dryer. It was attempted to remove the nanofibers from the screen woven fabric, but they could not be removed. Thus, a nanofiber synthetic paper with a screen woven fabric as the base material was obtained.

The surface of the obtained synthetic paper was observed by SEM, and as a result, it was found that individual nanofibers were dispersed at the portions corresponding to the meshes of the lattice of the screen woven fabric, as in Example 29. However, it was observed that the nanofibers were firmly entangled with the monofilaments forming the lattice of the screen woven fabric, at the portions near such monofilaments. The nanofibers in the synthetic paper had a number average single fiber diameter φm of 58 nm, and the sum Pa of single fiber ratios was 100%, while the index Pb of extremal coefficient of single fiber diameters was 66%. The nanofibers were entangled with the monofilaments of the screen woven fabric and were bound to each other due to the cohesive force and powerful entangling action between them. So, even though no binder was used, the nanofibers did not come off from the screen woven fabric, and a good synthetic paper could be produced. In the nanofiber synthetic paper of this example, the nanofibers existing at the portions corresponding to the meshes of the lattice of the screen woven fabric were also homogeneously dispersed, and without any large pinholes or breaking at the portions, the synthetic paper had sufficient strength. In the obtained synthetic paper, the screen woven fabric as the base material was integrated with nanofibers. The synthetic paper had a total weight per unit area of 45.6 g/m$^2$, a thickness of 102 μm and a density of 0.45 g/cm$^3$. If it is assumed to remove the screen woven fabric portion (weight per unit area 37.4 g/m$^2$, a thickness 70 μm, density 0.53 g/cm$^3$) from the synthetic paper, the nanofibers alone had a weight per unit area of 8.2 g/m$^2$, a thickness of 32 μm and a density of 0.26 g/cm$^3$. The values of the nanofiber portion only of this example were about the same as those of the synthetic paper composed of 100% nanofibers of Example 29. That is, a nanofiber synthetic paper was formed on a screen woven fabric, to form a compound synthetic paper. Though a screen woven fabric was used as the base material, a nanofiber compound synthetic paper could be obtained without using a binder. The obtained compound synthetic paper has the screen woven fabric integrated, the density of the nanofibers existing in the portion corresponding to the lattice of the screen woven fabric is considered to be about the same as that of the nanofiber synthetic paper of Example 29. Furthermore, the compound synthetic paper had a strength of about 91.2 N/cm and an elongation of 34% owing to the reinforcing effect of the screen woven fabric. However, actually, the nanofibers existing at the portion corresponding to the lattice of the screen woven fabric could be broken if they were pulled with a strong force, since they had an elongation of about ten and odd percent as in Example 29. However, in view of handling, the synthetic paper of this example is easier to handle than the synthetic paper of Example 29. Furthermore, since the compound synthetic paper was uniform in the single fiber diameters of nanofibers, it was also uniform in pore areas, and the average pore area was as small as 0.0045 μm$^2$. Moreover, it was very thin in thickness and free from large pores and pinholes, and the number of pinholes of 50 μm or more was 0. Since the synthetic paper had been uniformly processed, the air permeability was as very small as 0.27 (cc/cm$^2$/sec). It was also highly smooth on the surface, having a surface smoothness of 830 seconds. For the nanofiber synthetic paper obtained in this example, pressurization and drying treatment were performed for removing water after completion of papermaking, but such operations as simple pressurization and hot pressing for improving the density and strength were not performed. So, if such operations are employed, properties may be able to be adjusted suitably for each purpose and application. Furthermore, the moisture absorption coefficient (AMR) of the nanofiber compound synthetic paper of this example was measured and found to be 5.7%. This moisture absorption capability is excellent compared with 2.8% of the synthetic paper composed of conventional ultrafine fibers obtained in Comparative Example 18.

Example 31

Nanofiber Synthetic Paper (3)

This example describes a synthetic paper consisting of nanofibers and N6 ultrafine fibers with a diameter of 2 μm mixed together.

Sixteen point six grams of the second-step-beaten fibers obtained in Example 29, 0.42 g of N6 ultrafine fibers cut to 2 mm and having a number average single fiber diameter of 2 μm and 0.5 g of an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. The prepared solution was directly poured onto a papermaking wire net, to form a sheet, and the sheet was dehydrated by rollers and dried by a drum dryer, to obtain a mixed fiber synthetic paper composed of 80% of nanofibers with a weight per unit area of 32.3 g/m² and 20% of N6 ultrafine fibers mixed together.

The surface of the obtained synthetic paper was observed by SEM. As a result, the nanofibers were found to be 59 nm in the number average single fiber diameter φm, 100% in the sum Pa of single fiber ratios and 65% in the index Pb of extremal coefficient of single fiber diameters. The obtained nanofiber synthetic paper contained only 80% of nanofibers, but papermaking properties were good. Furthermore, though the synthetic paper contained ultrafine fibers, it had a weight per unit area of 32.3 g/m², having a small thickness and also had a strength of 1.5 N/cm and an elongation of 7.3%, assuring no problem in view of practical use. When the surface of the synthetic paper was observed by SEM, most of the nanofibers were individually scattered though some nanofibers were entangled with each other among the ultrafine fibers. The nanofibers were homogeneously dispersed in the obtained mixed-fiber synthetic paper. Moreover, the nanofibers spread like a spider's web to secure a space in which the ultrafine fibers larger in diameter than the nanofibers worked as aggregate. Compared with the synthetic paper of Example 30, the synthetic paper of this example had a thickness of 154 μm, being bulkier, and had a rather smaller density of 0.21 g/cm³. So, it could have an air permeability of 11 cc/cm²/sec, which was very larger than that of Example 30. So, it can be considered that the mixed-fiber synthetic paper of this example can be used in fields where air permeability is required. Furthermore, the average pore area was also as large as 0.0113 μm², but the synthetic paper was free from coarse holes and pinholes. The number of pinholes of 50 μm or more was 0. The synthetic paper was also highly smooth on the surface, having a surface smoothness of 320 seconds.

For the nanofiber synthetic paper composed of mixed fibers obtained in this example, pressurization and drying treatment were performed for removing water after completion of papermaking, but such operations as simple pressurization and hot pressing for improving the density and strength were not performed. So, if such operations are employed, properties may be able to be adjusted suitably for each purpose and application. Furthermore, the moisture absorption coefficient (AMR) of the nanofiber synthetic paper composed of mixed fibers obtained in this example was measured and found to be 5.1%. This moisture absorption capability is excellent compared with 2.8% of the synthetic paper composed of conventional ultrafine fibers obtained in Comparative Example 18.

Example 32

Nanofiber Synthetic Paper (4)

This example describes a case where 5 wt % or less of nanofibers were mixed.

A nanofiber synthetic paper was prepared by mixing a small amount of nanofibers with a synthetic paper mainly composed of N6 ultrafine fibers with a number average single fiber diameter of 2 μm and a pulp binder. Zero point five zero grams of second-step-beaten fibers obtained as described for Example 29, 0.22 g of wood pulp with a freeness of 450, 1.80 g of N6 ultrafine fibers with a number average single fiber diameter of 2 μm, an anionic dispersing agent (Shallol AN-103P produced by Dai-ichi Kogyo Seiyaku Co., Ltd.; molecular weight 10000), and 1 liter of water were added into a disintegrator, and dispersed for 5 minutes. The dispersion in the disintegrator was transfused into the vessel of an experimental paper machine (square sheet machine), and water was added to prepare 20 liters of a solution. The prepared solution was directly poured onto a papermaking wire net, to form a sheet, and the sheet was dehydrated by rollers and dried by a drum dryer, to obtain a mixed-fiber synthetic paper consisting of 2.4% of nanofibers, 87% of ultrafine fibers and 10.6% of wood pulp.

The surface of the obtained synthetic paper was observed by SEM, and as a result, it was found that the nanofibers in the synthetic paper were 59 nm in the number average single fiber diameter, 100% in the sum Pa of single fiber ratios and 63% in the index Pb of extremal coefficient of single fiber diameters. Since wood pulp existed as a binder, the paper could be favorably produced though the amount of nanofibers was small, and a mixed-fiber synthetic paper with a weight per unit area of 31.6 g/m², a thickness of 243 μm, a strength of 3.1 N/cm and an elongation of 15% could be obtained. For the mixed-fiber synthetic paper obtained in this example, since it was intended to disperse the nanofibers widely in the space within the ultrafine fibers, the pressurization for removing water after completion of papermaking was reduced, being followed by drying. According to the observation of the surface by SEM, since the rate of nanofibers in the mixed-fiber synthetic paper of this example was small, the entanglement among the fibers was less than in Example 31. The fibers were individually scattered, and the nanofibers were homogeneously dispersed in the mixed-fiber synthetic paper. Furthermore, since the amount of nanofibers was very small compared with that of Example 31, the density was also as small as 0.13 g/cm³, and the average pore area was also as large as 0.0470 μm². The synthetic paper was free from large pores and pinholes, and the number of pinholes of 50 μm or more was 0. Moreover, the surface smoothness was 220 seconds.

Since the mixed-fiber synthetic paper is small in the resistance against the permeation of a fluid such as gas or liquid, it is useful as a base material for separating or adsorbing a useful component in such a fluid and also for removing fine particles or a foreign matter. The mixed-fiber synthetic paper of this example had an air permeability of 34 cc/cm²/sec, which was very large compared with that of Example 31. Since the synthetic N6 nanofiber paper has a high air permeability, it is suitable for an air filter. Moreover, the surface of the N6 nanofiber synthetic paper contains numerous pores of nanometer level, the synthetic paper is considered to be small also in the resistance against the permeation of liquid. So, it can be suitably used as a liquid filter or a separator for secondary battery or capacitor, as it is.

Example 33

Nanofiber Synthetic Paper (5)

This example describes a nanofiber synthetic paper with a low weight per unit area.

One point five grams of second-step-beaten fibers obtained as described for Example 29 and 0.5 g of an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. The prepared solution was poured onto a 25 cm square screen woven fabric (made of PET, fiber diameter 70 μm, pore size 80 μm square) placed beforehand on a papermaking wire net, to form a sheet, and the sheet was dehydrated by rollers and dried by a drum dryer. It was attempted to remove the nanofibers from the screen woven fabric, but they could not be removed. Thus, a nanofiber synthetic paper with a screen woven fabric as the base material was obtained.

The surface of the obtained synthetic paper was observed by SEM, and as a result, it was found that the nanofibers of the synthetic paper were 57 nm in the number average single fiber diameter φm, 100% in the sum Pa of single fiber ratios and 73% in the index Pb of extremal coefficient of single fiber diameters. Since the compound synthetic paper as a whole was based on a screen woven fabric, it had a weight per unit area of 39.5 g/m$^2$, a thickness of 78 μm, a density of 0.51 g/cm$^3$, a strength of 91.2 N/cm and an elongation of 34%. The nanofibers only obtained by removing the screen woven fabric (weight per unit area 37.4 g/m$^2$, thickness 70 μm, density 0.53 g/cm$^3$) from the synthetic paper had a weight per unit area of 2.1 g/m$^2$, a thickness of 8.0 μm and a density of 0.26 g/cm$^3$. Since the weight per unit area of the nanofibers only was 2.1 g/m$^2$, the thickness could be made very thin. It is very difficult to make a sheet of 10 g/m$^2$ or less from an ordinary dry nonwoven fabric, but in the case of nanofibers, since the number of fibers was large to assure a high cover rate, an unprecedentedly thin synthetic paper could also be made. Furthermore, the nanofibers were very thinly entangled with the lattice portion (fiber diameter 70 μm, pore size 80 μm square) as a whole of the screen woven fabric uniformly like a spider's web, but some pinholes were observed. The number of pinholes of 50 μm or more was 2 holes/cm$^2$. A portion free from pinholes and with good evenness was sampled, and the air permeability was measured and found to be 0.66 cc/cm$^2$/sec. It was rather larger than that of Example 30, probably because of the influence of some pinholes existing. The average pore area was 0.0042 μm$^2$, being larger than that of Example 30. Furthermore, the synthetic paper was highly smooth on the surface, having a surface smoothness of 430 seconds. The synthetic paper did not have a problem of strength, since the synthetic paper as a whole was reinforced by the screen woven fabric, and could be handled easily. Moreover, when no large force acted on the nanofibers existing at the portion corresponding to the meshes of the lattice, such a problem that the nanofibers were broken did not arise at all.

Example 34

Nanofiber Synthetic Paper (6)

A nanofiber synthetic paper with a number average single fiber diameter of 114 μm will be described below.

Melt spinning was performed as described for Example 29, except that N6 (mixing rate 50 wt %) with a melt viscosity of 500 Pa·s (262° C., shear rate 121.6 sec$^{-1}$) and a melting point of 220° C. was used as N6. The spinnability in this case was good, and yarn breaking occurred once during continuous spinning for 24 hours. The fibers were drawn and heat-treated as described for Example 29, to obtain polymer alloy fibers as 36 filaments of 128 dtex having excellent properties such as a strength of 4.3 cN/dtex, an elongation of 37% and an Uster unevenness of 2.5%. A cross section of the obtained polymer alloy fibers was observed by TEM and found to show an islands-in-sea structure with the copolymerized PET as the sea component and the N6 as the island component, with a number average N6 island fiber diameter of 110 nm, having the N6 very finely dispersed, as in Example 29.

The "polymer alloy fibers" obtained as 36 filaments of 128 dtex were cut to 2 mm by a guillotine cutter. The cut "polymer alloy fibers" were treated with 10% sodium hydroxide of 98° C. for 1 hour, to remove the polyester component as the sea component, and the remaining island fibers were filtered by a filter and dehydrated by a centrifuge to a water content of about 100%, to obtain short fibers.

The obtained short fibers were washed with water and dehydrated respectively 5 times repetitively, to remove sodium hydroxide for obtaining the short nanofibers. A cross section of the obtained short N6 nanofibers was observed by TEM, and it was found that the number average single fiber diameter φm was 114 nm, and that the L/D of the short N6 nanofibers in this case was about 17500.

About 20 liters of water and 30 g of the short fibers were added into the vessel of a Niagara beater, and the fibers were beaten in the first step for 10 minutes. The obtained fibers were dehydrated by a centrifuge, for obtaining first-step-beaten fibers with a fiber concentration of 10 wt %. The first-step-beaten fibers were beaten in the second step for 10 minutes by a PFI mill, and dehydrated, to obtain second-step-beaten nanofibers with a fiber concentration of 10 wt %. Furthermore, 5.5 g of the second-step-beaten fibers and 0.5 g of an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. The prepared solution was poured onto a 25 cm square screen woven fabric (fiber diameter 70 μm, pore size 80 μm square) placed beforehand on a papermaking wire net, to form a sheet, and the sheet was dehydrated by rollers and dried by a drum dryer. It was attempted to remove the nanofibers from the screen woven fabric, but they could not be removed. Thus, a nanofiber synthetic paper having a screen woven fabric as the base material was obtained.

The surface of the obtained synthetic paper was observed by SEM, and as a result, it was found that the number average single fiber diameter φ was 114 nm, that the sum Pa of single fiber ratios was 98%, and that the index Pb of extremal coefficient of single fiber diameters was 58%. The obtained nanofiber synthetic paper could have paper formed on the screen woven fabric without any problem. Furthermore, the surface was observed by SEM, and as a result, it was found that the nanofibers were individually scattered as in Example 29, and the synthetic paper obtained had nanofibers homogeneously dispersed. The obtained synthetic paper as a whole had a weight per unit area of 46.9 g/m$^2$, a thickness of 111 μm, a density of 0.42 g/cm$^3$, a strength of 91.2 N/cm and an elongation of 34%, since it was based on the screen woven fabric. The nanofibers only obtained by removing the screen woven fabric (weight per unit area 37.4 g/m$^2$, thickness 70 μm, density 0.53 g/cm$^3$) from the synthetic paper had a weight per unit area of 8.7 g/m$^2$, a thickness of 41 μm and a density of 0.21 g/cm$^3$, and they formed a nanofiber synthetic paper with good evenness. Moreover, since the nanofibers were homogeneously dispersed, the synthetic paper did not have large pores or pinholes, and the number of pinholes of 50 μm or more was 0. The synthetic paper was also highly smooth on the surface, having a surface smoothness of 1180 seconds.

The air permeability was as small as 0.63 cc/cm$^2$/sec as in Example 29, and a synthetic paper with a high gas impermeability could be obtained. However, the air permeability was somewhat larger than that of Example 30. The reason is that the synthetic paper obtained in this example had a larger average pore area of 0.0084 μm$^2$ and a lower density of 0.21 g/cm$^3$ compared with the synthetic paper of Example 29. Another reason is considered to be that since the number average single fiber diameter of nanofibers was larger than that of Example 29, the dispersibility of nanofibers improved, causing a smaller number of fibers to adhere to each other compared with the fibers of Example 29.

Example 35

Nanofiber Synthetic Paper (7)

A compound synthetic paper consisting of a synthetic paper composed of N6 ultrafine fibers with a number average single fiber diameter of 2 μm and a synthetic paper composed of nanofibers will be described below.

At first, a synthetic paper composed of ultrafine fibers was made from N6 ultrafine fibers with a single fiber diameter of 2 μm and a pulp binder was produced. N6 ultrafine fibers were cut to 2 mm and beaten to achieve a freeness of 350. One point eight five grams of the N6 ultrafine fibers, 0.22 g of wood pulp with a freeness of 450 and an anionic dispersing agent (Shallol AN-103P produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. The prepared solution was directly poured onto a papermaking wire net, to form a sheet, and the sheet was dehydrated by rollers and dried by a drum dryer, to obtain a synthetic paper consisting of N6 ultrafine fibers and a binder of wood pulp. The synthetic paper composed of ultrafine fibers had a weight per unit area of 33.4 g/m$^2$, a thickness of 242 μm and a density of 0.14 g/cm$^3$. The obtained synthetic paper composed of ultrafine fibers was used as a filter instead of the screen woven fabric placed on the wire net of the experimental paper machine of Example 29. The disarranged nanofibers dispersed in the disintegrator of Example 29 were transfused into the vessel of an experimental paper machine (square sheet machine), and water was added to prepare 20 liters of a solution. The prepared solution was poured onto a 25 cm square N6 ultrafine fiber synthetic paper placed beforehand on a papermaking wire net, to form a sheet, and the sheet was dehydrated by rollers and dried by a drum dryer, to obtain a compound synthetic paper having the nanofibers laminated on the ultrafine fibers. Since a synthetic N6 ultrafine fiber paper produced beforehand was used as the base material, it was only required to form a sheet of nanofibers dispersed on the surface of and inside the base material, and the intended paper could be produced well.

The surface of the obtained synthetic paper was observed by SEM, and as a result, it was found that the nanofibers in the synthetic paper were 57 nm in the number average single fiber diameter φm, 99% in the sum Pa of single fiber ratios and 72% in the index Pb of extremal coefficient of single fiber diameters. The obtained compound synthetic paper had a total weight per unit area of 42.2 g/m$^2$, a thickness of 285 μm, a strength of 3.2 N/cm and an elongation of 16%. If it is assumed that the nanofibers are merely laminated on the ultrafine fiber synthetic paper, the difference between the compound synthetic paper and the N6 ultrafine fiber synthetic paper portion only corresponds to the portion of nanofibers only. So, the nanofibers only in the compound synthetic paper had a weight per unit area of 8.8 g/m$^2$, a thickness of 43 μm and a density of 0.20 g/cm$^3$. Actually in the compound synthetic paper obtained in this example, the nanofibers were spread in the space within the N6 ultrafine fibers. To obtain a compound synthetic paper with this constitution, if the density of the N6 ultrafine fiber synthetic paper is set at a small value, the nanofibers can be dispersed better among the ultrafine fibers. Furthermore, in the compound synthetic paper of this example, the number of pinholes of 50 μm or more was 0, and the synthetic paper was highly smooth on the surface, having a surface smoothness of 560 seconds.

The compound synthetic paper of this example had a low density of 0.15 g/cm$^3$ and a large average pore area of 0.0174 μm$^2$. So, it had an air permeability of 23 cc/cm$^2$/sec, which was very larger than that of Example 31. The compound synthetic paper is low in the resistance against the permeation of a fluid such as gas or liquid, and can be useful as a base material for separating or adsorbing a useful ingredient from such a fluid or the like and also for removing fine particles or a foreign matter. If the compound synthetic paper is, for example, pleated or corrugated, a molded synthetic paper can be obtained, and it can be used as a filter medium of various filters.

Example 36

Nanofiber Synthetic Paper (8)

A compound synthetic paper consisting of a melt-blown nonwoven fabric and a nanofiber synthetic paper will be described below.

A melt-blown PP nonwoven fabric with a number average single fiber diameter of 3 μm produced by the melt blow method (weight per unit area 30 g/m$^2$, thickness 130 μm, density 0.231 g/cm$^3$) was used as a filter for papermaking, and a nanofiber solution was poured onto the nonwoven fabric as described for Example 33, to obtain a compound synthetic paper consisting of the melt-blown PP nonwoven fabric and nanofibers.

The surface of the obtained compound synthetic paper was observed by SEM, and as a result, it was found that the nanofibers were 57 nm in the number average single fiber diameter φm, 99% in the sum Pa of single fiber ratios and 63% in the index Pb of extremal coefficient of single fiber diameters. Furthermore, the obtained compound synthetic paper had a total weight per area of 35.6 g/m$^2$, a thickness of 160 μm, a strength of 3.5 N/cm and an elongation of 43%. If it is assumed that the nanofibers were merely laminated on the melt-blown PP nonwoven fabric, the difference between the compound synthetic paper as a whole and the portion of melt blown nonwoven fabric only corresponds to the portion of nanofibers. So, the nanofibers only had a weight per unit area of 5.6 g/m$^2$, a thickness of 30 μm and a density of 0.19 g/cm$^3$. As described here, a melt-blown PP nonwoven fabric could be used to uniformly disperse nanofibers into the space of ultrafine fibers as in Example 35. So, since the compound synthetic paper had a low density of 0.23 g/cm$^3$ and a large average pore area of 0.0153 μm$^2$, it could have an air permeability of 15 cc/cm$^2$/sec, which was larger than that of Example 31. In the compound synthetic paper of this example, the number of pinholes of 50 µm or more was 1 hole/cm², and the synthetic paper was highly smooth on the surface, having a surface smoothness of 380 seconds.

Compared with Example 35, the melt-blown PP nonwoven fabric had a larger fiber diameter and an apparently higher density, but since the number of ultrafine fibers in the melt-blown PP nonwoven fabric was smaller, the pores were not so different from those of Example 35. The synthetic paper of this example is small in the resistance against the permeation of a fluid such as gas or liquid, and can be useful as a base material for separating or adsorbing a useful component from such a fluid, etc. or for removing fine particles or a foreign matter. If this compound synthetic paper is pleated or corrugated to make a molded synthetic paper, it can be used as a filter medium of various filters.

Example 37

Nanofiber Synthetic Paper (9)

A nanofiber synthetic paper obtained by pre-removing the sea component from polymer alloy fibers and subsequently cutting will be described below.

Polymer alloy fibers were obtained according to the same method as that of Example 29. The polymer alloy fibers obtained as 12 filaments of 120 dtex were wound into a hank of about 130,000 dtex. It was treated by 10% sodium hydroxide of 98° C. for 1 hour, to remove the polyester component as the sea component, and the remaining island fibers were washed with water and dried. The obtained hank of nanofibers was cut to 2 mm by a guillotine cutter, to obtain short nanofibers. Furthermore, the obtained short fibers were used to prepare a solution as described for Example 30, and from the solution, a nanofiber synthetic paper having nanofibers and a screen woven fabric integrated was obtained.

The surface of the obtained synthetic paper was observed by SEM, and as a result, it was found that the number average single fiber diameter $\phi$m was 59 nm, that the sum Pa of single fiber ratios was 98%, and that the index Pb of extremal coefficient of single fiber diameters was 71%. Since the synthetic paper was based on a screen woven fabric, it had a total weight per unit area of 46.5 g/m², a thickness of 108 µm, a density of 0.44 g/cm³, a strength of 91.2 N/cm and an elongation of 34%. When the screen woven fabric (weight per unit area 37.4 g/m², thickness 70 µm, density 0.53 g/cm³) was removed from the synthetic paper, the nanofibers only had a weight per unit area of 9.1 g/m² and a thickness of 38 µm. The nanofiber synthetic paper was of the same level as that of Example 30. The synthetic paper had a small pore area of 0.0051 µm and a density of 0.24 g/cm³, and the air permeability was measured and found to be as small as 0.33 cc/cm²/sec. As in Example 30, the nanofiber synthetic paper obtained had a high air impermeability. In the synthetic paper of this example, the number of pinholes of 50 µm or more was 0, and the synthetic paper was highly smooth on the surface, having a surface smoothness of 900 seconds.

Example 38

Nanofiber Synthetic Paper (10)

A case where a nanofiber synthetic paper is obtained from polymer alloy fibers with PLA as the sea component will be described below.

The N6 used in Example 29 and poly-L-lactic acid with a weight average molecular weight of 120,000, a melt viscosity of 30 Pa·s (240° C., 2432 sec⁻¹) and a melting point of 170° C. (optical purity more than 99.5%) were melt-kneaded with N6 content as 20 wt % as described for Example 29 at a kneading temperature of 220° C., to obtain polymer alloy chips with a b* value of 3. Meanwhile, the weight average molecular weight of poly-L-lactic acid was obtained as described below. THF (tetrahydrofuran) was mixed with a poly-L-lactic acid chloroform solution, to make a test solution. It was measured at 25° C. using a gel permeation chromatograph (GPC) Waters 2690 produced by Waters, and the weight average molecular weight as polystyrene was obtained. Meanwhile, the melt viscosity of the N6 used in Example 30 at 240° C. and a shear rate of 2432 sec⁻¹ was 57 Pa·s. Furthermore, the melt viscosity of the poly-L-lactic acid at 215° C. and at 1216 sec⁻¹ was 86 Pa·s.

The polymer alloy chips were melt-spun as described for Example 29 at a melting temperature of 230° C., at a spinning temperature of 230° C. (spinneret face temperature 215° C.) and at a spinning speed of 3500 µm/min. In this case, an ordinary spinneret with a hole diameter of 0.3 mm and a hole length of 0.55 mm was used, but Barus effect was little observed, while spinnability improved remarkably compared with Example 29. During continuous spinning for 120 hours, no yarn breaking occurred. The discharge rate per hole was set at 0.94 g/min. As a result, a highly oriented undrawn yarn consisting of 36 filaments of 92 dtex was obtained, and having a strength of 2.4 cN/dtex, an elongation of 90%, a shrinkage percentage in boiled water of 43% and an Uster unevenness of 0.7%, it was very excellent as a highly oriented undrawn yarn. Especially compared with Example 29, Barus decreased greatly, and as a result, the yarn unevenness was greatly improved.

The highly oriented undrawn yarn was drawn and heat-treated as described for Example 29 at a drawing temperature of 90° C., at a drawing ratio of 1.39 times and at a thermosetting temperature of 130° C. The obtained drawn yarn consisted of 36 filaments of 67 dtex and had excellent properties, i.e., a strength of 3.6 cN/dtex, an elongation of 40%, a shrinkage percentage in boiled water of 9% and an Uster unevenness of 0.7%. A cross section of the obtained polymer alloy fibers was observed by TEM, and as a result, it showed an islands-in-sea structure with poly-L-lactic acid as the sea component (light portion) and N6 as the island component (dark portions). The number average diameter of N6 island fibers was 55 nm, and N6 island fibers were homogeneously dispersed in nanometer size in the obtained polymer alloy fibers.

The "polymer alloy fibers" obtained as 36 filaments of 67 dtex were bundled to 2220 dtex, and cut to 2 mm by a guillotine cutter. The cut "polymer alloy fibers" were treated by 1% sodium hydroxide of 98° C. for 1 hour, to remove the polyester component as the sea component, and the remaining island fibers were filtered by a filter, and dehydrated by a centrifuge to a water content of about 100%, to obtain short fibers. Since the sea component was changed from the copolymerized PET of Example 29 to the PLA of this example, the concentration of sodium hydroxide could be remarkably lowered from 10% to 1%. Then, as described for Example 29, beating and papermaking were carried out, to obtain a synthetic paper composed of 100% nanofibers. The surface of the obtained synthetic paper was observed by SEM, and as a result, it was found that a synthetic paper having nanofibers uniform in diameter individually dispersed was obtained as described for Example 29. Furthermore, the nanofibers were 56 nm in the number average single fiber diameter $\phi$m, 100% in the sum Pa of single fiber ratios and 62% in the index Pb of extremal coefficient of single fiber diameters. Thus a synthetic paper with a very small weight per unit area of 8.4 g/m² and a small thickness of 34 µm could be obtained. Furthermore, as in Example 29, the paper could be favorably produced even without a binder. Though the obtained nanofiber synthetic paper had a weight per unit area of 8.4 g/m², being very small in thickness, it had a strength of 2.0 N/cm and an elongation of 13% without any problem in view of practical use. Moreover, since nanofibers with uniform single fiber diameters were homogeneously dispersed in the synthetic paper, the average pore area was also as small as 0.0037 µm². The pore area was measured according to the measuring method specified for the examples, and the image processing conditions for deleting the extra fibers unnecessary for pore area measurement were 88.4 as the highest average luminance Lh and 44.2% as the deletion luminance level corresponding to 50% of it. Furthermore, the obtained nanofiber synthetic paper had a small air permeability of 0.37 cc/cm²/sec and a density of 0.26 g/cm³, having high gas impermeability. In the compound synthetic paper of this invention, the number of pinholes of 50 µm or more was 0, and the synthetic paper was highly smooth on the surface, having a surface smoothness of 1680 seconds.

The moisture absorption coefficient (AMR) of the obtained nanofiber synthetic paper was measured and found to be 6.1%, showing excellent moisture absorbability compared with 2.8% of the synthetic paper composed of conventional ultrafine fibers of Comparative Example 18.

Comparative Examples 9, 10 and 11

PET with a melt viscosity of 180 Pa·s (290° C., shear rate 121.6 sec$^{-1}$) and a melting point of 255° C. was used as the island component and polystyrene (PS) with a melt viscosity of 100 Pa·s (290° C., shear rate 121.6 sec$^{-1}$) and a Vicat softening temperature of 107° C. was used as the sea component, to obtain islands-in-sea multi-component fibers as described for Example 1 of JP53-106872A. The fibers were treated by trichloroethylene also as described for the examples of JP53-106872A, to remove more than 99% of PS, for obtaining ultrafine fibers. A cross section of the fibers was observed by TEM, and it was found that the ultrafine fibers had a large number average single fiber diameter of 2.0 µm.

The obtained fibers were cut to 2 mm (Comparative Example 9), 3 mm (Comparative Example 10), or 5 mm (Comparative Example 11), to obtain short ultrafine fibers respectively. About 2 g (corresponding to 30 g/m² as the weight per unit area of the synthetic paper made from the fibers) of the short fibers of each length were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. Furthermore, an anionic dispersing agent (Shallol AN-103P produced by Dai-ichi Kogyo Seiyaku Co., Ltd.; molecular weight 10000) was added to the prepared solution by 0.2 wt % based on the weight of the prepared solution. The prepared solution was poured onto filter paper #2 of 5 µm produced by Advantec Co., Ltd placed on a mesh #100 papermaking wire net, to form a sheet. Irrespective of the fiber length, the ultrafine fibers became scattered and could not be removed from the filter paper. So, it was difficult to take them out as a synthetic paper. The reason is considered to be that since the ultrafine fibers were small in the force of cohering to each other unlike nanofibers, it was difficult to produce paper from the ultrafine fibers alone when no binder or the like was used.

Comparative Examples 12, 13 and 14

As described for Comparative Example 9, PET ultrafine fibers with a single fiber diameter of 2.0 µm were obtained. The sea component of the obtained fibers was removed as described for Comparative Example 9, and the remaining island fibers were cut to 3 mm, to obtain short fibers. Two grams (corresponding to 30 g/m as the weight per unit area of the synthetic paper made from the fibers) of the short fibers were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. Then an anionic dispersing agent (Shallol AN-103P produced by Dai-ichi Kogyo Seiyaku Co., Ltd.; molecular weight 10000) was added to the prepared solution by 0.2 wt % based on the weight of the prepared solution. The prepared solution was poured onto a mesh #100 papermaking wire net (Comparative Example 12), or filter paper #2 of 5 µm produced by Advantec Co., Ltd (Comparative Example 13), or a screen woven fabric (fiber diameter 45 µm, pore size 80 µm square; Comparative Example 14), but the ultrafine fibers could not be removed from these filters. The ultrafine fibers were scattered and could not be taken out as a synthetic paper. Since the ultrafine fibers were small in the force of cohering to each other unlike nanofibers, it was difficult to produce paper from the ultrafine fibers alone when no binder or the like was used.

Furthermore, since the ultrafine fibers forming a sheet on the screen woven fabric (Comparative Example 14) were not entangled with the fibers of the screen woven fabric, a synthetic paper integrated with the screen woven fabric could not be obtained contrary to Example 31.

Comparative Examples 15, 16 and 17

As described for Comparative Example 9, PET ultrafine fibers of 2.0 µm were obtained. The sea component of the obtained fibers were removed as described for Comparative Example 9, and the remaining island fibers were cut to 3 mm, to obtain short PET ultrafine fibers. Four grams (corresponding to 60 g/m² as the weight per unit area of the synthetic paper made from the fibers; Comparative Example 15), 6 g (corresponding to 90 g/m² as the weight per unit area of the synthetic paper made from the fibers; Comparative Example 16), or 8 g (corresponding to 120 g/m² as the weight per unit area of the synthetic paper made from the fibers; Comparative Example 17) of the obtained short fibers were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. Then an anionic dispersing agent (Shallol AN-103P produced by Dai-ichi Kogyo Seiyaku Co., Ltd.; molecular weight 10000) was added to the prepared solution by 0.2 wt % based on the weight of the prepared solution. The dispersion was poured onto a mesh #100 papermaking wire net or filter paper #2 of 5 µm produced by Advantec Co., Ltd, to form a sheet. However, in any of the comparative examples, the ultrafine fibers were scattered and could not be removed from the filter paper, not being able to be taken out as a synthetic paper. As can be seen from these examples, ultrafine fibers were small in the force of cohering to each other unlike nanofibers even if a larger weight per unit area was employed, and it was difficult to produce paper from ultrafine fibers alone when no binder or the like was used.

Comparative Example 18

Chips of N6 with a melt viscosity of 50 Pa·s (280° C., 121.6 sec$^{-1}$) and a melting point of 220° C. and chips of PET with a melt viscosity of 210 Pa·s (280° C., 121.6 sec$^{-1}$) and a melting point of 255° C. were blended with each other, with the N6 rate as 20 wt %, and the blend was molten at 290° C. and melt-spun as described for Example 30 at a spinning temperature of 296° C., spinneret face temperature of 280° C. using a cylindrical spinneret with 36 holes, with a discharge hole diameter of 0.30 mm and a discharge hole length of 0.50 mm, then being wound as an undrawn yarn at a spinning speed of 1000 m/min. However, owing to simple chip blending and the large difference between the polymers in melting point, the blend unevenness between N6 and PET was large, and large Barus occurred under the spinneret. In addition, stringiness was poor, and the yarn could not be stably wound. However, a small amount of an undrawn yarn was obtained, and it was drawn as described for Example 30 at a drawing ratio of 3 times with the temperature of the first hot roller kept at 85° C., to obtain a drawn yarn consisting of 36 filaments of 100 dtex. A cross section of the fibers was observed by TEM, and as a result, it was confirmed that island fibers in a single fiber diameter range of 550 to 1400 nm were produced. Furthermore, the number average single fiber diameter of the island fibers was as large as 850 nm, and the sum Pa of single fiber ratios was also 0%.

The sea component of the obtained fibers was removed using an alkali, and the remaining island fibers were cut to 2 mm like the nanofibers of Example 29, to obtain short N6 ultrafine fibers. Two grams (corresponding to 30 g/m² as the weight per unit weight of the synthetic paper made from the fibers) of the obtained short fibers were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. Then an anionic dispersing agent (Shallol AN-103P produced by Dai-ichi Kogyo Seiyaku Co., Ltd.; molecular weight 10000) was added to the prepared solution by 0.2 wt % based on the weight of the prepared solution. The prepared solution was poured onto a mesh #100 papermaking wire net, to form a sheet, and the sheet could be taken out as a synthetic paper. However, the sheet had a low strength and was partially broken and collapsed, and a uniform synthetic paper could not be obtained. The reason is considered to be that the ultrafine fibers were low in the force of cohering to each other unlike nanofibers and especially low in strength when they were wet.

The obtained synthetic paper was sampled in a portion with good evenness, and the sample was observed by SEM. As a result, it was found that the number average single fiber diameter φm was 883 nm, that the sum Pa of single fiber ratios obtained from the distribution of single fiber diameters (see Table 9) was 0%, and that the index Pb of extremal coefficient of single fiber diameters was 8%. The fibers were large in diameter and also large in the irregularity of diameter. Moreover, the synthetic paper had a total weight per unit area of 28.3 g/m², a thickness of 122 μm, a density of 0.23 g/cm³ and an average pore area of 1.5 μm. The hygroscopicity of the synthetic fiber was measured and found to be 2.8%, lower than that of the nanofibers of Example 29. On the other hand, since the synthetic paper had a low strength, the strength, elongation and air permeability could not be measured.

Example 39

Nanofiber Synthetic Paper (11)

PBT with a melt viscosity of 120 Pa·s (262° C., 121.6 sec$^1$) and a melting point of 225° C. and polystyrene copolymerized with 22% of 2-ethylhexyl acrylate (co-PS) were melt-kneaded with the PBT content as 20 wt % as described for Example 29 at a kneading temperature of 240° C., to obtain polymer alloy chips.

The chips were melt-spun as described for Example 29 at a melting temperature of 260° C., at a spinning temperature of 260° C. (spinneret face temperature 245° C.), at a discharge rate per hole of 1.0 g/min and at a spinning speed of 1200 m/min. The obtained undrawn yarn was drawn and heat-treated as described for Example 29 at a drawing temperature of 100° C., at a drawing ratio of 2.49 times and at a thermo-setting temperature of 115° C. The obtained drawn yarn consisted of 36 filaments of 161 dtex and had a strength of 1.4 cN/dtex, an elongation of 33% and an Uster unevenness of 2.0%.

A cross section of the obtained polymer alloy fibers was observed by TEM and found to show an islands-in-sea structure with co-PS as the sea component and with PBT as the island component. The number average diameter of PBT island fibers was 100 nm. Thus polymer alloy fibers in which the copolymerized PET was homogeneously dispersed in nanometer size could be obtained. The polymer alloy fibers were immersed in trichlene, to dissolve out more than 99% of co-PS as the sea component, and the remaining island fibers were dried and cut to 2 mm by a guillotine cutter, to obtain short PBT nanofibers. From the cut fibers, second-step-beaten fibers were obtained as described for Example 29. The second-step-beaten PBT nanofibers had a fiber concentration of 8 wt % and a freeness of 96.

Six point nine grams of the obtained second-step-beaten PBT nanofibers and 0.7 g of a nonionic dispersing agent (Noigen EA-87 produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine) produced by Kumagaya Riki Kogyo Co., Ltd., and water was added to prepare 20 liters of a solution. The prepared solution was poured onto a 25 cm square "screen woven fabric (made of PET, fiber diameter 70 μm, pore size 80 μm square)" placed beforehand on a paper-making wire net, to form a sheet, and the sheet was dehydrated by rollers and dried by a drum dryer, to obtain a PBT nanofiber synthetic paper with the screen woven fabric as the base material.

The surface of the obtained synthetic paper was observed by SEM, and as a result, it was found that a synthetic paper in which PBT nanofibers were individually dispersed could be obtained. The obtained synthetic paper was a uniform synthetic sheet free from pinholes though its thickness was very small. Furthermore, the number average single fiber diameter φm was 102 nm, and the sum Pa of single fiber ratios was 0.100%, the index Pb of extremal coefficient of single fiber diameters being 69%. The synthetic paper had a total weight per unit area of 45.8 g/m², a thickness of 100 μm, a density of 0.46 g/cm³, a strength of 90.4 N/cm and an elongation of 32%. If it is assumed to remove the screen woven fabric portion (weight per unit area 37.4 g/m², thickness 70 μm and density 0.53 g/cm³) from the synthetic paper, the nanofibers only had a weight per unit area of 8.4 g/m², a thickness of 30 μm and a density of 0.28 g/cm³. Moreover, the pore area of the synthetic paper was 0.0040 μm². In the synthetic paper of this example, the number of pinholes of 50 μm or more was 0, and the synthetic paper was highly smooth on the surface, having a surface smoothness of 970 seconds.

The synthetic paper of this example had such a very small pore area and was good in the dispersibility and uniformity of nanofibers. So, it was free from large pinholes and had a small air permeability of 0.40 cc/cm$^2$/sec, and a synthetic paper with a high gas impermeability could be obtained.

Example 40

Nanofiber Synthetic Paper (12)

Twenty weight percent of PP with a melt viscosity of 300 Pa·s (220° C., 121.6 sec$^1$) and a melting point of 162° C. and 80 wt % of the poly-L-lactic acid of Example 38 were melt-kneaded as described for Example 29 at a kneading temperature of 220° C., to obtain polymer alloy chips.

The chips were melt-spun as described for Example 29 at a melting temperature of 220° C., at a spinning temperature of 220° C. (spinneret face temperature 205° C.), at a discharge rate per hole of 2.0 g/min and at a spinning speed of 1200 m/min. The obtained undrawn yarn was drawn and heat-treated as described for Example 29 at a drawing temperature of 90° C., at a drawing ratio of 2.0 times and at a thermosetting temperature of 130° C. The obtained drawn yarn consisted of 12 filaments of 101 dtex and had a strength of 2.0 cN/dtex and an elongation of 47%.

A cross section of the obtained polymer alloy fibers was observed by TEM, and it was found to show an islands-in-sea structure with poly-L-lactic acid as the sea component and PP as the island component. The number average diameter of PP island fibers was 150 nm. Thus polymer alloy fibers in which PP was homogeneously dispersed in nanometer size could be obtained.

The obtained polymer alloy fibers were immersed in 3% sodium hydroxide aqueous solution of 98° C. for 2 hours, to hydrolyze and remove more than 99% of the poly-L-lactic acid component in the polymer alloy fibers. The remaining island fibers were neutralized by acetic acid, washed with water, dried and cut to a length of 2 mm by a guillotine cutter, to obtain short PP nanofibers. From the cut fibers, second-step-beaten fibers were obtained as described for Example 29. The second-step-beaten PP nanofibers had a fiber concentration of 6% and a freeness of 104.

Nine point two grams of the obtained second-step-beaten fibers and 0.9 g of a nonionic dispersing agent (Noigen EA-87 produced by Dai-ichi Kogyo Seiyaku Co., Ltd.; molecular weight 10000) were added into a disintegrator together with 1 liter of water, and the mixture was dispersed for 5 minutes.

The dispersion in the disintegrator was transfused into the vessel of an experimental paper machine (square sheet machine) produced by Kumagaya Riki Kogyo Co., Ltd., and water was added to prepare 20 liters of a solution. The prepared solution was poured onto a 25 cm square "screen woven fabric (made of PET, fiber diameter 70 µm, pore size 80 µm square)" placed beforehand on a papermaking wire net, to form a sheet, and the sheet was dehydrated by rollers and dried by a drum dryer, to obtain a PP nanofiber synthetic paper with the screen woven fabric as the base material.

The surface of the obtained synthetic paper was observed by SEM, and it was found that a synthetic paper in which PP nanofibers were individually dispersed could be obtained. The obtained synthetic paper was a uniform synthetic paper free from pinholes, though the thickness was very small. Furthermore, the PP nanofibers was 154 nm in the number average single fiber diameter φm, 100% in the sum Pa of single fiber ratios and 69% in the index Pb of extremal coefficient of single fiber diameters. The synthetic paper had a total weight per unit area of 45.7 g/m$^2$, a thickness of 102 µm, a density of 0.45 g/cm$^3$, a strength of 91.2 N/cm and an elongation of 33%. If it is assumed to remove the screen woven fabric portion (weight per unit area 37.4 g/m$^2$, thickness 70 µm, density 0.53 g/cm$^3$) from the synthetic paper, the nanofibers only had a weight per unit area of 8.3 g/m$^2$, a thickness of 32 µm and a density of 0.26 g/cm$^3$. The pore area of the synthetic paper was 0.0062 µm$^2$. The synthetic paper of this example had such a very small pore area and was furthermore good in the dispersibility and uniformity of nanofibers. So, the obtained synthetic paper was free from large pinholes and had a small air permeability of 0.73 cc/cm$^2$/sec. So, the synthetic paper obtained had a high gas impermeability. Furthermore, in the compound synthetic paper of this example, the number of pinholes of 50 µm or more was 0, and the synthetic paper was highly smooth on the surface, having a surface smoothness of 770 seconds.

Example 41

Nanofiber Synthetic Paper (13)

Eighty weight percent of PET with a melt viscosity of 280 Pa·s (300° C., 1216 sec$^{-1}$) and 20 wt % of polyphenylene sulfide (PPS) with a melt viscosity of 160 Pa·s (300° C., 1216 sec$^{-1}$) were melt-kneaded using a twin-screw extrusion kneader under the following conditions, to obtain polymer alloy chips. The PPS used here was of straight chain, with its molecular chain ends substituted by calcium ions. The PET used here was 1% in the weight loss when it was held at 300° C. for 5 minutes.

Screw: L/D=45

The total length of kneading portions was 34% of the effective length of screws

The kneading portions were separately installed in the entire screw.

Two back flow portions were provided on the way.

Polymer supply: PPS and PET were separately weighed and separately supplied into the kneader.

Temperature: 300° C.

Vent: Nil

The obtained polymer alloy chips were introduced into a spinning machine as described for Example 29, for being spun. In this case, the spinning temperature was 315° C., and the polymer alloy melt was filtered by a metallic nonwoven fabric with a max filtration diameter of 15 µm, and melt-spun from a spinneret with a spinneret face temperature of 292° C. In this case, a spinneret with a discharge hole diameter of 0.6 mm, having a weighing portion with a diameter of 0.3 mm above the discharge holes, was used. The discharge rate per hole was set at 1.1 g/min. Furthermore, the distance from the bottom face of the spinneret to the cooling start point was 7.5 cm. The discharged filaments were cooled and solidified by 20° C. cooling air for 1 m, and given a process oil mainly composed of a fatty acid ester, passing around the non-heated first take-up roller and the second take-up roller, to be wound at 1000 m/min. In this case, the spinnability was good, and during continuous spinning for 24 hours, no yarn breaking occurred. The fibers were then drawn and heat-treated with the temperature of the first hot roller set at 100° C. and with the temperature of the second hot roller set at 130° C. The drawing ratio between the first and second hot rollers was set at 3.3 times. The polymer alloy fibers were obtained as 240 filaments of 400 dtex and had excellent properties, i.e., a strength of 4.4 cN/dtex, an elongation of 27% and an Uster unevenness of 1.3%. Furthermore, a cross section of the obtained polymer alloy fibers was observed by TEM, and it was found that PPS island fibers with a diameter of less than 100 nm were homogeneously dispersed in the PET used as the sea polymer. The equivalent diameter of the island fibers was analyzed by image analysis software Winroof, and it was found that the average diameter of island fibers was 65 nm. Thus, high polymer alloy fibers with PPS very finely dispersed could be obtained.

The obtained polymer alloy fibers were wound into a hank, to obtain a tow like a hank with a fineness of 100,000 dtex. In this case, a cotton yarn was used to bind the outer circumference of the tow at 30 cm intervals, to prevent that the tow could be scattered during the treatment for removing the sea component. The hank tension was adjusted to keep the fiber density of the tow at 0.05 g/cm$^3$, and the tow was set in the sea component removing device of FIG. 5. Then, 10 wt % sodium hydroxide aqueous solution of 98° C. was used together with 5% owf of "Mercerine PES", an alkali treatment accelerating agent produced by Meisei Chemical Works, Ltd. for alkaline hydrolysis treatment of the tow, for removing the PET as the sea polymer from the polymer alloy fibers, to obtain a tow with a tow fineness of 20,000 dtex consisting of PPS nanofibers. A cross section of the obtained PPS nanofiber tow was observed by TEM, and it was found that the area ratio of nanofibers to all the fibers was 100%, that the number average single fiber diameter ϕm was 60 nm, and that the sum Pa of single fiber ratios was 100%.

The tow consisting of PPS nanofibers was cut to a fiber length of 1 mm using a guillotine cutter, to obtain short PPS nanofibers. In this case, the L/D of the short PPS nanofibers was about 16700.

Thirty grams of the short PPS nanofibers and about 20 liters of water were added into the vessel of a Niagara beater, and the fibers were beaten in the first step for 10 minutes. The fibers were dehydrated by a centrifuge, to obtain first-step-beaten fibers with a fiber concentration of 10 wt %. The first-step-beaten fibers were further beaten in the second step for 10 minutes by a PFI mill, and dehydrated. The obtained second-step-beaten PPS nanofibers had a fiber concentration of 10 wt %.

Five point five grams of the second-step-beaten fibers and 0.5 g of a nonionic dispersing agent (Noigen EA-87 produced by Dai-ichi Kogyo Seiyaku Co., Ltd.; molecular weight 10000) were added into a disintegrator together with 1 liter of water, and the mixture was dispersed for 5 minutes. The dispersion in the disintegrator was transfused into the vessel of an experimental paper machine (square sheet machine), and water was added to prepare 20 liters of a solution. The prepared solution was poured onto a 25 cm square "screen woven fabric (made of PET, fiber diameter 70 μm, pore size 80 μm square)" placed beforehand on a papermaking wire net, to form a sheet, and the sheet was dehydrated by rollers and dried by a drum dryer, to obtain a PPS nanofiber synthetic paper.

The surface of the obtained paper composed of PPS nanofibers was observed by SEM, and it was found that PPS nanofibers were homogeneously dispersed as single fibers and were 60 nm in the number average single fiber diameter ϕm, 100% in the sum Pa of single fiber ratios and 63% in the index Pb of extremal coefficient of single fiber diameters. The synthetic paper had a total area per unit area of 45.6 g/m$^2$, a thickness of 101 μm, a density of 0.45 g/cm$^3$, a strength of 91.4 N/cm and an elongation of 32%. If it is assumed to remove the screen woven fabric portion (weight per unit area 37.4 g/m$^2$, thickness 70 μm, density 0.53 g/cm$^3$) from the synthetic paper, the nanofibers only had a weight per unit area of 8.2 g/m$^2$, a thickness of 31 μm and a density of 0.26 g/cm$^3$. The average pore area of the synthetic paper was 0.0044 μm. Since the synthetic paper of this example had such a very small pore area and was good in the dispersibility and uniformity of nanofibers, it was free from large pinholes. The number of pinholes of 50 μm or more was 0, and the synthetic paper was highly smooth on the surface, having a surface smoothness of 1710 seconds.

Furthermore, the obtained paper had a small air permeability of 0.29 cc/cm$^2$/sec, and therefore had a high gas impermeability. Furthermore, the surface of the PPS synthetic paper contained numerous pores of nanometer level, and it could be suitably used as a liquid filter or a separator for a secondary battery or capacitor, as it was.

The PPS nanofiber paper was further thermally pressed at 180° C., to obtain dense PPS paper. Since it little absorbed moisture to dimensionally change, it was suitable for a circuit board or the like.

Example 42

Nanofiber Synthetic Paper (14)

The dispersion obtained in Example 29 was further diluted to 10 times, to prepare a dispersion with a fiber concentration of 0.0055 wt %. It was sprayed from a spray nozzle onto a melt-blown PP nonwoven fabric with a fiber diameter of about 3 μm (Toraymicron produced by Toray Industries, Inc.) 100 times, and the sprayed fabric was dried by a drum dryer, to form a 30 μm thick N6 nanofiber synthetic paper on the melt-blown PP nonwoven fabric, for obtaining a compound synthetic paper.

The obtained compound synthetic paper was observed by SEM, and as a result, it was found that the N6 nanofibers were 57 nm in the number average single fiber diameter ϕm, 100% in the sum Pa of single fiber ratios and 64% in the index Pb of extremal coefficient of single fiber diameters. The compound synthetic paper had N6 nanofibers homogeneously dispersed on a melt-blown PP nonwoven fabric and was free from large holes and pinholes. The number of pinholes of 50 μm or more was 0, and the synthetic paper was highly smooth on the surface, having a surface smoothness of 650 seconds.

The compound synthetic paper had numerous pores of nanometer level and was suitable for a liquid filter and air filter.

Example 43

Nanofiber Synthetic Paper (15)

The diluted dispersion prepared in Example 42 was sprayed as described for Example 42, except that a foam (Toraypef produced by Toray Industries, Inc.) was used instead of the melt-blown PP nonwoven fabric, to form a 30 μm thick N6 nanofiber synthetic paper on the foam, for obtaining a compound synthetic paper. The compound synthetic paper had the foam uniformly coated with N6 nanofibers and was suitable as an abrasive.

Example 44

Nanofiber Synthetic Paper (16)

A nanofiber compound synthetic paper with a screen woven fabric as the base material was obtained as described for Example 30, except that the amount of the second-step-beaten fibers was 0.55 g.

The surface of the obtained compound synthetic paper was observed by SEM, and as a result, it was found that the nanofibers in the synthetic paper were 58 nm in the number average single fiber diameter ϕm, 100% in the sum Pa of single fiber ratios and 66% in the index Pb of extremal coefficient of single fiber diameters. Furthermore, the synthetic paper had a total weight per unit area of 38.2 g/m², a thickness of 71 μm and a density of 0.54 g/cm³. If it is assumed to remove the screen woven fabric portion (weight per unit area 37.4 g/m², thickness 70 μm, density 0.53 g/cm³) from the synthetic paper, the nanofibers only had a weight per unit area of 0.8 g/m², a thickness of 3.2 μm and a density of 0.25 g/cm³. Furthermore, the air permeability was measured and found to be 28 cc/cm²/sec. Since the synthetic paper was excellent in air permeability, it was suitable as an air filter. Moreover, in the compound synthetic paper of this example, the number of pinholes of 50 μm or more was 0, and the synthetic paper was highly smooth on the surface, having a surface smoothness of 390 seconds.

INDUSTRIAL APPLICABILITY

The compound solutions, emulsions and gels can be used as toilet articles such as beauty care liquids, packs an foundations, medical products such as ointments, wet compresses, materials of cell culture and materials of albumin adsorption, materials of electrolytes and materials of catalyst carriers for various batteries, materials of catalyst carriers for chemical filters, materials for adsorbing hazardous gases, products for architectural materials such as paints, adhesives and wall coating materials, carriers of particles such as activated carbon and titanium oxide for filters, coloring materials for pictures, etc. Furthermore, the compound solutions, emulsions and gels can be used as raw materials for producing various fibrous structures by means of spraying, coating, dipping, etc.

Moreover, the synthetic papers can be used as battery separators, abrasives, industrial filters such as air filters and liquid filters, medical products such as blood filters, insulating paper, circuit boards, etc.

TABLE 1

Comparison of diameter and numbers per 1 cc in 0.01% solution by kind of fiber

| Kind of fibers | Fiber diameter (μm) | Number of fibers (0.01 by weight, per 1 ml) | Specific surface (m²/g) | Aspect ratio (2 mm length) |
|---|---|---|---|---|
| Ordinary fibers | 20 | 160 | 0.035 | 100 |
| Ultrafine fibers | 2 | 16,000 | 0.35 | 1000 |

TABLE 1-continued

Comparison of diameter and numbers per 1 cc in 0.01% solution by kind of fiber

| Kind of fibers | Fiber diameter (μm) | Number of fibers (0.01 by weight, per 1 ml) | Specific surface (m²/g) | Aspect ratio (2 mm length) |
|---|---|---|---|---|
| Nanofibers A | 0.2 | 1.6 million | 3.5 | 10000 |
| Nanofibers B | 0.06 | 18 million | 10.5 | 33000 |

TABLE 2

Comparison of diameter by kind of fiber, and rigidity values

| Kind of fibers | Fiber diameter (μm) | Rigidity values (Relatively compared) |
|---|---|---|
| Ordinary fibers | 20 | 1 |
| Ultrafine fibers | 2 | $1 \times 10^{-4}$ |
| Nanofibers A | 0.2 | $1 \times 10^{-8}$ |
| Nanofibers B | 0.06 | $8.1 \times 10^{-11}$ |

TABLE 3

Distribution of fiber diameter in Example 1

| No | Diameter: φ | Frequency: f | Product: φ*f |
|---|---|---|---|
| 1 | 0 | 0 | 0 |
| 2 | 10 | 2 | 20 |
| 3 | 20 | 5 | 100 |
| 4 | 30 | 13 | 390 |
| 5 | 40 | 32 | 1280 |
| 6 | 50 | 54 | 2700 |
| 7 | 60 | 81 | 4860 |
| 8 | 70 | 65 | 4550 |
| 9 | 80 | 36 | 2880 |
| 10 | 90 | 11 | 990 |
| 11 | 100 | 1 | 100 |
| Number N | | 300 | 17870 |
| Number average single fiber diameter φm | | | 60 |
| Sum Pa of simple fiber ratios | | | 100% |
| Index Pb of extremal coefficient of single fiber diameter | | | 66% |

TABLE 4

| | Kind of fibers | Length of fibers mm | Freenes 1st step beaten | Freenes 2nd step beaten | concentration of NanoF wt % | State of compound |
|---|---|---|---|---|---|---|
| Example 1 | NanoF of Nylon6 | 2 | 362 | 64 | 10 | Gel |
| Example 2 | NanoF of Nylon6 | 2 | — | 157 | 0.10 | Compound solution(water) |
| Example 3 | NanoF of Nylon6 | 2 | — | 157 | 0.01 | Compound solution(water) |
| Example 4 | NanoF of Nylon6 | 2 | 362 | 64 | 1.0 | Compound solution(water) |
| Example 5 | NanoF of Nylon6 | 2 | 362 | 64 | 0.10 | Compound solution(water) |
| Example 6 | NanoF of Nylon6 | 2 | 362 | 64 | 0.01 | Compound solution(water) |
| Example 7 | NanoF of Nylon6 | 2 | 362 | 64 | 1.0 | Compound solution(water) |
| Example 8 | NanoF of Nylon6 | 2 | 362 | 64 | 0.10 | Compound solution(water) |
| Example 9 | NanoF of Nylon6 | 2 | 362 | 64 | 0.01 | Compound solution(water) |
| Example 18 | NanoF of Nylon6 | 2 | — | — | 0.10 | Compound solution(ethanol) |
| Example 19 | NanoF of Nylon6 | 2 | — | — | 0.10 | Compound solution(toluene) |
| Example 22 | NanoF of Nylon6 | 0.2 | 152 | 32 | 0.01 | Compound solution(water) |
| Example 23 | NanoF of Nylon6 | 0.5 | — | 43 | 0.01 | Compound solution(water) |
| Example 24 | NanoF of Nylon6 | 1 | — | 58 | 0.01 | Compound solution(water) |
| Example 25 | NanoF of Nylon6 | 0.2 | — | 32 | 0.01 | Compound solution(water) |
| Example 26 | NanoF of Nylon6 | 0.2 | — | 32 | 0.01 | Compound solution(water) |

TABLE 4-continued

| | | | | | | |
|---|---|---|---|---|---|---|
| Example 27 | NanoF of PBT | 0.5 | — | 96 | 0.01 | Compound solution(water) |
| Example 28 | NanoF of PP | 0.8 | — | 104 | 0.01 | Compound solution(water) |

| | φm nm | Pa % | Pb % | Settling time Min. | Transparency % | Dispersing agent Kind | concentration (wt %) |
|---|---|---|---|---|---|---|---|
| Example 1 | 60 | 100 | 66 | — | — | — | — |
| Example 2 | 63 | 100 | 61 | — | 1.8 | — | — |
| Example 3 | 63 | 100 | 61 | 12 | 53 | — | — |
| Example 4 | 60 | 100 | 66 | — | 0 | — | — |
| Example 5 | 60 | 100 | 66 | — | 1.2 | — | — |
| Example 6 | 60 | 100 | 66 | 10 | 51 | — | — |
| Example 7 | 60 | 100 | 66 | — | 0 | Anion | 0.10 |
| Example 8 | 60 | 100 | 66 | 360 | 2.4 | Anion | 0.10 |
| Example 9 | 60 | 100 | 66 | — | 63 | Anion | 0.10 |
| Example 18 | 61 | 100 | 64 | — | — | — | — |
| Example 19 | 62 | 100 | 63 | — | — | — | — |
| Example 22 | 58 | 100 | 67 | 740 | 78 | Anion | 0.10 |
| Example 23 | 58 | 100 | 67 | 520 | 70 | Anion | 0.10 |
| Example 24 | 58 | 100 | 67 | 410 | 68 | Anion | 0.10 |
| Example 25 | 58 | 100 | 67 | 452 | 65 | Anion | 10 |
| Example 26 | 58 | 100 | 67 | 627 | 83 | Anion | 0.01 |
| Example 27 | 52 | 100 | 69 | 669 | 81 | Nonion | 0.10 |
| Example 28 | 154 | 100 | 69 | 597 | 72 | Nonion | 0.01 |

NanoF: nanofibers

TABLE 5

| | Kind of fibers | Length of fibers mm | Freenes 1st step beaten | Freenes 2nd step beaten | concentration of NanoF wt % | State of compound |
|---|---|---|---|---|---|---|
| Comparative Example 1 | Nylon6(27 μm) | 2 | — | — | 0.10 | Compound solution(water) |
| Comparative Example 2 | Nylon6(27 μm) | 2 | — | — | 0.01 | Compound solution(water) |
| Comparative Example 3 | Nylon6(2 μm) | 2 | — | — | 0.10 | Compound solution(water) |
| Comparative Example 4 | Nylon6(2 μm) | 2 | — | — | 0.01 | Compound solution(water) |
| Comparative Example 5 | Nylon6(27 μm) | 2 | — | — | 0.01 | Compound solution(water) |
| Comparative Example 6 | Nylon6(2 μm) | 2 | — | — | 0.01 | Compound solution(water) |

| | φm μm | Pa % | Pb % | Settling time Min. | Transparency % | Dispersing agent Kind | concentration (wt %) |
|---|---|---|---|---|---|---|---|
| Comparative Example 1 | 27 | 0 | 92 | — | 66 | — | — |
| Comparative Example 2 | 27 | 0 | 92 | 2.7 | 87 | — | — |
| Comparative Example 3 | 2.1 | 0 | 88 | — | 14 | — | — |
| Comparative Example 4 | 2.1 | 0 | 88 | 1.1 | 52 | — | — |
| Comparative Example 5 | 27 | 0 | 88 | 3.7 | — | Anion | 0.10 |
| Comparative Example 6 | 2.1 | 0 | 88 | 1.3 | — | Anion | 0.10 |

TABLE 6

| | Structure of synthetic paper | Binder | Base material | φm nm | Pa % | Pb % | Papermaking property | Weight per unit area g/m² | Thickness μm |
|---|---|---|---|---|---|---|---|---|---|
| Example 29 | NanoF: 100% | None | None | 57 | 100 | 64 | ○ | 8.4 | 30 |
| Example 30 | Whole synthetic paper | None | None | — | — | — | ○ | 45.6 | 102 |
| | Screen woven fabric | | Screen woven fabric | — | — | — | — | 37.4 | 70 |
| | NanoF: 100% | | | 58 | 100 | 66 | — | 8.2 | 32 |

TABLE 6-continued

| | Structure of synthetic paper | Binder | Base material | φm nm | Pa % | Pb % | Papermaking property | Weight per unit area g/m² | Thickness μm |
|---|---|---|---|---|---|---|---|---|---|
| Example 31 | Whole synthetic paper | None | None | | | | ○ | 32.3 | 154 |
| | NanoF: 80% | | | 59 | 100 | 65 | — | — | — |
| | Ultrafine fibers: 20% | | | | | | | — | — |
| Example 32 | Whole synthetic paper | Pulp | None | | | | ○ | 31.6 | 243 |
| | NanoF: 2.4% | | | 59 | 100 | 63 | — | — | — |
| | Ultrafine fibers: 87% | | | | | | | — | — |
| Example 33 | Whole synthetic paper | None | None | | | | ○ | 39.5 | 78 |
| | NanoF: 100% | | Screen woven fabric | | | | | 37.4 | 70 |
| | | | | 57 | 99 | 73 | | 2.1 | 8.0 |
| Example 34 | Whole synthetic paper | None | None | | | | ○ | 46.9 | 111 |
| | NanoF: 100% | | Screen woven fabric | | | | | 37.4 | 70 |
| | | | | 114 | 98 | 58 | | 8.7 | 41 |
| Example 35 | NanoF: 100% | — | Ultrafine fibers Pulp paper | 57 | 99 | 72 | ○ | 42.2 | 285 |
| Example 36 | NanoF: 100% | — | Nonwoven fabric | 57 | 99 | 63 | ○ | 35.6 | 160 |
| Example 37 | Whole synthetic paper | None | None | | | | ○ | 46.5 | 108 |
| | NanoF: 100% | | Screen woven fabric | | | | | 37.4 | 70 |
| | | | | 59 | 98 | 71 | | 9.1 | 38 |
| Example 38 | NanoF: 100% | None | None | 56 | 100 | 62 | ○ | 8.4 | 34 |

| | Density g/cm³ | Average pore area μm² | Air permeability cc/cm²/sec | Surface smoothness sec. | Strength N/cm | Elongation % | Moisture absorption coeifcient % |
|---|---|---|---|---|---|---|---|
| Example 29 | 0.28 | 0.0033 | 0.35 | 1660 | 2.2 | 12 | 6.4 |
| Example 30 | 0.45 | — | 0.27 | 830 | 91.2 | 34 | 5.7 |
| | 0.53 | — | — | — | — | — | — |
| | 0.26 | 0.0045 | — | — | — | — | — |
| Example 31 | 0.21 | 0.0113 | 11 | 320 | 1.5 | 7.3 | 5.1 |
| | — | — | — | — | — | — | — |
| | — | — | — | — | — | — | — |
| Example 32 | 0.13 | 0.0470 | 34 | 220 | 3.1 | 15 | — |
| | — | — | — | — | — | — | — |
| | — | — | — | — | — | — | — |
| Example 33 | 0.51 | — | 0.66 | 430 | 91.2 | 34 | — |
| | 0.53 | — | — | — | — | — | — |
| | 0.26 | 0.0042 | — | — | — | — | — |
| Example 34 | 0.42 | — | 0.63 | 1180 | 91.2 | 34 | — |
| | 0.53 | — | — | — | — | — | — |
| | 0.21 | 0.0084 | — | — | — | — | — |
| Example 35 | 0.15 | 0.0174 | 23 | 560 | 3.2 | 16 | — |
| Example 36 | 0.23 | 0.0153 | 15 | 380 | 3.5 | 43 | — |
| Example 37 | 0.44 | — | 0.33 | 900 | 91.2 | 34 | — |
| | 0.53 | — | — | — | — | — | — |
| | 0.24 | 0.0051 | — | — | — | — | — |
| Example 38 | 0.26 | 0.0037 | 0.37 | 1680 | 2.0 | 13 | 6.1 |

NanoF: nanofibers

TABLE 7

| | Structure of synthetic paper | Binder | Base material | φm nm | Pa % | Pb % | Papermaking property | Weight per unit area g/m² | Thickness μm |
|---|---|---|---|---|---|---|---|---|---|
| Example 39 | Whole synthetic paper | None | | — | — | — | ○ | 45.8 | 100 |
| | Screen woven fabric | | Screen woven fabric | — | — | — | | 37.4 | 70 |
| | NanoF: 100% | | | 102 | 100 | 69 | — | 8.4 | 30 |
| Example 40 | Whole synthetic paper | None | | — | — | — | ○ | 45.7 | 102 |
| | Screen woven fabric | | Screen woven fabric | — | — | — | | 37.4 | 70 |
| | NanoF: 100% | | | 154 | 100 | 69 | — | 8.3 | 32 |
| Example 41 | Whole synthetic paper | None | | — | — | — | ○ | 45.6 | 101 |
| | Screen woven fabric | | Screen woven fabric | — | — | — | | 37.4 | 70 |
| | NanoF: 100% | | | 60 | 100 | 63 | — | 8.2 | 31 |
| Example 42 | Whole synthetic paper | None | | — | — | — | ○ | — | — |
| | Nonwoven fabric | | Nonwoven fabric | — | — | — | | — | — |
| | NanoF: 100% | | | 57 | 100 | 64 | — | — | 30 |

TABLE 7-continued

| | | | | | | | | | |
|---|---|---|---|---|---|---|---|---|---|
| Example 43 | Whole synthetic paper | None | | — | — | — | ○ | — | — |
| | Foam | | Foam | — | — | — | — | — | 30 |
| | | | NanoF: 100% | 57 | 100 | 64 | — | — | |
| Example 44 | Whole synthetic paper | None | | — | — | — | ○ | 38.2 | 71 |
| | Screen woven fabric | | Screen woven fabric | — | — | — | — | 37.4 | 70 |
| | | | NanoF: 100% | 58 | 100 | 66 | — | 0.8 | 3.2 |
| Comparative Example 9, 10, 11 | 2 μm PET 2, 3, 5mm length | None | None | — | — | — | x | — | — |
| Comparative Example 12, 13, 14 | 2 μm PET | None | None, Filter paper, Screen woven fabric | — | — | — | x | — | — |
| Comparative Example 15, 16, 17 | 2 μm PET content 4, 6, 8 g | None | None | — | — | — | x | — | — |
| Comparative Example 18 | 1 μm PET | None | None | 883 | 0 | 8 | △ | 28.3 | 122 |

| | Density g/cm³ | Average pore area μm² | Air permeability cc/cm²/sec | Surface smoothness sec. | Strength N/cm | Elongation % | Moisture absorption coeifficient % |
|---|---|---|---|---|---|---|---|
| Example 39 | 0.46 | — | 0.40 | 970 | 90.4 | 32 | — |
| | 0.53 | — | — | — | — | — | — |
| | 0.28 | 0.0040 | — | — | — | — | — |
| Example 40 | 0.45 | — | 0.73 | 770 | 91.2 | 33 | — |
| | 0.53 | — | — | — | — | — | — |
| | 0.26 | 0.0062 | — | — | — | — | — |
| Example 41 | 0.45 | — | 0.29 | 1710 | 91.4 | 32 | — |
| | 0.53 | — | — | — | — | — | — |
| | 0.26 | 0.0044 | — | — | — | — | — |
| Example 42 | — | — | — | 650 | — | — | — |
| | — | — | — | — | — | — | — |
| | — | — | — | — | — | — | — |
| Example 43 | — | — | — | — | — | — | — |
| | — | — | — | — | — | — | — |
| | — | — | — | — | — | — | — |
| Example 44 | 0.54 | — | 28 | 390 | — | — | — |
| | 0.53 | — | — | — | — | — | — |
| | 0.25 | 0.0043 | — | — | — | — | — |
| Comparative Example 9, 10, 11 | — | — | — | — | — | — | — |
| Comparative Example 12, 13, 14 | — | — | — | — | — | — | — |
| Comparative Example 15, 16, 17 | — | — | — | — | — | — | — |
| Comparative Example 18 | 0.23 | 1.5 | — | — | — | — | 2.8 |

NanoF: nanofibers

TABLE 8

Distribution of fiber diameter in Example 29

| No | Diameter: φ | Frequency: f | Product: φ*f |
|---|---|---|---|
| 1 | 0 | 0 | 0 |
| 2 | 10 | 2 | 20 |
| 3 | 20 | 6 | 120 |
| 4 | 30 | 18 | 540 |
| 5 | 40 | 44 | 1760 |
| 6 | 50 | 63 | 3150 |
| 7 | 60 | 76 | 4560 |
| 8 | 70 | 56 | 3920 |
| 9 | 80 | 25 | 2000 |
| 10 | 90 | 9 | 810 |
| 11 | 100 | 1 | 100 |
| Number N | | 300 | 16980 |
| Number average single fiber diameter φm | | | 57 |
| Sum Pa of single | | | 100% |
| Index Pb of extremal coefficient of single fiber diameter | | | 64% |

TABLE 9

Distribution of fiber diameter in Comparative Example 18

| No | Diameter: φ | Frequency: f | Product: φ*f |
|---|---|---|---|
| 0 | 550 | 0 | 0 |
| 1 | 600 | 5 | 3000 |
| 2 | 650 | 10 | 6500 |
| 3 | 700 | 17 | 11900 |
| 4 | 750 | 26 | 19500 |
| 5 | 800 | 41 | 32800 |
| 6 | 850 | 50 | 42500 |
| 7 | 900 | 55 | 49500 |
| 8 | 950 | 36 | 34200 |
| 9 | 1000 | 24 | 24000 |
| 10 | 1050 | 14 | 14700 |
| 11 | 1100 | 9 | 9900 |
| 12 | 1150 | 3 | 3450 |
| 13 | 1200 | 2 | 2400 |
| 14 | 1250 | 3 | 3750 |
| 15 | 1300 | 1 | 1300 |
| 16 | 1350 | 2 | 2700 |
| 17 | 1400 | 2 | 2800 |
| Number N | | 300 | 264900 |
| Number average single fiber diameter φm | | | 883 |
| Sum Pa of simple fiber ratios | | | 0% |

TABLE 9-continued

Distribution of fiber diameter in Comparative Example 18

| No | Diameter: φ | Frequency: f | Product: φ*f |
|---|---|---|---|
| Index Pb of extremal coefficient of single fiber diameter | | | 8% |

The invention claimed is:

1. A nanofiber synthetic paper comprising disarranged nanofibers made of a thermoplastic polymer by melt spinning a polymer alloy into polymer alloy fibers comprising a sea component and island components and then removing the sea component to form the disarranged nanofibers from the island components in a homogeneously dispersed arrangement, and of 1 to 500 nm in the number average single fiber diameter and 70% or more in the sum Pa of single fiber ratios, wherein the freeness of the disarranged nanofibers is 350 or less, the fiber length of nanofibers in the nanofiber synthetic paper is 0.1 to 20 mm, the ratio (L/D) of the fiber length L (mm) to the number average single fiber diameter D (mm) is 3,000 to 50,000, and the index Pb of extremal coefficient of the single fiber diameters expressing the rate of the fibers failing within a range of plus and minus 15 nm from the number average single fiber diameter is 60% or more.

2. A nanofiber synthetic paper comprising disarranged nanofibers made of a thermoplastic polymer by melt spinning a polymer alloy into polymer alloy fibers comprising a sea component and island components and then removing the sea component to form the disarranged nanofibers from the island components in a homogeneously dispersed arrangement, and of 1 to 200 nm in the number average single fiber diameter and 70% or more in the sum Pa of single fiber ratios, wherein the fiber length of nanofibers in the nanofiber synthetic paper is 0.1 to 20 mm, the ratio (L/D) of the fiber length L (mm) to the number average single fiber diameter D (mm) is 3,000 to 50,000, and the index Pb of extremal coefficient of the single fiber diameters expressing the rate of the fibers falling within a range of plus and minus 15 nm from the number average single fiber diameter is 60% or more.

3. A nanofiber synthetic paper, according to claim 1, which has a weight per unit area of 50 μg/m$^2$ or less.

4. A nanofiber synthetic paper, according to claim 1, which has a thickness of 10 μm or more.

5. A nanofiber synthetic paper, according to claim 1, which has a density of 0.3 g/cm$^3$ or less.

6. A nanofiber synthetic paper, according to claim 1, which has a number average pore area of 1 μm$^2$ or less.

7. A nanofiber synthetic paper, according to claim 1 or 2, which has an air permeability of 30 cc/cm$^2$/sec or less.

8. A nanofiber synthetic paper, according to claim 1 wherein the number of holes with a diameter of 50 μm or more passing through from the front side to the reverse side of the synthetic paper is 0 to 1000 holes/cm$^2$.

9. A nanofiber synthetic paper, according to claim 1 or 2, which has a surface smoothness of 300 seconds or more.

10. A nanofiber synthetic paper, according to claim 1, wherein the thermoplastic polymer constituting the disarranged nanofibers has a melting point of 165° C. or higher.

11. A nanofiber synthetic paper, according to claim 1, wherein the thermoplastic polymer constituting the disarranged nanofibers is at least one selected front the group consisting of polyesters, polyamides, polyolefins, polyphenylene sulfide, phenol resins, polyacrylonitrile, polyvinyl alcohol, polysulfones, polyurethanes, fluorine-based polymers and their derivatives.

12. A nanofiber synthetic paper, according to claim 1, which further contains at least 5 wt % or more of other fibers with a number average single fiber diameter of 1 μm or more.

13. A nanofiber synthetic paper, according to claim 1, which further contains other fibers with a number average single fiber diameter of 1 μm or more, and 3 wt % or less of the disarranged nanofibers.

14. A nanofiber synthetic paper, according to claim 1, wherein the disarranged nanofibers are laminated on a substrate.

15. A nanofiber synthetic paper, according to claim 14, wherein the substrate is selected from a woven fabric, knitted fabric, nonwoven fabric and foam.

16. A compound synthetic paper comprising the nanofiber synthetic paper as set forth in claim 1.

17. A molded synthetic paper comprising the nanofiber synthetic paper as set forth in claim 1.

* * * * *

UNITED STATES PATENT AND TRADEMARK OFFICE
CERTIFICATE OF CORRECTION

PATENT NO. : 8,501,642 B2
APPLICATION NO. : 10/589411
DATED : August 6, 2013
INVENTOR(S) : Naruse et al.

Page 1 of 1

It is certified that error appears in the above-identified patent and that said Letters Patent is hereby corrected as shown below:

In the Specification

In Column 61

At line 29, please change "(AMR)" to -- ($\Delta$MR) --.

In Column 62

At line 54, please change "(AMR)" to -- ($\Delta$MR) --.

In Column 63

At line 56, please change "(AMR)" to -- ($\Delta$MR) --.

In Column 71

At line 20, please change "(AMR)" to -- ($\Delta$MR) --.

Signed and Sealed this
Twenty-ninth Day of April, 2014

Michelle K. Lee
*Deputy Director of the United States Patent and Trademark Office*